US008574597B2

(12) United States Patent
Zlotnick

(10) Patent No.: US 8,574,597 B2
(45) Date of Patent: Nov. 5, 2013

(54) IMMUNOGENIC COMPOSITIONS FOR THE PREVENTION AND TREATMENT OF MENINGOCOCCAL DISEASE

(75) Inventor: Gary Warren Zlotnick, New Windsor, NY (US)

(73) Assignee: Wyeth LLC, Madison, NJ (US)

( * ) Notice: Subject to any disclaimer, the term of this patent is extended or adjusted under 35 U.S.C. 154(b) by 1390 days.

(21) Appl. No.: 12/004,869

(22) Filed: Dec. 21, 2007

(65) Prior Publication Data

US 2011/0189187 A1    Aug. 4, 2011

Related U.S. Application Data

(60) Provisional application No. 60/876,486, filed on Dec. 22, 2006.

(51) Int. Cl.
| A61K 39/095 | (2006.01) |
| A61K 39/02 | (2006.01) |
| A61K 39/116 | (2006.01) |
| A61K 39/00 | (2006.01) |
| A61K 39/385 | (2006.01) |
| A61K 38/00 | (2006.01) |
| C07K 1/00 | (2006.01) |

(52) U.S. Cl.
USPC .................. 424/250.1; 424/234.1; 424/249.1; 424/184.1; 424/190.1; 424/203.1; 514/1.1; 530/350; 530/825

(58) Field of Classification Search
None
See application file for complete search history.

(56) References Cited

U.S. PATENT DOCUMENTS

| 4,376,110 A | 3/1983 | David et al. |
| 4,554,101 A | 11/1985 | Hopp |
| 4,650,764 A | 3/1987 | Temin et al. |
| 4,666,829 A | 5/1987 | Glenner et al. |
| 4,797,368 A | 1/1989 | Carter et al. |
| 4,861,719 A | 8/1989 | Miller |
| 4,912,094 A | 3/1990 | Myers et al. |
| 4,925,792 A | 5/1990 | Rappuoli |
| 4,980,289 A | 12/1990 | Temin et al. |
| 5,057,540 A | 10/1991 | Kensil et al. |
| 5,078,996 A | 1/1992 | Conlon, III et al. |
| 5,124,263 A | 6/1992 | Temin et al. |
| 5,139,941 A | 8/1992 | Muzyczka et al. |
| 5,254,339 A | 10/1993 | Morein |
| 5,399,346 A | 3/1995 | Anderson et al. |
| 5,459,127 A | 10/1995 | Felgner et al. |
| 5,514,581 A | 5/1996 | Ferrari et al. |
| 5,550,213 A | 8/1996 | Anderson et al. |
| 5,565,204 A | 10/1996 | Kuo et al. |
| 5,580,859 A | 12/1996 | Felgner et al. |
| 5,583,038 A | 12/1996 | Stover |
| 5,589,466 A | 12/1996 | Felgner et al. |
| 5,614,382 A | 3/1997 | Metcalf |
| 5,668,004 A | 9/1997 | O'Donnell |
| 5,723,127 A | 3/1998 | Scott et al. |
| 5,739,118 A | 4/1998 | Carrano et al. |
| 5,955,580 A | 9/1999 | Green et al. |
| 6,113,918 A | 9/2000 | Johnson et al. |
| 6,130,085 A | 10/2000 | Hamers et al. |
| 6,207,646 B1 | 3/2001 | Krieg et al. |
| 6,270,775 B1 | 8/2001 | Cleary |
| 6,355,253 B1 | 3/2002 | Zlotnick |
| 6,355,255 B1 | 3/2002 | Cleary et al. |
| 6,951,653 B2 | 10/2005 | Cleary et al. |
| 7,576,176 B1 | 8/2009 | Fraser et al. |
| 7,785,608 B2 * | 8/2010 | Zlotnick et al. ............ 424/249.1 |
| 8,039,007 B2 * | 10/2011 | Rappuoli et al. ........... 424/250.1 |
| 8,101,194 B2 | 1/2012 | Zlotnick et al. |
| 2006/0251670 A1 | 11/2006 | Comanducci et al. |
| 2007/0020622 A1 | 1/2007 | Lee et al. |
| 2011/0076299 A1 | 3/2011 | Zlotnick et al. |
| 2012/0034261 A1 | 2/2012 | Zlotnick et al. |

FOREIGN PATENT DOCUMENTS

| CA | 2 012 311 C | 9/1990 |
| EP | 0 125 023 B1 | 11/1984 |
| EP | 0 171 496 B1 | 2/1986 |
| EP | 0 173 494 A2 | 3/1986 |
| EP | 0 184 187 A2 | 6/1986 |
| EP | 0 185 573 B1 | 6/1986 |
| EP | 0 178 220 B1 | 1/1992 |
| EP | 0467714 A1 | 1/1992 |
| EP | 0 488 528 B1 | 11/1995 |
| EP | 0 453 242 B1 | 8/1996 |
| EP | 1296713 B1 | 9/2003 |
| EP | 1326634 B1 | 4/2006 |
| EP | 2351767 A2 | 8/2011 |
| JP | 1144977 A | 6/1989 |
| WO | WO 86/01533 A1 | 3/1986 |
| WO | WO 87/01130 A1 | 2/1987 |
| WO | WO 87/02671 A1 | 5/1987 |

(Continued)

OTHER PUBLICATIONS

Bantam Medical Dictionary, Third Edition 302 (2000), pp. 302-303.
Biocomputing: Informatics and Genome Projects, Smith, D. W., ed., Academic Press, New York, 1993.
BLAST Manual, Altschul, S., et al., NCBI NLM NIH Bethesda, Md. 20894; Altschul, S., et al., 1990.
Computational Molecular Biology, Lesk, A. M., ed., Oxford University Press, New York, 1988.
Computer Analysis of Sequence Data, Part I, Griffin, A. M., and Griffin, H. G., eds., Humana Press, New Jersey, 1994, pp. 1-9.
Database Geneseq 'Online' "*N. gonorrhoeae* amino acid sequence SEQ ID 1586", XP002320505, Mar. 7, 2003.

(Continued)

*Primary Examiner* — S. Devi
(74) *Attorney, Agent, or Firm* — Anna C. Chau

(57) ABSTRACT

The present invention relates to *Neisseria* ORF2086 proteins, crossreactive immunogenic proteins which can be isolated from nesserial strains or prepared recombinantly, including immunogenic portions thereof, biological equivalents thereof, antibodies that immunospecifically bind to the foregoing and nucleic acid sequences encoding each of the foregoing, as well as the use of same in immunogenic compositions that are effective against infection by *Neisseria meningitidis* serogroup B.

25 Claims, 21 Drawing Sheets

(56) References Cited

FOREIGN PATENT DOCUMENTS

| | | |
|---|---|---|
| WO | WO 89/07150 A1 | 8/1989 |
| WO | WO 90/02806 A1 | 3/1990 |
| WO | 9010458 A1 | 9/1990 |
| WO | WO 91/18088 A1 | 11/1991 |
| WO | WO 92/05263 A1 | 4/1992 |
| WO | WO 92/19265 | 11/1992 |
| WO | WO 93/09239 A1 | 5/1993 |
| WO | WO 94/12649 A2 | 6/1994 |
| WO | WO 94/21807 A2 | 9/1994 |
| WO | WO 94/26914 A1 | 11/1994 |
| WO | WO 94/28152 A1 | 12/1994 |
| WO | WO 94/28938 A1 | 12/1994 |
| WO | WO 95/02697 A1 | 1/1995 |
| WO | WO 95/07358 A1 | 3/1995 |
| WO | WO 95/18863 A1 | 7/1995 |
| WO | WO 95/21931 A1 | 8/1995 |
| WO | WO 95/22617 A1 | 8/1995 |
| WO | WO 95/26411 A2 | 10/1995 |
| WO | WO 95/28494 A1 | 10/1995 |
| WO | WO 96/10038 A1 | 4/1996 |
| WO | 96/14086 A1 | 5/1996 |
| WO | WO 96/17823 A1 | 6/1996 |
| WO | WO 96/22378 A1 | 7/1996 |
| WO | WO 96/25508 A1 | 8/1996 |
| WO | 9629412 A1 | 9/1996 |
| WO | 9640718 A1 | 12/1996 |
| WO | WO 96/39036 A1 | 12/1996 |
| WO | WO 97/19182 A1 | 5/1997 |
| WO | 98/08543 A1 | 3/1998 |
| WO | 98/08874 A1 | 3/1998 |
| WO | 9817805 A2 | 4/1998 |
| WO | WO 99/01157 A1 | 1/1999 |
| WO | WO 99/01158 A1 | 1/1999 |
| WO | WO 99/01175 A1 | 1/1999 |
| WO | 99/10372 A1 | 3/1999 |
| WO | WO 99/24578 A2 | 5/1999 |
| WO | WO 99/27944 A1 | 6/1999 |
| WO | 99/36544 A2 | 7/1999 |
| WO | 9940200 A1 | 8/1999 |
| WO | 99/55730 A2 | 11/1999 |
| WO | 9955872 A1 | 11/1999 |
| WO | WO 99/57280 A2 | 11/1999 |
| WO | 99/61053 A1 | 12/1999 |
| WO | WO 00/18434 A1 | 4/2000 |
| WO | WO 00/22430 A2 | 4/2000 |
| WO | 0042192 | 7/2000 |
| WO | 0043518 | 7/2000 |
| WO | 00/50075 A2 | 8/2000 |
| WO | WO 00/44890 A1 | 8/2000 |
| WO | 00/66741 A2 | 11/2000 |
| WO | 00/71574 A2 | 11/2000 |
| WO | 0071725 A2 | 11/2000 |
| WO | WO 00/66791 A1 | 11/2000 |
| WO | 01/04316 A2 | 1/2001 |
| WO | 01/31019 A2 | 5/2001 |
| WO | 01/38350 A2 | 5/2001 |
| WO | 0137863 A2 | 5/2001 |
| WO | 01/52885 A1 | 7/2001 |
| WO | WO 01/64920 A2 | 9/2001 |
| WO | WO 01/64922 A2 | 9/2001 |
| WO | 02/058737 A2 | 8/2002 |
| WO | 02/083710 A2 | 10/2002 |
| WO | 02/083711 A2 | 10/2002 |
| WO | 02079246 A2 | 10/2002 |
| WO | WO 02/079243 A2 | 10/2002 |
| WO | WO 02/098368 A2 | 12/2002 |
| WO | WO 02/098369 A2 | 12/2002 |
| WO | 03/007985 A2 | 1/2003 |
| WO | 03/009869 A1 | 2/2003 |
| WO | 03/020756 A2 | 3/2003 |
| WO | WO 03/063765 A2 | 3/2003 |
| WO | 03/047619 A2 | 6/2003 |
| WO | WO 03/063766 A2 | 8/2003 |
| WO | 03/080678 A1 | 10/2003 |
| WO | 03/094834 A2 | 11/2003 |
| WO | 03/094960 A2 | 11/2003 |
| WO | 2004/019977 A2 | 3/2004 |
| WO | 2004/019992 A1 | 3/2004 |
| WO | 2004032958 A1 | 4/2004 |
| WO | 2004/046177 A2 | 6/2004 |
| WO | WO 2004048404 A2 * | 6/2004 |
| WO | 2004/067033 A1 | 8/2004 |
| WO | 2004067030 A2 | 8/2004 |
| WO | WO 2004/083251 A2 | 9/2004 |
| WO | WO 2004/094596 A2 | 11/2004 |
| WO | 2005/000345 A2 | 1/2005 |
| WO | 2005/004908 A1 | 1/2005 |
| WO | 2005/020964 A1 | 3/2005 |
| WO | 2005/032583 A2 | 4/2005 |
| WO | 2005/033148 A1 | 4/2005 |
| WO | 2005/090985 A1 | 9/2005 |
| WO | 2005/090986 A2 | 9/2005 |
| WO | 2005/102384 A2 | 11/2005 |
| WO | 2005/103230 A2 | 11/2005 |
| WO | 2005/105140 A2 | 11/2005 |
| WO | 2005/105141 A2 | 11/2005 |
| WO | WO 2005/108580 A1 | 11/2005 |
| WO | 2005/113607 A2 | 12/2005 |
| WO | 2006/000920 A2 | 1/2006 |
| WO | 2006/011060 A2 | 2/2006 |
| WO | 2006/027685 A2 | 3/2006 |
| WO | 2006024954 A2 | 3/2006 |
| WO | 2006/046143 A2 | 5/2006 |
| WO | 2006/067632 A2 | 6/2006 |
| WO | 2006/075170 A1 | 7/2006 |
| WO | 2006/081259 A2 | 8/2006 |
| WO | 2006/096701 A2 | 9/2006 |
| WO | 2006/120576 A2 | 11/2006 |
| WO | 2007/000314 A2 | 1/2007 |
| WO | 2007/000341 A2 | 1/2007 |
| WO | 2007/000342 A2 | 1/2007 |
| WO | 2007/000343 A2 | 1/2007 |
| WO | 2007/026249 A2 | 3/2007 |
| WO | 2007/028408 A1 | 3/2007 |
| WO | 2007060548 A2 | 5/2007 |
| WO | 2007/071786 A2 | 6/2007 |
| WO | 2007/111940 A2 | 10/2007 |
| WO | 2007/144316 A2 | 12/2007 |
| WO | 2007/144317 A2 | 12/2007 |
| WO | 2008/001222 A2 | 1/2008 |
| WO | 2008/013943 A2 | 1/2008 |
| WO | 2008001224 A2 | 1/2008 |

OTHER PUBLICATIONS

Database Geneseq 'Online' "*Neisseria meningitidis* ORF 741 protein sequence SEQ ID 2536", XP002320506, Mar. 21, 2000.
Database Geneseq 'Online' "*Neisseria meningitidis* ORF 741 protein sequence SEQ ID 2534", XP002320504, Mar. 21, 2000.
Database UniProt 'Online', "Hypothetical Protein NMB1870", XP002308111, Oct. 1, 2000.
Database UniProt 'Online', "Putative lipoprotein *N meningitidis* (Serotype A)", XP003220503, Oct. 1, 2000.
Gribskov, M. and Devereux, J., ed. Sequence Analysis Primer. Stockton Press, New York (1991).
Griffin, A. M. and Griffin, H. G., ed., Computer Analysis of Sequence Data, Part I. Humana Press, New Jersey (1994).
Lesk, A. M., ed. Computational Molecular Biology. Oxford University Press, New York (1988).
MMWR (Morbidity and Mortality Weekly Report), Case Definitions for Infectious Conditions Under Public Health Surveillance, Recommendations and Reports, May 2, 1997, vol. 46., No. RR-10.
The Random House Dictionary, Random House, New York, p. 546, 1984.
Sambrook, J., E.F. Fritsch, and T. Maniatis, 1989, *Molecular Cloning: A Laboratory Manual*, Cold Spring Harbor Laboratory Press, Cold Spring Harbor, NY, chapters 9 and 11.
Sambrook, J. and D. W. Russell. Current Protocols in Molecular Biology. John Wiley & Sons, Inc., New York (1995).
Sambrook, J. et al. 2001. *Molecular cloning a laboratory manual*, Third ed, vol. 3. Cold Spring Harbor Laboratory Press, Cold Spring Harbor, New York.

(56) References Cited

OTHER PUBLICATIONS

Sequence Analysis in Molecular Biology, von Heinje, G., Academic Press, 1987.
Sequence Analysis Primer, Gribskov, M. and Devereux, J., eds., M Stockton Press, New York, 1991.
Smith, D. W.. ed., Biocomputing: Informatics and Genome Projects. Academic Press, New York (1993).
Abdillahi et al., WCE; FEMS Micro. Lett., 48 (1987) 367-371.
Abdillahi et al., 1988, *Microbial Pathogenesis* 4(1):27-32.
Achtman, M., 1995, *Trends in Microbiology* 3(5):186-92.
Ambrosch et al., 1983, Bulletin of the World Health Organization 61(2):317-23.
Altschul, S. F. et al. 1990. Basic local alignment search tool, *J. Mol. Biol.* 215:403-410.
Altschul, S. F. et al. 1990. Protein database searches for multiple alignments, *Proc. Natl. Acad. Sci.*, vol. 87, pp. 5509-5513, Jul. 1990.
Altschul, S. F. et al. 1997. Gapped BLAST and PSI-BLAST: a new generation of protein database search programs. *Nucleic Acids Res.* 25:3389-402.
Alm, R. A., et al. 1999. Genomic-sequence comparison of two unrelated isolates of the human gastric pathogen *Helicobacter pylori* [published erratum appears in Nature Feb. 25, 1999;397(6721):719]. *Nature.* 397:176-80.
Anderson, T. F. 1951. Techniques for the preservation of three-dimensional structure in preparing specimens for the electron microscope. Trans N Y Acad Sci. 13:130-134.
Bateman, A. T., 2000, The Pfam protein families database. Nuc. Acids. Res. 28:263-266.
Beard et al., Virology, 1990, 75-81.
Bender et al., *J. Virol.*, 1987, 61:1639-1646.
Benson, G. 1999. Tandem repeats finder: a program to analyze DNA sequences. Nucleic Acids Res. 27:573-80.
Bernstein et al., *Genet. Eng.*,1985, 7:235.
Better et al., 1988, *Science* 240:1041-1043.
Beuvery et al. 1983. Infect. Immun. 40:369-380.
Boulianne et al., 1984, Nature 312:643-646.
Cabilly et al., 1984, *Proc. Natl. Acad. Sci.* USA 81:3273-3277.
Carillo, H., and Lipman, D., SIAM J. *Applied Math.*, 48:1073 (1988).
Chen, C. C. et al. 1989. Cloning and expression of the streptococcal C5a peptidase gene in *Escherichia coli*: linkage to the type 12 M protein gene. *Infect. Immun.* 57:1740-1745.
Chmouryguina, I., A. et al. 1996. Conservation of the C5a peptidase genes in group A and B streptococci. *Infect. Immun.* 64:2387-2390.
Cockerill, F. R., III et al. 1998. Molecular, serological, and clinical features of 16 consecutive cases of invasive streptococcal disease. Southeastern Minnesota Streptococcal Working Group. *Clin Infect Dis.* 26:1448-58.
Courtney, H. S. et al. 1994. Cloning, sequencing, and expression of a fibronectin/fibrinogen-binding protein from group A streptococci. *Infect Immun.* 62:3937-46.
Cserzo, M., E. et al. 1997. Prediction of transmembrane alpha-helices in prokaryotic membrane proteins: the dense alignment surface method. *Protein Engineering.* 10:673-6.
Cunningham, M. W., and A. Quinn. 1997. Immunological crossreactivity between the class I epitope of streptococcal M protein and myosin. *Adv Exp Med Biol.* 418:887-92.
Curiel et al., *Hum. Gene Ther.*, 1992, 3:147-154; Wu and Wu, *J. Biol. Chem.*, 1987, 262:4429-4432).
Dale, J. B. et al. 1994. Passive protection of mice against group A streptococcal pharyngeal infection by lipoteichoic acid. *J Infect Dis.* 169:319-23.
Dale, J. B. et al. 1996. Recombinant, octavalent group A streptococcal M protein vaccine. *Vaccine.* 14:944-8.
Dale, J. B. et al. 1996. Hyaluronate capsule and surface M protein in resistance to opsonization of group A streptococci. *Infect Immun.* 64:1495-501.
De et al. 2000. Purification and characterization of *Streptococcus pneumoniae* palmitoylated pneumococcal surface adhesin A expressed in *Escherichia coli. Vaccine.* Mar. 6;18(17):1811-21.

Devereux, J. et al., A comprehensive set of sequence analysis programs for the VAX, Nucleic Acids Research, 12(1):387-(1984).
Eddy, S. R. 1996. Hidden Markov models. *Cur Opin Struct Bio.* 6:361-5.
Ellen, R. P. et al. 1972. M protein-associated adherence of *Streptococcus pyogenes* to epithelial surfaces: prerequisite for virulence. *Infect Immun.* 5:826-830.
Eng, J. K. et al. 1994. An approach to correlate tandem mass-spectral data of peptides with amino-acid-sequences in a protein database. *Am Soc Mass Spectrometry.* 5:976-89.
Erdile et al. 1993. Role of attached lipid in immunogenicity of *Borrelia burgdorferi* OspA. *Infect. Immun.* Jan.;61(1):81-90.
Felgner, et. al., Proc. Natl. Acad. Sci. U.S.A., 1987, 84:7413-7417.
Felgner and Ringold, Science, 1989, 337:387-388.
Fischetti, V. A. et al. 1990. Conservation of a hexapeptide sequence in the anchor region of surface proteins from gram-positive cocci. *Mol Microbiol.* 4:1603-5.
Fletcher, et al., 2004, Vaccine Potential of the *Neisseria meningitidis* 2086 Lipoprotein, Infection and Immunity, vol. 72, No. 4, pp. 2088-2100.
Fogg, G. C. et al. 1997. Constitutive expression of fibronectin binding in *Streptococcus pyogenes* as a result of anaerobic activation of *rofA*. *J Bacteriol.* 179:6172-80.
Foster, T. J. et al. 1998. Surface protein adhesins of *Staphylococcus aureus. Trends Microbiol.* 6:484-488.
Fraser C. M. et al. 1997. *Nature.* 390:580-591.
Gentz et al., Bioassay for trans-activation using purified human immunodeficiency virus *tat*-encoded protein: trans-activation requires mRNA synthesis. *Proc. Natl. Acad. Sci.*, 86:821-24 (1989).
Goldschneider, I. et al. 1969. Human immunity to the meningococcus. I. The role of humoral antibodies. *Journal of Experimental Medicine* 129(6):1307-26.
Goldschneider, I. et al. 1969. Human immunity to the meningococcus. II. Development of natural immunity. *Journal of Experimental Medicine* 129(6):1327-48.
Gomez et al. 1994. Nucleotide The *Bacillus subtilis* lipoprotein LpIA causes cell lysis when expressed in *Escherichia coli. Microbiology.* Aug.;140 ( Pt 8):1839-45.
Gotschlich, E. C. et al. 1969. Human immunity to the meningococcus. IV. Immunogenicity of group A and group C meningococcal polysaccharides in human volunteers. *Journal of Experimental Medicine* 129(6):1367-84.
Gotschlich, E. C. et al. 1969. Human immunity to the meningococcus. V. The effect of immunization with meningococcal group C polysaccharide on the carrier state. *Journal of Experimental Medicine* 129(6):1385-95.
Graham, EMBO J., 1984, 3:2917.
Graham et al., *J. Gen. Virol.*, 1977, 36:59-72.
Green, B.A. et al. 1991. The e (P4) Outer Membrane Protein of *Haemophilus influenzae*: Biologic Activity of Anti-e Serum and Cloning and Sequencing of the Structural Gene. *Infect. Immun.* 59:3191-3198.
Hacker, J. et al. 1997. Pathogenicity islands of virulent bacteria: structure, function and impact on microbial evolution. *Mol Microbiol.* 23:1089-97.
Hanski, E. et al. 1992. Expression of protein F, the fibronectin-binding protein of *Streptococcus pyogenes* JRS4, in heterologous streptococcal and enterococcal strains promotes their adherence to respiratory epithelial cells. *Infect Immun.* 60:5119-5125.
Hanski, E. et al. 1992. Protein F, a fibronectin-binding protein, is an adhesion of the group A *Streptococcus Streptococcus pyogenes*. Proc Natl Acad Sci., USA. 89:6172-76.
Hansson et al. 1995. Expression of truncated and full-length forms of the Lyme disease Borrelia outer surface protein A in *Escherichia coli. Protein Expr. Purif.* Feb.; 6(1):15-24.
Hayashi et al. 1990. Lipoproteins in bacteria. *J. Bioenerg. Biomembr.* Jun.; 22(3):451-71.
Hernandez-Sanchez, J. et al. 1998. lambda bar minigene-mediated inhibition of protein synthesis involves accumulation of peptidyl-tRNA and starvation for tRNA. *EMBO Journal.* 17:3758-65.
Hornyik, Petidatri. Neurosurg., 21:189-1991, 1994 (abstract).

(56) References Cited

OTHER PUBLICATIONS

Huang, T. T. et al. 1989. The streptokinase gene of group A streptococci: cloning, expression in *Escherichia coli*, and sequence analysis. *Mol Microbiol*. 3:197-205.
Hynes, W. L. et al. 1995. Analysis of a second bacteriophage hyaluronidase gene from *Streptococcus pyogenes*: evidence for a third hyaluronidase involved in extracellular enzymatic activity. *Infect Immun*. 63:3015-20.
Hynes, W. L. et al. 2000. The extracellular hyaluronidase gene (*hylA*) of *Streptococcus pyogenes*. *FEMS Microbiol Lett*. 184:109-12.
Isberg, R. R. et al. 1994. Binding and internalization of microorganisms by integrin receptors. *Trends Microbio*. 2:10-4.
Jones, K. F. et al. 1988. The importance of the location of antibody binding on the M6 protein for opsonization and phagocytosis of group A M6 streptococci. *J Exp Med*. 167:1114-23.
Kafri, et al., *J. Virol.*, 1999, 73: 576-584.
Kaplitt et al., *Molec. Cell. Neurosci.*, 1991, 2:320-330.
Kihlberg, B. M. et al. 1999. Protein H, an antiphagocytic surface protein in *Streptococcus pyogenes*. *Infect Immun*. 67:1708-14.
Klein et al. 1988. Distinctive properties of signal sequences from bacterial lipoproteins. *Protein Eng*. Apr.; 2(1):15-20.
Koebnik, R. 1995. Proposal for a peptidoglycan-associating alpha-helical motif in the C-terminal regions of some bacterial cell-surface proteins [letter; comment]. *Molecular Microbiology*. 16:1269-70.
Kohler and Milstein, 1975, *Nature* 256:495-497.
Kuipers, O. P., et al. 1991. Improved site-directed mutagenesis method using PCR. *Nucleic Acids Res*. 19:4558.
Kuo et al., *Blood*, 1993, 82:845-852.
Kyte, J. et al. 1982. A simple method for displaying the hydropathic character of a protein. *Journal of Molecular Biology* 157:105-132.
Landt, O. et al. 1990. A general method for rapid site-directed mutagenesis using the polymerase chain reaction. *Gene* 96:125-128.
La Salle et al., *Science*, 1993, 259:988-990.
Lebkowski et al., *Mol. Cell. Biol.*, 1988, 8:3988-3996.
Levrero et al., *Gene*, 1991, 101:195-202.
Liu et al., 1987, *Proc. Natl. Acad. Sci. USA* 84:3439-3443.
Loessner, M. J. et al. 1999. Evidence for a holin-like protein gene fully embedded out of frame in the endolysin gene of *Staphylococcus aureus* bacteriophage 187. *J Bacteriol*. 181:4452-60.
Lukashin, A. V. et al. 1998. GeneMark.hmm: new solutions for gene finding. *Nucleic Acids Res*. 26:1107-15.
Lukomski, S. et al. 1999. Extracellular cysteine protease produced by *Streptococcus pyogenes* participates in the pathogenesis of invasive skin infection and dissemination in mice. *Infect Immun*. 67:1779-88.
Lunn et al. 1987. Effects of prolipoprotein signal peptide mutations on secretion of hybrid prolipo-beta-lactamase in *Escherichia coli*. *J. Biol. Chem*. Jun. 15;262(17):8318-24.
Machy, et al., *Proc. Natl. Acad. Sci. U.S.A.*, 1988, 85:8027-8031.
Madore, D. V. 1998. Characterization of immune response as an indicator of *Haemophilus influenzae* type b vaccine efficacy. *Pediatr Infect Dis J*. 17:S207-10.
Mann et al., *Cell*, 1983, 33:153-159.
Markowitz et al., *J. Virol*, 1988, 62:1120-1124.
Martin et al., 1985, Highly Conserved *Neisseria meningitidis* Surface Protein Confers Protection Against Experimental Injection, Journal of Experimental Medicine, vol. 185, No. 7, pp. 1173-1183.
Matsuka, Y. V. et al. 1999. Fibrinogen cleavage by the *Streptococcus pyogenes* extracellular cysteine protease and generation of antibodies that inhibit enzyme proteolytic activity. *Infect Immun*. 67:4326-33.
Mazmanian, S. K. et al. 1999. *Staphylococcus aureus* sortase, an enzyme that anchors surface proteins to the cell wall. *Science*. 285:760-3.
McAtee, C. P. et al. 1998. Identification of potential diagnostic and vaccine candidates of *Helicobacter pylori* by "proteome" technologies. *Helicobacter*. 3:163-9.
McAtee, C. P. et al.. 1998. Identification of potential diagnostic and vaccine candidates of *Helicobacter pylori* by two-dimensional gel electrophoresis, sequence analysis, and serum profiling. *Clin Diagn Lab Immunol*. 5:537-42.
McAtee, C. P. et al.. 1998. Characterization of a *Helicobacter pylori* vaccine candidate by proteome techniques. *J Chromatogr B Biomed Sci Appl*. 714:325-33.
McCormick, *BioTechnology*, 1985, 3:689.
Mejlhede, N. et al. 1999. Ribosomal-1 frameshifting during decoding of *Bacillus subtilis* cdd occurs at the sequence CGA AAG. *J. Bacteriol*. 181:2930-7.
Miller and Rosman, *Bio Techniques*, 1992, 7:980-990.
Mir et al., *C.P. Acad. Sci.*, 1988, 321:893.
Molinari, G. et al. 1997. The fibronectin-binding protein of *Streptococcus pyogenes*, SfbI, is involved in the internalization of group A streptococci by epithelial cells. *Infect Immun*. 65:1357-63.
Morrison et al., 1984, *Proc. Natl. Acad. Sci. USA* 81:6851-6855.
Mountzouros, K. T. et al. 2000. Detection of complement-mediated antibody-dependent bactericidal activity in a fluorescence-based serum bactericidal assay for group B *Neisseria meningitidis*. *J. Clin. Microbiol*. 38(8):2878-2884.
Nakai, K. et al. 1991. Expert system for predicting protein localization sites in gram-negative bacteria. *Proteins*. 11:95-110.
Naldini, Curr. Opin. Biotechnol., 1998, 9:457-63.
Navarre, W. W. et al. 1999. Surface proteins of gram-positive bacteria and mechanisms of their targeting to the cell wall envelope. *Microbiol Mol Biol Rev*. 63:174-229.
Nielsen, H., J. Engelbrecht, S. Brunak, and G. von Heijne. 1997. Identification of prokaryotic and eukaryotic signal peptides and prediction of their cleavage sites. *Protein Engineering*. 10:1-6.
Nizet, V. et al. 2000. Genetic locus for streptolysin S production by group A *Streptococcus*. *Infect Immun*. 68:4245-54.
Nordstrand, A. et al. 2000. Allele substitution of the streptokinase gene reduces the nephritogenic capacity of group A streptococcal strain NZ131. *Infect Immun*. 68:1019-25.
Olmsted, S. B. et al. 1993. High-resolution visualization by field emission scanning electron microscopy of *Enterococcus faecalis* surface proteins encoded by the pheromone-inducible conjugative plasmid pCF10. *J Bacteriol*. 175:6229-37.
Oudega et al., A lipoprotein signal peptide plus a cysteine residue at the amino-terminal end of the periplasmic protein β-lactamase is sufficient for its lipid modification, processing and membrane localization in *Escherichia coli*, FEMS Microbiol Lett. 108:353-360 (1993).
Oudega et al., *Escherichia coli* SecB, SecA, and SecY proteins are required for expression and membrane insertion of the bacteriocin release protein, a small lipoprotein. *J. of Bacter*. March;175(5):1 543-7, 1993.
Park, J. et al. 1998. DIVCLUS: an automatic method in the GEANFAMMER package that finds homologous domains in single- and multi-domain proteins. *Bioinformatics*. 14:144-50.
Parkhill, J. et al. 2000. Complete DNA sequence of a serogroup A strain of *Neisseria meningitidis* Z2491 [see comments]. *Nature*. 404:502-6.
Perrett, K. P. et al., 2005. "Towards an improved serogroup B *Neisseria meningitidis* vaccine", Expert Opinion on Biological Therapy, 5(12):1611-1625.
Phillips, A. 2001. J. Pharm. Pharmacology 53:1169-1174.
Pierschbacher, M. D. et al. 1987. Influence of stereochemistry of the sequence Arg-Gly-Asp-Xaa on binding specificity in cell adhesion. *J Biol Chem*. 262:17294-8.
Pizza, M. et al. 2000. Identification of vaccine candidates against serogroup B meningococcus by whole-genome sequencing. *Science* 287(5459):1816-20.
Podbielski, A. et al. 1995. The group A streptococcal virR49 gene controls expression of four structural vir regulon genes. *Infect Immun*. 63:9-20.
Pollitt et al. 1986. Effect of amino acid substitutions at the signal peptide cleavage site of the *Escherichia coli* major outer membrane lipoprotein. *J. Biol. Chem*. Feb. 5; 261(4):1835-7.
Poolman, J. T. 1996. Bacterial outer membrane protein vaccines. The meningococcal example. *Advances in Experimental Medicine & Biology* 397:73-7.
Proft, T. et al. 1999. Identification and Characterization of Novel Superantigens from *Streptococcus pyogenes*. *J Exp Med*. 189:89-102.

(56) References Cited

OTHER PUBLICATIONS

Pugsley, A. P. 1993. The complete general secretory pathway in gram-negative bacteria. *Microbiol Rev.* 57:50-108.
Quinn, A. et al. 1998. Immunological relationship between the class I epitope of streptococcal M protein and myosin. *Infect Immun.* 66:4418-24.
Reda, K. B. et al. 1996. Phylogenetic distribution of streptococcal superantigen SSA allelic variants provides evidence for horizontal transfer of ssa within *Streptococcus pyogenes. Infect Immun.* 64:1161-5.
Sahagan et al., 1986, *J. Immunol.* 137:1066-1074.
Salzberg, S. L. et al. 1998. Microbial gene identification using interpolated Markov models. Nucleic Acids Res. 26:544-8.
Samulski et al., J. Virol., 1987, 61:3096-3101.
Samulski et al., *J. Virol.*, 1989, 63:3822-3828.
Sankaran et al. 1995. Modification of bacterial lipoproteins. *Methods Enzymol.* 250:683-97.
Saukkonen, 1987, *Microbial Pathogenesis* 3(4):261-7.
Sedegah et al. 1994. *Immunology.* 91, 9866-9870.
Sedegah, M. et al., 2000. Improving protective immunity induced by DNA-based immunization: priming with antigen and gm-csf-encoding plasmid dna and boosting with antigen-expressing recombninant poxvirus1,2. Journal of Immunology. 164:5905-5912.
Snapper, C.M. et al., IL-3 and granulocyte-macrophage colony-stimulating factor strongly induce Ig secretion by sort-purified murine B cells activated through the membrane Ig, but not the CD40, signaling pathway. The Journal of Immun. 154:5842-50 (1995).
Sonnenberg, M. G. et al. 1997. Definition of *Mycobacterium tuberculosis* culture filtrate proteins by two-dimensional polyacrylamide gel electrophoresis, N-terminal amino acid sequencing, and electrospray mass spectrometry. *Infect Immun.* 65:4515-24.
Sonnhammer, E. L. et al. 1997. Pfam: a comprehensive database of protein domain families based on seed alignments. *Proteins.* 28:405-20.
Stevens, D. L. 1995. Streptococcal toxic-shock syndrome: spectrum of disease, pathogenesis, and new concepts in treatment. *Emerg Infect Dis.* 1:69-78.
Stockbauer, K. E. et al. 1999. A natural variant of the cysteine protease virulence factor of group A *Streptococcus* with an arginine-glycine-aspartic acid (RGD) motif preferentially binds human integrins alphavbeta3 and alphaIIbbeta3 *Proc Natl Acad Sci., USA.* 96:242-7.
Stratford-Perricaudet et al., *J. Clin. Invest.*, 1992, 90:626-630.
Sun et al., 1987, *Proc. Natl. Acad. Sci. USA* 84:214-218.
Tarkka et al., Micrb. Pathogen., 6:327-335, May 1989.
Tettelin, H. et al. 2000. Complete genome sequence of *Neisseria meningitidis* serogroup B strain MC58. *Science* 287(5459):1809-15.
Ton-That, H., G. Liu, S. K. Mazmanian, K. F. Faull, and O. Schneewind. 1999. Purification and characterization of sortase, the transpeptidase that cleaves surface proteins of *Staphylococcus aureus* at the LPXTG motif. *Proc Natl Acad Sci U S A.* 96:12424-12429.
Ulmer et al., *Science*, 1993, 259:1745-1748.
Wahl et al., 1983, *J. Nucl. Med.* 24:316-325.
Weldingh, K. et al. 1998. Two-dimensional electrophoresis for analysis of *Mycobacterium tuberculosis* culture filtrate and purification and characterization of six novel proteins. *Infect Immun.* 66:3492-500.
Williams et al., Proc. Natl. Acad. Sci. USA, 1991, 88:2726-2730.
Wolff et al. 1990. *Science.* 247, 1465-1468.
Wu and Wu, *J. Biol. Chem.*, 1987, 262:4429-4432.
Wu and Wu, *J. Biol. Chem.*, 1988, 263:14621-14624.
Yakushi et al. 1997. Lethality of the covalent linkage between mislocalized major outer membrane lipoprotein and the peptidoglycan of *Escherichia coli. J. Bacteriol.* May; 179(9):2857-62.
Yakushi et al. 2000. A new ABC transporter mediating the detachment of lipid modified proteins from membranes. *Nat Cell Biol.* Apr.;2(4):212-18.
Yutsudo, T. et al. 1994. The gene encoding a new mitogenic factor in a *Streptococcus pyogenes* strain is distributed only in group A streptococci. *Infection and Immunity.* 62:4000-4004.
Zagursky, R.J. et al. 2001. Bioinformatics: Use in Bacterial Vaccine Discovery. *BioTechniques.* 31:636-659.
Zavascki et al., J. Clin. Microbiol., 44:2666-2668, 2006.
Zufferey, et al., *J. Virol.*, 1998, 72:9873-80.
Annex to Form PCT/ISA/206, Communication Relating to the Results of the Partial International Search, Apr. 2007.
USPTO Final Office Action, mailed Dec. 10, 2008, In re of Application of: Gary Warren Zlotnick et al., U.S. Appl. No. 10/492,427, filed Oct. 7, 2004, For: Novel Immunogenic Compositions for the Prevention and Treatment of Meningococcal Disease, Confirmation No. 8010, Customer No. 25291.
USPTO Final Office Action, Mailed Nov. 19, 2008, In re of Application of: Gary W. Zlotnick et al., U.S. Appl. No. 10/652,870, filed Sep. 2, 2003, For: Novel Immunogenic Compositions for the Prevention and Treatment of Meningococcal Disease, Confirmation No. 1480, Customer No. 25291.
USPTO Updated Filing Receipt, Mailed May 4, 2009, In re of Application of: Zlotnick et al., U.S. Appl. No. 12/214,043, filed Jun. 16, 2008, For: Novel Immunogenic Compositions for the Prevention and Treatment of Meningococcal Disease, Confirmation No. 9501, Customer No. 25291.
Current Protocols in Molecular Biology, 1995, F.M. Ausubel et al., eds., John Wiley & Sons, Inc., sections 2.10 and 6.3-6.4.
The Illustrated Steadman's Medical Dictionary, 24th Edition, Williams & Wilkins, Baltimore, p. 707, 1982.
The Webster's II *New Riverside University Dictionary*, The Riverside Publishing Company, p. 933, 1984.
Chao, H. et al., "Endocarditis due to *Neisseria sicca*: Report of One Case," 1997, Dept. of Pediatrics, Chang Gung Children's Hospital, vol. 38, pp. 229-231.
Ellis, R. W., "New Technologies for Making Vaccines," 1988, Vaccines, (eds) Plotkin et al.; W.B. Sauders Company, Philadephia, Chapter 29, pp. 568-575.
Guzman, L-M et al., "Tight Regulation, Modulation, and High-Level Expression by Vectors Containing the Arabinose $P_{BAD}$ Promoter," 1995, Journal of Bacteriology, vol. 177, pp. 4121-4130.
Snapper, Clifford et al., "Bacterial Lipoproteins May Substitute for Cytokines in the Humoral Immune Response to T Cell-Independent Type II antigens," 1995, Journal of Immunology, vol. 155(12), pp. 5582-5589.
Wilson, James M. et al., "Hepatocyte-directed Gene Transfer in Vivo Leads to Transient Improvement of Hypercholesterolemia in Low Density Lipoprotein receptor-deficient Rabbits," 1992, Journal of Biological Chemistry, vol. 267, pp. 963-967.
Database Geneseq Online Jan. 29, 2004, "*Neisseria meningitides* ORF2086 protein-encoding gene SeqID61", (AAY75530 and AAZ54292-NT).
International Search Report for PCT/US2007/026238, date of mailing of the ISR Feb. 23, 2009.
Parkhill, J., "Campylobacter jejuni genome sequence at the Sanger Centre", (May 8, 1998), available at: http://www.bio.net/bionet/mm/bionews/1998-May/00442.html.
Patentees' Further Submission Under Rule 116 EPC in Opposition against Novartis EP 1 645 631 submitted Oct. 14, 2011.
Patentees' Response to Opposition against Novartis EP 1 645 631 submitted May 8, 2009.
Patentees' Submissions Under Rule 116 EPC in Opposition against Novartis EP 1 645 631 submitted Sep. 13, 2011.
Pettersson, A., et al., "The meningococcal lactoferrin receptor", IPNC Abstract (1998).
Pettersson, A., et al., "Vaccine potential of the *Neisseria meningitidis* lactoferrin-binding proteins LbpA and LbpB", Vaccine, 24(17):3545-3557 (2006).
Pizza, M.G., et al., "Preparation of Meningococcal Antigens" (Feb. 2, 2005), available at: http://cordis.europa.eu/search/index.cfm?fuseaction=result.document&RSLANG=EN&RSRCN=7461241&q=.
Poolman, J.T., "Development of a Meningococcal Vaccine", Infectious Agents and Disease, 4(1):13-28 (1995).

(56) References Cited

OTHER PUBLICATIONS

Preliminary Opinion of the Opposition Division in Opposition against Novartis EP 1 645 631 dated Jun. 24, 2011.
Progress through the Sanger Institute FTP Server, submitted in Opposition Proceedings against Novartis EP 1 645 631 on May 8, 2009.
PSORT analysis of 200 of the sequences disclosed in PCT/US99/09346, submitted in Opposition Proceedings against Novartis EP 1 645 631 on May 25, 2010.
PSORT analysis of SEQ ID Nos. 4 and 6, and of 'Contig295' 300mer, submitted in Opposition Proceedings against Novartis EP 1 645 631 on May 8, 2009.
PSORT prediction result for SEQ ID No. 2, submitted in Opposition Proceedings against Novartis EP 1 645 631 on May 25, 2010.
Rinaudo, C.D., et al., "Vaccinology in the genome era", The Journal of Clinical Investigation, 119(9):2515-2525 (2009).
Romero, J.D., et al., "Current Status of Meningococcal Group B Vaccine Candidates: Capsular of Noncapsular?", Clinical Microbiology Reviews, 7(4):559-575 (1994).
Ross, B.C.., et al., "Identification of vaccine candidate antigens from a genomic analysis of Porphyromonas gingivalis", Vaccine, 19:4135-4142 (2001).
Sanger Centre FTP files [online] URL: ftp://ftp.sanger.ac.uk/pub/pathogens/nm/, generated on Jul. 23, 2008.
Sanger Centre's "Projects" website as of Dec. 12, 1997 as retrievable via http://web.archive.org, printed on Jul. 23, 2008.
Sequence for "Putative Lipoprotein [*Neisseria miningitidis* Z2491]", NCBI Reference Sequence: YP_002342062.1 (May 6, 2009).
Serruto, D., et al., "Genome-based approaches to develop vaccines against bacterial pathogens", Vaccine, 27:3245-3250 (2009).
Smith, C.J., et al., "Nucleotide Sequence Determination and Genetic Analysis of the Bacteroides Plasmid, pBI143", Plasmid, 34(3):211-222 (1995).
Supplementary Declaration by Dr. Julian Parkhill submitted in Opposition Proceedings against Novartis EP 1 645 631 on May 25, 2010.
Supplementary Submission in Opposition Proceedings against Novartis EP 1 645 631 submitted May 25, 2010.
Sutcliffe, I.C., et al., "Lipoproteins of Gram-Positive Bacteria", Journal of Bacteriology, 177(5):1123-1128 (1995).
Sworn Statement from Dr. Rino Rappuoli submitted in Opposition Prceedings against Novartis EP 1 645 631 on Oct. 14, 2011.
Telford, J.L., et al., "Chapter 1: Genomics and Proteomics in Vaccine Design", New Bacterial Vaccines, Kleweur Academic/Plenum Publishers, USA, pp. 1-11 (2003).
Van Der Ley, P., et al., "Construction of *Neisseria meningitidis* strains carrying multiple chromosomal copies of the por A gene for use in the production of a multivalent outer membrane vesicle vaccine", Vaccine, 13(4):401-407 (1995).
Welsch, J.A., et al., "Protective Activity of Monoclonal Antibodies to Genome-Derived Neisserial Antigen 1870, a *Neisseria meningitidis* Candidate Vaccine", The Journal of Immunology, 172:5606-5615 (2004).
Woods, J.P., "Resistance to Meningococcemia Apparently Conferred by Anti-H.8 Monoclonal Antibody Is Due to Contaminating Endotoxin and Not to Specific Immunoprotection", Infection and Immunity, 55(8): 1927-1928 (1987).
Zollinger, W.D., "New and Improved Vaccines Against Meningococcal Disease", New Generation Vaccines, 2nd Edition, Myron M. Levine, et al. eds., Marcel Dekker, Inc., New York, NY, pp. 469-488 (1997).
GenBank No. EF108319.1, O'Leary, M. M. et al., *Neisseria meningitidis* strain NM452 FHBP/GNA1870 variant (GNA1870) gene, complete cds, Nov. 8, 2006, accessed Sep. 5, 2012.
Pannekoek et al, "Construction of recombinant neisserial Hsp60 proteins and mapping of antigenic domains", Molecular Microbiology 15(2):277-285 (1995).
Poolman et al, "Colony variants of *Neisseria meningitidis* strain 2996 (B-2b:P1.2): influence of class-5 outer membrane proteins and lipopolysaccharides", J Med Microbiol 19(2):203-209 (1985).
Aasel, A., et al., Abstract from the 11th International Pathogenic *Neisseria* Conference, Nice, France, pp. 37-38 (Nov. 1-6, 1998).
Altschul, S.F., et al., "Gapped BLAST and PSI-BLAST: a new generation of protein database search programs", Nucleic Acids Research, 25(17):3389-3402 (1997).
Barbour, A.G., et al., "New Tricks of Tick-Borne Pathogen", Nature, 390:553 & 555 (1997).
Bernfield, L, et al., "Identification of a novel vaccine candidate for group B *Neisseria meningitidis* ", Abstract from the Thirteenth International Pathogenic *Neisseria* Conference, Oslo, Norway, p. 116 (Sep. 1-6, 2002).
Bjune, G., et al., "Effect of outer membrane vesicle vaccine against group B meningococcal disease in Norway", The Lancet, 338(8775):1093-1096 (1991).
Boslego, J. W., et al., "Chapter 17: Gonorrhea Vaccines", Vaccines and Immunotherapy, S.J. Cryz, Jr. ed., Pergamon Press, pp. 211-224 (1991).
Cannon, J.G., "Conserved Lipoproteins of Pathogenic *Neisseria* Species Bearing the H.8 Epitope: Lipid-Modified Azurin and H.8 Outer Membrane Protein", Clinical Microbiology Reviews, 2:S1-S4 (1989).
Cantini, F., et al., "Solution Structure of the Immunodominant Domain of Protective Antigen GNA1870 of *Neisseria meningitidis* ", Journal of Biological Chemistry, 281(11):7220-7227 (2006).
Chen, H., et al., "Determination of the optimal aligned spacing between the Shine-Dalgarno sequence and the translation initiation codon of *Escherichia coli* mRNAs", Nucleic Acids Research, 22(23):4953-4957 (1994).
Curriculum Vitae of Professor Paul M. Dunman, Ph.D., submitted in Opposition Proceedings against Novartis EP 1 645 631 on Sep. 14, 2011.
Database EMBL [Online] EBI, Kohara, Y., "*Caenorhabditis elegans* cDNA clone yk26f2: 5' end, single read," Database accession No. D35881 (Aug. 13, 1994).
Declaration by Dr. Julian Parkhill, submitted in Opposition Proceedings against Novartis EP 1 645 631 on Jul. 23, 2008.
Declaration by Professor Paul Dunman, submitted in Opposition Proceedings against Novartis EP 1 645 631 on Sep. 14, 2011.
Declaration of Dr. Ellen Murphy, submitted in Opposition Proceedings against Novartis EP 1 645 631 on Sep. 14, 2011.
Declaration of Emilio A. Emini, Ph.D., submitted in Opposition Proceedings against Novartis EP 1 645 631 on Nov. 3, 2011.
Definition of "epitope" from Henderson's Dictionary of Biological Terms, Eleventh Edition, Eleanor Lawrence ed., pp. 37, 184 and cover pages (1997).
Delgado, M., et al., "Lipoprotein NMB0928 from *Neisseria meningitidis* serogroup B as a novel vaccine candidate", Vaccine 25:8420-8431 (2007).
Dempsey, J.A.F., et al., "The Physical Map of the Chromosome of a Serogroup A Strain of *Neisseria meningitidis* Shows Complex Rearrangements Relative to the Chromosomes of the Two Mapped Strains of the Closely Related Species *N. gonorrhoeae*", Journal of Bacteriology, 177(22):6390-6400 (1995).
EP Appln. No. 07075161.5 Response to Communication submitted Oct. 28, 2009.
Farley, J., et al., "Characterization, cloning and expression of different subfamilies of the ORF 2086 gene from *Neisseria meningitidis*", Abstract from the Thirteenth International Pathogenic *Neisseria* Conference, Oslo, Norway, p. 124 (Sep. 1-6, 2002).
Feavers, I.M., et al., "Meningococcal protein antigens and vaccines", Vaccine, 275:B42-B50 (2009).
Final Wirtten Submission in Preparation of Oral Proceedings in Opposition against Novartis EP 1 645 631 submitted Sep. 14, 2011.
Fleischmann, R.D, et al., "Whole-Genome Random Sequencing and Assembly of *Haemophilus influenzae* Rd", Science, 269:496-512 (1995).
Fontana, M.R., et al., "A genomic approach to identify vaccine candidates against gonococcus", Abstract from the Thirteenth International Pathogenic *Neisseria* Conference, Oslo, Norway, p. 248 (Sep. 1-6, 2002).
Giuliani, M.M., et al., "The Region Comprising Amino Acids 100 to 255 of *Neisseria meningitidis* Lipoprotein GNA 1870 Elicits Bactericidal Antibodies", Infection and Immunity, 73(2):1151-1160 (2005).

(56) References Cited

OTHER PUBLICATIONS

Giuliani, M.M., et al., "A universal vaccine for serogroup B meningococcus", Proc. Natl. Acad. Sci., 103 (29):10834-10839 (2006).
Gold, L., et al., "Chapter 78: Translation Initiation", *Escherichia coli* and *Salmonella typhimurium*: Cellular and Molecular Biology, F.C. Neidhardt ed., vol. 2, pp. 1302-1307 (1987).
Grandi, G., et al., "Reverse vaccinology: a critical analysis", Encyclopedia of Genetics, Genomics, Proteomics and Bioinformatics, pp. 1320-1330 (2005).
Greenspan, N.S., et al., "Defining epitopes: It's not as easy as it seems", Nature Biotechnology, 17:936-937 (1999).
Hung, M.C., et al., "The *Neisseria meningitidis* Macrophage Infectivity Potentiator Protein Induces Cross-Strain Serum Bactericidal Activity and Is a Potential Serogroup B Vaccine Candidate", Infection and Immunity, 79 (9):3784-3791 (2011).
Interlocutory Decision of the Opposition Division in Opposition against Novartis EP 1 645 631 dated May 21, 2012.
Jackson, J.W., et al., U.S. Appl. No. 60/098,685, filed Sep. 1, 1998.
Jiang, H.Q., et al., "Broad vaccine coverage predicted for a bivalent recombinant factor H binding protein based vaccine to prevent serogroup B meningococcal disease", Vaccine, 28:6086-6093 (2010).
Johnson, A.S., et al., "Analysis of the human Ig isotype response to lactoferrin binding protein A from *Neisseria meningitidis* ", FEMS Immunology and Medical Microbiology, 25(4):349-354 (1999).
JVCI-CMR website showing Z2491 Sanger sequence (http://cmr.jvci.org/tigr-scripts/CMR/shared/Genomes.cgi and links) printed on Jul. 1, 2010.
Masignani, V., et al., "Vaccination against *Neisseria meningitidis* Using Three Variants of the Lipoprotein GNA1870", J Exp. Med., 197(6):789-799 (2003).
McGuinness, B.T., et al., "Class 1 outer membrane protein of *Neisseria meningitidis*: epitope analysis of the antigenic diversity between strains, implications for subtype definition and molecular epidemiology", Molecular Microbiology, 7(4):505-514 (1993).
Milagres, L.G., et al., "Specificity of Bactericidal Antibody Response to Serogroup B Meningococcal Strains in Brazilian Children after Immunization with an Outer Membrane Vaccine", Infection and Immunity, 66(10):4755-4761 (1998).
Minutes of Oral Proceedings in Opposition against Novartis EP 1 645 631 dated May 18, 2012.
Moreno, C., et al., "Immunity and Protection of Mice Against *Neisseria meningitidis* Group B by Vaccination, Using Polysaccharide Complexed with Outer Membrane Proteins: A Comparison with Purified B Polysaccharide", Infection and Immunity, 47(2):527-533 (1985).
Morley, S.L., et al., "Vaccine prevention of meningococcal disease, coming soon?", Vaccine, 20:666-687 (2002).
Moxon, R.E., "Applications of molecular microbiology to vaccinology", The Lancet, 350(9086):1240-1244 (1997).
Munkley, A., et al., "Blocking of bactericidal killing of *Neisseria meningitidis* by antibodies directed against class 4 outer membrane protein", Microbial Pathogenesis, 11:447-452 (1991).
Murphy, E., et al., "Sequence Diversity of the Factor H Binding Protein Vaccine Candidate in Epidemiologically Relevant Strains of Serogroup B *Neisseria meningitidis*", The Journal of Infectious Diseases, 200:379-389 (2009).
Nassif, X., "A Furtive Pathogen Revealed", Science, 287:1767-1768 (2000).
*Neisseria gonorrhoeae* Strain FA1090 Complete Genomic Sequence; Submitted (Sep. 26, 2000) Department of Chemistry and Biochemistry, The University of Oklahoma; Genbank Accession gono AE004969.
"New Phase II data show Novartis investigational Meningitis B vaccine may also protect infants six months and older", Novartis Media Release (Oct. 9, 2008).
Notice of Opposition against Novartis EP 1 645 631 submitted Jul. 23, 2008.
"Novartis submits Bexsero®, a multi-component meningococcal B vaccine, for regulatory review in Europe", Novartis Media Release (Dec. 23, 2010).
Opponent's Further Submission in Preparation of Oral Proceedings in Opposition against Novartis EP 1 645 631 submitted Nov. 3, 2011.

\* cited by examiner

Identification of Components in the Unadsorbed TMAE
Fraction: Reverse Phase Isolation of Peptides Enzymatic digestion of unadsorbed TMAE fraction followed by
reverse phase chromatography separation of peptides and
direct N-terminal sequencing

| Enzymatic Digest | Retention Time of Peptide (min) | Molecular Weight of Peptide (d) | N-term. ID |
|---|---|---|---|
| GluC (V8) | 6.716 | 2069.7 | P5163 |
| LysC | 13.800 | 3351.2 | P4431 |
| LysC | 13.800 | 3351.2 | P2086 |
| ArgC | 6.860 | 2278.9 | P5163 |

P4431
predicted mw 36,775

P2086
predicted mw 27,100

P5163
predicted mw 7,081

FIG. 1B

Identification of Components in the Unadsorbed
TMAE Fraction: LC-MS/MS

SDS-PAGE followed by gel excision, proteolytic digestion, and LC-MS/MS
analysis (Liquid Chromotography tandem Mass Spectrometry)

10-20% SDS-PAGE
Coomassie Stain

FIG. 8

```
          10                  20               30
1  CSSGGGG-----VAADIGAGLADALTAPLD    8529 nat.pro  (SEQ ID NO:13)
1  CSSGGGG-----VAADIGAGLADALTAPLD    2996 nat.pro  (SEQ ID NO:14)
1  CGSGGGGSGGGGVTADIGTGLADALTAPLD    1573 nat.pro  (SEQ ID NO:15)
              └─────┬─────┘
              5 amino acid repeat
```

Western Blot Reactivity of rLP2086 Mouse Antisera to P2086
Subfamily B *N. meningitidis* Whole Cell Lysates 1  2  3  4  5  6  7  8  9  10  11

198
115
93
49.8
35.8    ← Native P2086
29.2
21.3
6.4

1 - Molecular Weight Marker (kDa)
2 – M97 251985
3 – CDC937
4 - 6940
5 – M97 251926
6 – CDC1573
7 - CDC1359
8 - CDC1658
9 - M97 252026
10 - M97 252029
11 - M982

Subfamily B P2086 cell lysates are all Group B *N. meningitidis*

FIG.17

IMMUNOGENIC COMPOSITIONS FOR THE PREVENTION AND TREATMENT OF MENINGOCOCCAL DISEASE

FIELD OF THE INVENTION

This application is related to provisional application No. 60/876,486, which is incorporated by reference in its entirety.

The present invention relates to Neisseria ORF2086 proteins (Subfamily A and Subfamily B), which may be isolated from bacterial strains such as those of Neisseria species, including strains of Neisseria meningitidis (serogroups A, B, C, D, W-135, X, Y, Z and 29E), Neisseria gonorrhoeae, and Neisseria lactamica, as well as immunogenic portions and/or biological equivalents of said proteins. The present invention also relates to antibodies that immunospecifically bind to said proteins, immunogenic portions and/or biological equivalents. Further, the present invention relates to isolated polynucleotides comprising nucleic acid sequences encoding any of the foregoing proteins, immunogenic portions, biological equivalents and/or antibodies. Additionally, the present invention relates to immunogenic compositions and their use in preventing, treating and/or diagnosing meningococcal infection caused by N. meningitidis, and in particular meningococcal disease caused by N. meningitidis serogroup B, as well as methods for preparing said compositions. This invention relates to both recombinant forms and forms isolated from a natural source, as well as both lipidated and non-lipidated forms.

BACKGROUND OF THE INVENTION

Meningococcal meningitis is a devastating disease that can kill children and young adults within hours despite the availability of antibiotics. Pizza et al., 2000, Science 287:1816-1820. Meningitis is characterized as an inflammation of the meninges resulting in an intense headache, fever, loss of appetite, intolerance to light and sound, rigidity of muscles, especially in the neck, and in severe cases convulsions, vomiting and delirium leading to death. The symptoms of meningococcal meningitis appear suddenly and culminate in meningococcal septicemia with its characteristic hemorrhagic rash. A rapid diagnosis and immediate treatment with large doses of antibiotics is critical if there is to be any chance of survival. 2000. Bantam Medical Dictionary, Third Edition 302.

Meningococcal meningitis is caused by Neisseria meningitidis (the meningococcus), a Gram-negative, capsulated bacterium that has been classified into several pathogenic serogroups including A, B, C, D, W-135, X, Y, Z and 29E. Serogroup B strains of N. meningitidis are a major cause of meningococcal disease throughout the world. For example, it is reported in the medical literature that serogroup B is responsible for about 50% of bacterial meningitis in infants and children residing in the United States and Europe. No vaccine currently exists to prevent meningococcal disease caused by N. meningitidis serogroup B.

Developing an immunogenic composition for the prevention of serogroup B meningococcal disease has been a challenge to researchers since the work of Goldschneider et al. over thirty years ago. Goldschneider et al., 1969, J. Exp. Med. 129(6):1307-26; Goldschneider et al, 1969, J. Exp. Med. 129 (6):1327-48; Gotschlich et al., 1969, J. Exp. Med. 129(6): 1385-95; and Gotschlich et al., 1969, J. Exp. Med. 129(6): 1367-84. Unlike serogroup A disease, which virtually disappeared from North America after World War II, Achtman, M., 1995, Trends in Microbiology 3(5):186-92, disease caused by serogroup B and C organisms remains endemic throughout much of the economically developed world. The incidence of disease varies from <1/100,000 where endemic disease is rare to 200/100,000 in high risk populations during epidemics.

Vaccines based on polysaccharide conjugates have been developed against N. meningitidis serogroups A and C and appear to be effective in preventing disease. Currently, an immunogenic composition made of capsular polysaccharide from serogroups A, C, Y, & W-135 is available. Ambrosch et al., 1983, Immunogenicity and side-effects of a new tetravalent. Bulletin of the World Health Organization 61(2):317-23. However, this immunogenic composition elicits a T-cell independent immune response, is not effective in young children, and provides no coverage for serogroup B strains, which cause upwards of 50% of meningococcal disease.

Others have also attempted to develop immunogenic compositions using capsular polysaccharides. Recently, immunogenic compositions for serogroup C disease prepared by conjugating the serogroup C capsular material to proteins have been licensed for use in Europe. However, the serogroup B capsule may be unsuitable as a vaccine candidate because the capsule polysaccharide is composed of polysialic acid which bears a similarity to carbohydrate moieties on developing human neural tissues. This sugar moiety is recognized as a self-antigen and is thus poorly immunogenic in humans.

Outer membrane proteins (OMP's) have been developed as alternative vaccine antigens for serogroup B disease. Monoclonal antibody binding to the two variable regions of PorA defines the serosubtyping scheme for meningococci. PorA proteins thus serve as the serosubtyping antigens (Abdillahi et al., 1988, Microbial Pathogenesis 4(1):27-32) for meningococcal strains and are being actively investigated as components of a serogroup B immunogenic composition (Poolman, 1996, Adv. Exp. Med. Biol. 397:73-7), since they can elicit bactericidal antibodies (Saukkonen, 1987, Microbial Pathogenesis 3(4):261-7). Bactericidal antibodies are thought to be an indicator of protection and any new immunogenic composition candidate should elicit these functional antibodies.

Studies in humans as well as animals indicate that the serosubtyping antigen, PorA, elicits bactericidal antibodies. However, the immune response to Por A is generally serosubtype specific. In particular, serosubtyping data indicate that an immunogenic composition made of PorAs may require a PorA for each serosubtype to be covered by such an immunogenic composition, perhaps as many as six to nine. Therefore, 6-9 PorAs will be needed to cover 70-80% of serogroup B strains. Thus, the variable nature of this protein requires a multivalent vaccine composition to protect against a sufficient number of meningococcal serosubtype clinical isolates.

Developing an immunogenic composition for serogroup B meningococci has been so difficult that recently several groups have sequenced the genomes from strains representing both serogroups A and B to assist in identifying new immunogenic composition candidates. Tettelin, 2000, Science, 287(5459):1809-15; Pizza et al., 2000, Science 287: 1816-1820. Identifying new immunogenic composition candidates, even with the knowledge of the neisserial genome, is a challenging process for which adequate mathematical algorithms do not currently exist. In fact, a recent report indicates that despite identifying hundreds of open reading frames ("ORFs") containing theoretical membrane spanning domains, problems with expression, purification, and inducing surface reactive, and functionally active antibodies have led investigators to only seven candidates for a serogroup B meningococcal immunogenic composition. See Id. One of these was previously known.

Accordingly, there remains a need for immunogenic compositions that (1) elicit bactericidal antibodies to multiple neisserial strains; (2) react with the surface of multiple strains; (3) confer passive protection against a live challenge; and/or (4) prevent colonization.

SUMMARY OF THE INVENTION

An embodiment of the present invention provides a polynucleotide comprising: (a) a nucleotide sequence having at least about 95% sequence identity to any of the odd numbered sequences of SEQ ID NOS:1-11; or (b) a nucleotide sequence that encodes a polypeptide comprising an amino acid sequence having at least about 95% sequence identity to an amino acid sequence of any of the even numbered sequences of SEQ ID NOS:2-12.

A further embodiment of the present invention provides a vector comprising a polynucleotide of the present invention.

An even further embodiment of the present invention provides a recombinant cell comprising a vector of the present invention.

A still further embodiment of the present invention provides a polypeptide comprising: (a) an amino acid sequence having at least 95% sequence identity to any of the even numbered sequences of SEQ ID NOS:2-12; (b) an amino acid sequence that is encoded by a nucleotide sequence having at least 95% sequence identity to any of the odd numbered sequences of SEQ ID NOS:1-11; (c) at least one immunogenic portion of an amino acid sequence described in (a) or (b); or (d) at least one biological equivalent of an amino acid sequence described in (a) or (b) or immunogenic portion described in (c).

A still further embodiment of the present invention provides an antibody comprising any of: (a) a polypeptide that immunospecifically binds with a polypeptide comprising an amino acid sequence of any of even numbered SEQ ID NOS: 2-12; or (b) at least one immunogenic portion of the polypeptide described in (a); or (c) at least one biological equivalent of the polypeptide described in (a) or immunogenic fragment described in (b).

A still further embodiment of the present invention provides a composition comprising a polynucleotide, vector, recombinant cell, polypeptide or antibody of the present invention.

A still further embodiment of the present invention provides a composition comprising: (a) a first polynucleotide comprising a nucleotide sequence having at least about 95% sequence identity to any of the odd numbered sequences of SEQ ID NOS:1-5 or at least about 95% sequence identity to a nucleotide sequence that encodes an amino acid sequence of any of the even numbered sequences of SEQ ID NOS:2-6; and (b) a second polynucleotide comprising a nucleotide sequence having at least about 95% sequence identity to of any of the odd numbered sequences of SEQ ID NOS:7-11 or at least about 95% sequence identity to a nucleotide sequence that encodes the amino acid sequence of any of the even numbered sequences of SEQ ID NOS:8-12.

A still further embodiment of the present invention provides a composition comprising: (a) a first polypeptide comprising an amino acid sequence having at least about 95% sequence identity to any of the even numbered sequences of SEQ ID NOS:2-6; and (b) a second polypeptide comprising an amino acid sequence having at least about 95% sequence identity to any of the even numbered sequences of SEQ ID NOS:8-12.

A still further embodiment of the present invention provides a composition prepared by a process comprising: isolating and purifying from *Neisseria* species or recombinantly preparing any of: (a) a polypeptide comprising the amino acid sequence of any of even numbered SEQ ID NOS:2-12; (b) a polypeptide encoded by a polynucleotide comprising the nucleic acid sequence of any of odd numbered SEQ ID NOS: 1-11; (c) at least one immunogenic portion of the polypeptide described in (a) or (b); or (d) at least one biological equivalent of the polypeptide described in (a) or (b) or immunogenic fragment described in (c).

A still further embodiment of the present invention provides the use of a composition of the present invention in the preparation of a medicament for inducing an immune response in a mammal.

A still further embodiment of the present invention provides the use of a composition of the present invention in a medicament effective against bacterial meningitis in a mammal.

A still further embodiment of the present invention provides a method of preparing a composition comprising expressing in a host cell a nucleic acid sequence encoding any of the polypeptides described herein.

A still further embodiment of the present invention provides a method of preparing an antibody composition comprising recovering antibodies from an animal after introducing into the animal a composition comprising any of the proteins, immunogenic portions or biological equivalents described herein.

A still further embodiment of the present invention provides a method of inducing an immune response in a mammal comprising administering to the mammal an effective amount of one or more of the compositions of the present invention.

A still further embodiment of the present invention provides a method of preventing or treating bacterial meningitis in a mammal comprising administering to the mammal an effective amount of one or more of the compositions of the present invention.

BRIEF DESCRIPTION OF THE DRAWINGS

FIG. 1B depicts the results from the experiments from the identification of the two major proteins by analysis of TMAE Flow Through components by protease digestion and reverse Phase N-terminal sequencing.

FIG. 8 illustrates N-terminal regions of 2086 gene from various strains.

FIG. 17 is a Western Blot showing reactivity of rLP2086 mouse antisera to P2086 Subfamily B *N. meningitidis* whole cell lysates.

SEQUENCE SUMMARY

Figure 1A:
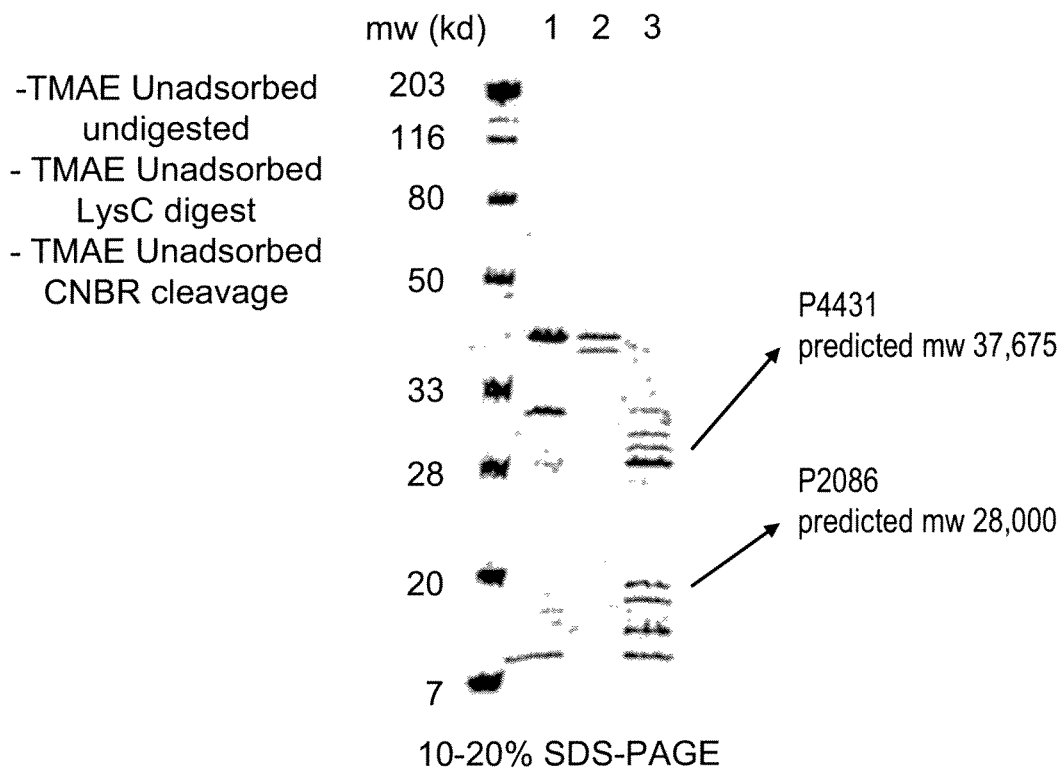
FIG. 1A depicts an SDS-PAGE gel that depicts the two major proteins of the protein fractions obtained from the experiments for identifying neisserial membrane protein extract that is capable of eliciting bactericidal antibodies against heterologous strains.

SEQ ID NO:1 nucleic acid sequence encoding amino acid sequence for mature 2086 protein from CDC1135 strain when combined with a native leader sequence.

SEQ ID NO:2 amino acid sequence for mature 2086 protein from CDC1135 strain prepared using a native leader sequence.

SEQ ID NO:3 nucleic acid sequence for encoding amino acid sequence for mature 2086 protein from CDC1135 when combined with a P4 leader sequence.

SEQ ID NO:4 amino acid sequence for mature 2086 protein from CDC1135 strain prepared using a P4 leader sequence.

SEQ ID NO:5 nucleic acid sequence encoding amino acid sequence for mature 2086 protein from CDC1135 strain.

SEQ ID NO:6 amino acid sequence for mature 2086 protein from CDC1135 strain.

SEQ ID NO:7 nucleic acid sequence encoding amino acid sequence for mature 2086 protein from CDC1127 strain when combined with a native leader sequence.

SEQ ID NO:8 amino acid sequence for mature 2086 protein from CDC1127 strain prepared using a native leader sequence.

SEQ ID NO:9 nucleic acid sequence for encoding amino acid sequence for mature 2086 protein from CDC1127 when combined with a P4 leader sequence.

SEQ ID NO:10 amino acid sequence for mature 2086 protein from CDC1127 strain prepared using a P4 leader sequence.

SEQ ID NO:11 nucleic acid sequence encoding amino acid sequence for mature 2086 protein from CDC1127 strain.

SEQ ID NO:12 amino acid sequence for mature 2086 protein from CDC1127 strain.

DETAILED DESCRIPTION OF THE INVENTION

The present invention provides *Neisseria* ORF2086 proteins ("2086 proteins"), including 2086 Subfamily A proteins and 2086 Subfamily B proteins. Each of the 2086 proteins are proteins that can be isolated from native neisserial strains, including strains of *Neisseria meningitidis* (serogroups A, B, C, D, W-135, X, Y, Z and 29E), *Neisseria gonorrhoeae*, and *Neisseria lactamica*. The 2086 proteins may also be prepared using recombinant technology.

According to various embodiments, the present invention provides the 2086 proteins, immunogenic portions thereof, and/or biological equivalents thereof, antibodies that immunospecifically bind to any of the foregoing, and polynucleotides comprising nucleic acid sequences that encode any of the foregoing. The present invention includes compositions, immunogenic compositions and their use in preventing, treating and/or diagnosing meningococcal infection, and in particular meningococcal disease caused by *N. meningitidis*, as well as methods for preparing said compositions. The 2086 proteins herein include recombinant forms and forms isolated from a natural source, as well as both lipidated and non-lipidated forms.

The present invention unexpectedly and advantageously provides compositions that (1) elicit bactericidal antibodies to multiple neisserial strains, such as strains of *N. meningitidis, N. gonorrhoeae*, and/or *N. lactamica*; (2) react with the surface of multiple strains; (3) confer passive protection against a live challenge; and/or (4) prevent colonization, as well as methods of using said compositions and methods of preparing said compositions. Various embodiments of the invention are described below.

As described herein, new immunogenic composition candidates based on *Neisseria* species ORF2086 protein (also referred to as "2086 protein" or "ORF2086" protein, used interchangeably herein, or P2086 for the non-lipated proteins and LP2086 for the lipidated version of the proteins) isolated from *N. meningitidis* were identified by combining cell fractionation, differential detergent extraction, protein purification, with the preparation of antisera, and a bactericidal activity assay utilizing multiple strains. As an alternative to potential immunogenic compositions and diagnostics disclosed in the references cited above, this invention relates to compositions and methods of treating and/or preventing meningococcal infection through the use of proteins, immunogenic portions thereof and biological equivalents thereof, as well as genes encoding said polypeptides, portions and equivalents, and antibodies that immunospecifically bind to same.

As used herein, the term "non-strain specific" refers to the characteristic of an antigen to elicit an immune response effective against more than one strain of *N. meningitidis* (e.g., heterologous meningococcal strains). The term "cross-reactive" as it is used herein is used interchangeably with the term "non-strain specific". The term "immunogenic non-strain specific *N. meningitidis* antigen," as used herein, describes an antigen that can be isolated from *N. meningitidis*, although it can also be isolated from another bacterium (e.g., other neisserial strains, such as gonococcal strains, for example), or prepared using recombinant technology.

The 2086 proteins of the present invention include lipidated and non-lipidated proteins. Further, the present invention also contemplates the use of the immature proteins or preproteins that correspond to each protein as intermediate compounds/compositions.

The present invention also provides antibodies that immunospecifically bind to the foregoing immunogenic agents, according to implementations of the invention. Further, the present invention relates to isolated polynucleotides comprising nucleic acid sequences encoding any of the foregoing. Additionally, the present invention provides compositions and/or immunogenic compositions and their use in preventing, treating and/or diagnosing meningococcal meningitis, in particular serogroup B meningococcal disease, as well as methods for preparing said compositions.

The compositions of the present invention are highly immunogenic and capable of eliciting the production of bactericidal antibodies. These antibodies are cross-reactive to serogroup, serotype and serosubtype heterologous meningococcal strains. Accordingly, the present compositions overcome the deficiencies of previous *N. meningitidis* vaccine attempts by exhibiting the ability to elicit bactericidal antibodies to heterologous neisserial strains. Thus, among other advantages, the present invention provides immunogenic compositions that can be compounded with fewer components to elicit protection comparable to previously used agents. The compositions or immunogenic agents therein (e.g., polypeptides, immunogenic portions or fragments, and biological equivalents, etc., without limitation) can be used alone or in combination with other antigens or agents to elicit immunological protection from meningococcal infection and disease, as well as to elicit immunological protection from infection and/or disease caused by other pathogens. This simplifies the design of an immunogenic composition for use against meningococcal infection by reducing the number of antigens required for protection against multiple strains. In fact, purified 2086 protein will dramatically and unexpectedly reduce the number of proteins required to provide adequate immunogenic coverage of the strains responsible for meningococcal disease. The 2086 protein can be recombinantly expressed in *E. coli* as a lipoprotein, which is the wild type form of the protein, at levels much higher than in the native meningococci.

The following published international patent applications are incorporated by reference herein in their entirety: PCT/US02/32369 (published as WO 03/063766 on Aug. 7, 2003) and PCT/US04/11901 (published as WO 04/094596 on Nov. 4, 2004).

Although the 2086 protein is not present in large amounts in wild type strains, it is a target for bactericidal antibodies. These antibodies, unlike those produced in response to the PorAs, are capable of killing strains expressing heterologous serosubtypes.

Antibodies to the 2086 protein also passively protect infant rats from challenge with meningococci. Recombinant expression of 2086 protein enables the use of 2086 protein as an immunogenic composition for the prevention of meningococcal disease. All of the recent meningococcal immunogenic composition candidates in clinical trials have been complex mixtures or outer membrane protein preparations containing many different proteins. The PorA protein, that provides serosubtype specificity, will require the inclusion of 6 to 9 variants in an immunogenic composition to provide about 70-80% coverage of disease related serosubtypes. In contrast, it is clearly demonstrated herein that antisera to a single 2086 protein alone is able to kill representatives of six serosubtypes responsible for about 65% of the disease isolates in western Europe and the United States. Therefore, purified 2086 protein has the potential to reduce the number of proteins required to provide adequate immunogenic composition coverage of the serosubtypes responsible for meningococcal disease.

Proteins, Immunogenic Portions and Biological Equivalents

The 2086 proteins provided by the present invention are isolated proteins or polypeptides. The term "isolated" means altered by the hand of man from the natural state. If an "isolated" composition or substance occurs in nature, it has been changed or removed from its original environment, or both. For example, a polypeptide or a polynucleotide naturally present in a living animal is not "isolated," but the same polypeptide or polynucleotide separated from the coexisting materials of its natural state is "isolated", as the term is employed herein. Accordingly, as used herein, the term "isolated protein" encompasses proteins isolated from a natural source and proteins prepared using recombinant technology, as well as such proteins when combined with other antigens and/or additives, such as pharmaceutically acceptable carriers, buffers, adjuvants, etc., for example.

According to an embodiment of the present invention, the 2086 proteins are characterized as being immunogenic, non-pathogenic and non-strain specific. The 2086 proteins are highly variable and thus may undergo insertions, substitutions and/or deletions of amino acid residues without compromising the immunogenicity of the proteins. The 2086 proteins may be divided into two subfamilies, Subfamily A and Subfamily B.

The 2086 proteins from Subfamily A comprise an amino acid sequence of any of the even numbered sequences of SEQ ID NOS:2-6 or an amino acid sequence encoded by a polynucleotide comprising the nucleotide sequence of any of the odd numbered sequences of SEQ ID NOS:1-5. The 2086 proteins from Subfamily B comprise an amino acid sequence of any of the even numbered sequences of SEQ ID NOS:8-12 or an amino acid sequence encoded by a polynucleotide comprising the nucleotide sequence of any of the odd numbered sequences of SEQ ID NOS:7-11.

A polypeptide sequence of the invention may be identical to the reference sequence (e.g., even numbered SEQ ID NOS: 2-12), that is, 100% identical, or it may include a number of amino acid alterations as compared to the reference sequence such that the % identity is less than 100%. Such alterations include at least one amino acid deletion, substitution, including conservative and non-conservative substitution, or insertion. The alterations may occur at the amino- or carboxy-terminal positions of the reference polypeptide sequence or anywhere between those terminal positions, interspersed either individually among the amino acids in the reference amino acid sequence or in one or more contiguous groups within the reference amino acid sequence.

Thus, the invention also provides proteins having sequence identity to the amino acid sequences contained in the Sequence Listing (i.e., even numbered SEQ ID NOS:2-12). According to various embodiments of the present invention, the 2086 protein has a sequence greater than identity of at least about 95%, 96%, 97%, 98%, 99%, 99.9% or more to any of the even numbered amino acid sequences of SEQ ID NOS: 2-12. These include mutants and allelic variants without limitation.

In preferred embodiments of the invention, the 2086 proteins or other 2086 polypeptides (e.g., immunological portions and biological equivalents) generate bactericidal antibodies to homologous and at least one heterologous strain of meningococci. Specifically, the antibodies to the 2086 polypeptides passively protect infant rats from challenge, such as intranasal, with meningococci. In further preferred embodiments, the 2086 polypeptides exhibit such protection for infant rats for homologous strains and at least one heterologous strain. The polypeptide may be selected from the Sequence Summary above, as set forth in the even numbered SEQ ID NOS: 2-12, or the polypeptide may be any immunological fragment or biological equivalent of the listed polypeptides. Preferably, the polypeptide is selected from any of the even numbered SEQ ID NOS: 2-12 in the Sequence Summary above.

This invention also relates to allelic or other variants of the 2086 polypeptides, which are biological equivalents. Suitable biological equivalents will exhibit the ability to (1) elicit bactericidal antibodies to homologous strains and at least one heterologous neisserial strain and/or gonococcal strain; (2) react with the surface of homologous strains and at least one heterologous neisserial and/or gonococcal strain; (3) confer passive protection against a live challenge; and/or (4) prevent colonization.

Suitable biological equivalents have at least about 95%, 96%, 97% 98%, 99% or 99.9% similarity to one of the 2086 polypeptides specified herein (i.e., the even numbered SEQ ID NOS: 2-12), provided the equivalent is capable of eliciting substantially the same immunogenic properties as one of the 2086 proteins of this invention.

Alternatively, the biological equivalents have substantially the same immunogenic properties of one of the 2086 proteins in the even numbered SEQ ID NOS: 2-12. According to embodiments of the present invention, the biological equivalents have the same immunogenic properties as the even numbered SEQ ID NOS: 2-12.

The biological equivalents are obtained by generating variants and modifications to the proteins of this invention. These variants and modifications to the proteins are obtained by altering the amino acid sequences by insertion, deletion or substitution of one or more amino acids. The amino acid sequence is modified, for example by substitution in order to create a polypeptide having substantially the same or improved qualities. A preferred means of introducing alterations comprises making predetermined mutations of the nucleic acid sequence of the polypeptide by site-directed mutagenesis.

Modifications and changes can be made in the structure of a polypeptide of the present invention and still obtain a molecule having N. meningitidis immunogencity. For example, without limitation, certain amino acids can be substituted for other amino acids, including nonconserved and conserved substitution, in a sequence without appreciable loss of immunogenicity. Because it is the interactive capacity and nature of a polypeptide that defines that polypeptide's biological functional activity, a number of amino acid sequence substitutions can be made in a polypeptide sequence (or, of course, its underlying DNA coding sequence) and nevertheless obtain a polypeptide with like properties. The present invention contemplates any changes to the structure of the polypeptides herein, as well as the nucleic acid sequences encoding said polypeptides, wherein the polypeptide retains immunogenicity. A person of ordinary skill in the art would be readily able to modify the disclosed polypeptides and polynucleotides accordingly, based upon the guidance provided herein.

For example, certain variable regions have been identified where substitution or deletion is permissible The 2086 consensus sequence, as previously discussed, shows conserved and nonconserved regions of the 2086 family of proteins according to an implementation of the present invention.

In making such changes, any techniques known to persons of skill in the art may be utilized. For example, without intending to be limited thereto, the hydropathic index of amino acids can be considered. The importance of the hydropathic amino acid index in conferring interactive biologic function on a polypeptide is generally understood in the art. Kyte et al. 1982. *J. Mol. Bio.* 157:105-132.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity, i.e. with a biological property of the polypeptide.

Biological equivalents of a polypeptide can also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the underlying DNA. Such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a phage vector that can exist in both a single stranded and double stranded form. Typically, site-directed mutagenesis in accordance herewith is performed by first obtaining a single-stranded vector which includes within its sequence a DNA sequence which encodes all or a portion of the *N. meningitidis* polypeptide sequence selected. An oligonucleotide primer bearing the desired mutated sequence is prepared (e.g., synthetically). This primer is then annealed to the single-stranded vector, and extended by the use of enzymes such as *E. coli* DNA polymerase I (Klenow fragment), in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as *E. coli* cells and clones are selected which include recombinant vectors bearing the mutation. Commercially available kits come with all the reagents necessary, except the oligonucleotide primers.

2086 polypeptides include any protein or polypeptide comprising substantial sequence similarity and/or biological equivalence to a 2086 protein having an amino acid sequence from one of the even numbered SEQ ID NOS 2-12. In addition, a 2086 polypeptide of the invention is not limited to a particular source. Thus, the invention provides for the general detection and isolation of the polypeptides from a variety of sources. Also, the 2086 polypeptides can be prepared recombinantly, as is well within the skill in the art, based upon the guidance provided herein, or in any other synthetic manner, as known in the art.

It is contemplated in the present invention, that a 2086 polypeptide may advantageously be cleaved into fragments for use in further structural or functional analysis, or in the generation of reagents such as 2086-related polypeptides and 2086-specific antibodies. This can be accomplished by treating purified or unpurified *N. meningitidis* polypeptides with a peptidase such as endoproteinase glu-C (Boehringer, Indianapolis, Ind.). Treatment with CNBr is another method by which peptide fragments may be produced from natural *N. meningitidis* 2086 polypeptides. Recombinant techniques also can be used to produce specific fragments of a 2086 protein.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical (i.e., biologically equivalent). A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. *Applied Math.,* 48:1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., 1984), BLASTP, BLASTN, and FASTA (Altschul, S. F., et al., 1990). The BLASTX program is publicly available from NCBI and other sources (BLAST Manual, Altschul, S., et al., NCBI NLM NIH Bethesda, Md. 20894; Altschul, S., et al., 1990). The well known Smith Waterman algorithm may also be used to determine identity.

By way of example, without intending to be limited thereto, an amino acid sequence of the present invention may be identical to the reference sequences, even numbered SEQ ID NOS: 2-12; that is be 100% identical, or it may include a number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in even numbered SEQ ID NOS:2-12 by the numerical percent of the respective percent identity (divided by 100) and then subtracting that product from said total number of amino acids in any of even numbered SEQ ID NOS:2-12, or:

$$n_a = x_a - (x_a \cdot y),$$

wherein $n_a$ is the number of amino acid alterations, $x_a$ is the total number of amino acids in even numbered SEQ ID NOS: 2-12, and y is, for instance 0.70 for 70%, 0.80 for 80%, 0.85 for 85% etc., and wherein any non-integer product of $x_a$ and y is rounded down to the nearest integer prior to subtracting it from $x_a$.

In preferred embodiments, the polypeptide above is selected from the proteins set forth in the even numbered SEQ ID NOS 2-12, such as mature processed form of a 2086 protein. The 2086 proteins or equivalents, etc. may be lipidated or non-lipidated.

ORF 2086 is expressible in *E. coli* with the native ORF 2086 signal sequence. However, it is desirable to find means to improve the expression of proteins. According to an embodiment of the present invention, a leader sequence produces a lipidated form of the protein. For example, the following describes the use of the signal sequence of the non-typable *Haemophilus influenzae* P4 protein to enhance expression.

The processing of bacterial lipoproteins begins with the synthesis of a precursor or prolipoprotein containing a signal sequence, which in turn contains a consensus lipoprotein processing/modification site. This prolipoprotein initially passes through the common Sec system on the inner membrane of Gram negative bacteria or on the membrane in Gram positive bacteria. Once placed in the membrane by the Sec system, the prolipoprotein is cleaved by signal peptidase II at the consensus site and the exposed N-terminal cysteine residue is glycerated and acylated. Hayashi et al. 1990. Lipoproteins in bacteria. *J. Bioenerg. Biomembr*. June; 22(3):451-71; Oudega et al. 1993. *Escherichia coli* SecB, SecA, and SecY proteins are required for expression and membrane insertion of the bacteriocin release protein, a small lipoprotein. *J. Bacteriol*. March; 175(5):1543-7; Sankaran et al. 1995. Modification of bacterial lipoproteins. *Methods Enzymol.* 250:683-97.

In Gram negative bacteria, transport of the lipidated protein to the outer membrane is mediated by a unique ABC transporter system with membrane specificity depending on a sorting signal at position 2 of the lipoprotein. Yakushi et al. 2000. A new ABC transporter mediating the detachment of lipid modified proteins from membranes. *Nat Cell Biol. April;* 2(4):212-8.

Fusion with bacterial lipoproteins and their signal sequences has been used to display recombinant proteins on the surface of bacteria. U.S. Pat. Nos. 5,583,038 and 6,130,085. Exchanging lipoprotein signal sequences can increase the production of the lipoprotein. De et al. 2000. Purification and characterization of *Streptococcus pneumoniae* palmitoylated pneumococcal surface adhesin A expressed in *Escherichia coli*. Vaccine. March 6; 18(17):1811-21.

Bacterial lipidation of proteins is known to increase or modify the immunological response to proteins. Erdile et al. 1993. Role of attached lipid in immunogenicity of *Borrelia burgdorferi* OspA. *Infect. Immun.* January; 61(1):81-90; Snapper et al. 1995. Bacterial lipoproteins may substitute for cytokines in the humoral immune response to T cell-independent type II antigens. *J. Immunol.* December 15; 155(12): 5582-9. However, bacterial lipoprotein expression can be complicated by the stringency of the processing. Pollitt et al. 1986. Effect of amino acid substitutions at the signal peptide cleavage site of the *Escherichia coli* major outer membrane lipoprotein. *J. Biol. Chem.* February 5; 261(4):1835-7; Lunn et al. 1987. Effects of prolipoprotein signal peptide mutations on secretion of hybrid prolipo-beta-lactamase in *Escherichia coli. J. Biol. Chem.* June 15; 262(17):8318-24; Klein et al. 1988. Distinctive properties of signal sequences from bacterial lipoproteins. *Protein Eng.* April; 2(1):15-20. Bacterial lipoprotein expression is also complicated by other problems such as toxicity and low expression levels. Gomez et al. 1994. Nucleotide The *Bacillus subtilis* lipoprotein LpIA causes cell lysis when expressed in *Escherichia coli. Microbiology.* August; 140 (Pt 8):1839-45; Hansson et al. 1995. Expression of truncated and full-length forms of the Lyme disease *Borrelia* outer surface protein A in *Escherichia coli. Protein Expr. Purif.* February; 6(1):15-24; Yakushi et al. 1997. Lethality of the covalent linkage between mislocalized major outer membrane lipoprotein and the peptidoglycan of *Escherichia coli. J. Bacteriol.* May; 179(9):2857-62.

The nontypable *Haemophilus influenzae* bacterium expresses a lipoprotein designated P4 (also known as protein "e"). The recombinant form of the P4 protein is highly expressed in *E. coli* using the native P4 signal sequence. U.S. Pat. No. 5,955,580. When the native P4 signal sequence is substituted for the native ORF 2086 signal sequence in an expression vector in *E. coli*, the level of expression of ORF2086 is increased.

This concept of using the heterologous P4 signal sequence to increase expression is extendible to other bacterial lipoproteins. In particular, analysis of bacterial genomes leads to the identification of many ORFs as being of possible interest. Attempting to express each ORF with its native signal sequence in a heterologous host cell, such as *E. coli*, gives rise to a variety of problems inherent in using a variety of signal sequences, including stability, compatibility and so forth. To minimize these problems, the P4 signal sequence is used to express each ORF of interest. As described above, the P4 signal sequence improves the expression of the heterologous 2086 ORF. An expression vector is constructed by deleting the native signal sequence of the ORF of interest, and ligating the P4 signal sequence to the ORF. A suitable host cell is then transformed, transfected or infected with the expression vector, and expression of the ORF is increased in comparison to expression using the native signal sequence of the ORF.

The non-lipidated form is produced by a protein lacking the original leader sequence or a by a leader sequence which is replaced with a portion of sequence that does not specify a site for fatty acid acylation in a host cell.

The various forms of the 2086 proteins of this invention are referred to herein as "2086" protein, unless otherwise specifically noted. Also "2086 polypeptide" refers to the 2086 proteins as well as immunogenic portions or biological equivalents thereof as noted above, unless otherwise noted.

The full length isolated and purified *N. meningitidis* 2086 protein has an apparent molecular weight of about 28 to 35 kDa as measured on a 10% to 20% gradient SDS polyacrylamide gel (SDS-PAGE). More specifically, this protein has a molecular weight of about 26,000 to 30,000 daltons as measured by mass spectrometry.

Preferably, the 2086 polypeptides and nucleic acids encoding such polypeptides are used for preventing or ameliorating infection caused by *N. meningitidis* and/or other species.

Antibodies

The proteins of the invention, including the amino acid sequences of SEQ ID NOS: 2-12, their fragments, and analogs thereof, or cells expressing them, are also used as immunogens to produce antibodies immunospecific for the polypeptides of the invention. The invention includes antibodies to immunospecific polypeptides and the use of such antibodies to detect the presence of *N. meningitidis*, provide passive protection or measure the quantity or concentration of the polypeptides in a cell, a cell or tissue extract, or a biological fluid.

The antibodies of the invention include polyclonal antibodies, monoclonal antibodies, chimeric antibodies, and anti-idiotypic antibodies. Polyclonal antibodies are heterogeneous populations of antibody molecules derived from the sera of animals immunized with an antigen. Monoclonal antibodies are a substantially homogeneous population of antibodies to specific antigens. Monoclonal antibodies may be obtained by methods known to those skilled in the art, e.g., Kohler and Milstein, 1975, *Nature* 256:495-497 and U.S. Pat. No. 4,376,110. Such antibodies may be of any immunoglobulin class including IgG, IgM, IgE, IgA, GILD and any subclass thereof.

Chimeric antibodies are molecules, different portions of which are derived from different animal species, such as those having variable region derived from a murine monoclonal antibody and a human immunoglobulin constant region. Chimeric antibodies and methods for their production are known in the art (Cabilly et al., 1984, *Proc. Natl. Acad. Sci. USA* 81:3273-3277; Morrison et al., 1984, *Proc. Natl. Acad. Sci. USA* 81:6851-6855; Boulianne et al., 1984, *Nature* 312:643-646; Cabilly et al., European Patent Application 125023 (published Nov. 14, 1984); Taniguchi et al., European Patent Application 171496 (published Feb. 19, 1985); Morrison et al., European Patent Application 173494 (published Mar. 5, 1986); Neuberger et al., PCT Application WO 86/01533 (published Mar. 13, 1986); Kudo et al., European Patent Application 184187 (published Jun. 11, 1986); Morrison et al., European Patent Application 173494 (published Mar. 5, 1986); Sahagan et al., 1986, *J. Immunol.* 137:1066-1074; Robinson et. al., PCT/US86/02269 (published May 7, 1987); Liu et al., 1987, *Proc. Natl. Acad. Sci. USA* 84:3439-3443; Sun et al., 1987, *Proc. Natl. Acad. Sci. USA* 84:214-218; Better et al., 1988, *Science* 240:1041-1043). These references are hereby incorporated by reference in their entirety.

An anti-idiotypic (anti-Id) antibody is an antibody that recognizes unique determinants generally associated with the antigen-binding site of an antibody. An anti-Id antibody is prepared by immunizing an animal of the same species and genetic type (e.g., mouse strain) as the source of the monoclonal antibody with the monoclonal antibody to which an anti-Id is being prepared. The immunized animal will recognize and respond to the idiotypic determinants of the immunizing antibody by producing an antibody to these isotypic determinants (the anti-Id antibody).

Accordingly, monoclonal antibodies generated against the polypeptides of the present invention may be used to induce anti-Id antibodies in suitable animals. Spleen cells from such immunized mice can be used to produce anti-Id hybridomas secreting anti-Id monoclonal antibodies. Further, the anti-Id antibodies can be coupled to a carrier such as keyhole limpet hemocyanin (KLH) and used to immunize additional BALB/c mice. Sera from these mice will contain anti-anti-Id antibodies that have the binding properties of the final mAb specific for an R-PTPase epitope. The anti-Id antibodies thus have their idiotypic epitopes, or "idiotopes" structurally similar to the epitope being evaluated, such as *Streptococcus pyogenes* polypeptides.

The term "antibody" is also meant to include both intact molecules as well as fragments such as Fab, single chain antibodies and other antigen-recognizing fragments of antibodies which are capable of binding antigen. Fab fragments lack the Fc fragment of intact antibody, clear more rapidly from the circulation, and may have less non-specific tissue binding than an intact antibody (Wahl et al., 1983, *J. Nucl. Med.* 24:316-325). It will be appreciated that Fab and other fragments of the antibodies useful in the present invention may be used for the detection and quantitation of *N. meningitidis* polypeptides according to the methods for intact antibody molecules.

The antibodies of this invention, such as anti-iodiotypic ("anti-Id") antibodies, can be employed in a method for the treatment or prevention of *Neisseria* infection in mammalian hosts, which comprises administration of an immunologically effective amount of antibody, specific for a polypeptide as described above. The anti-Id antibody may also be used as an "immunogen" to induce an immune response in yet another animal, producing a so-called anti-anti-Id antibody. The anti-anti-Id may be epitopically identical to the original mAb that induced the anti-Id. Thus, by using antibodies to the idiotypic determinants of a mAb, it is possible to identify other clones expressing antibodies of identical specificity.

The antibodies are used in a variety of ways, e.g., for confirmation that a protein is expressed, or to confirm where a protein is expressed. Labeled antibody (e.g., fluorescent labeling for FACS) can be incubated with intact bacteria and the presence of the label on the bacterial surface confirms the location of the protein, for instance.

Antibodies generated against the polypeptides of the invention can be obtained by administering the polypeptides or epitope-bearing fragments, analogs, or cells to an animal using routine protocols. For preparing monoclonal antibodies, any technique that provides antibodies produced by continuous cell line cultures are used.

Polynucleotides

As with the proteins of the present invention, a polynucleotide of the present invention may comprise a nucleic acid sequence that is identical to any of the reference sequences of odd numbered SEQ ID NOS:1-11, that is be 100% identical, or it may include up to a number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in any of odd numbered SEQ ID NOS:1-11 by the numerical percent of the respective percent identity (divided by 100) and subtracting that product from said total number of nucleotides in said sequence.

By way of example, without intending to be limited thereto, an isolated *N. meningitidis* polynucleotide comprising a polynucleotide sequence that has at least 95% identity to any nucleic acid sequence of odd numbered SEQ ID NOS:1-11; a degenerate variant thereof or a fragment thereof, wherein the polynucleotide sequence may include up to $n_n$ nucleic acid alterations over the entire polynucleotide region of the nucleic acid sequence of odd numbered SEQ ID NOS: 1-11, wherein $n_n$ is the maximum number of alterations and is calculated by the formula:

$$n_n = x_n - (x_n \cdot y),$$

in which $X_n$ is the total number of nucleic acids of any of odd numbered SEQ ID NOS:1-11 and y has a value of 0.95, wherein any non-integer product of $x_n$ and y is rounded down to the nearest integer prior to subtracting such product from $x_n$. Of course, y may also have a value of 0.95 for 95%, etc. Alterations of a polynucleotide sequence encoding the polypeptides comprising amino acid sequences of any of even numbered SEQ ID NOS:2-12 may create nonsense, missense or frameshift mutations in this coding sequence and thereby alter the polypeptide encoded by the polynucleotide following such alterations.

Certain embodiments of the present invention relate to polynucleotides (herein referred to as the "2086 polynucleotides" or "ORF2086 polynucleotides") that encode the 2086 proteins and antibodies made against the 2086 proteins. In preferred embodiments, an isolated polynucleotide of the present invention is a polynucleotide comprising a nucleotide sequence having at least about 95% identity to a nucleotide sequence chosen from one of the odd numbered SEQ ID NOS:1-11, a degenerate variant thereof, or a fragment thereof. As defined herein, a "degenerate variant" is defined as a polynucleotide that differs from the nucleotide sequence shown in the odd numbered SEQ ID NOS:1-11 (and fragments thereof) due to degeneracy of the genetic code, but still encodes the same 2086 protein (e.g., the even numbered SEQ ID NOS: 2-12) as that encoded by the nucleotide sequence shown in the odd numbered SEQ ID NOS: 1-11.

In other embodiments, the polynucleotide is a complement to a nucleotide sequence chosen from one of the odd numbered SEQ ID NOS: 1-11, a degenerate variant thereof, or a fragment thereof. In yet other embodiments, the polynucleotide is selected from the group consisting of DNA, chromosomal DNA, cDNA and RNA and may further comprises heterologous nucleotides.

It will be appreciated that the 2086 polynucleotides may be obtained from natural, synthetic or semi-synthetic sources; furthermore, the nucleotide sequence may be a naturally occurring sequence, or it may be related by mutation, including single or multiple base substitutions, deletions, insertions and inversions, to such a naturally occurring sequence, provided always that the nucleic acid molecule comprising such a sequence is capable of being expressed as 2086 immunogenic polypeptide as described above. The nucleic acid molecule may be RNA, DNA, single stranded or double stranded, linear or covalently closed circular form. The nucleotide sequence may have expression control sequences positioned adjacent to it, such control sequences usually being derived from a heterologous source. Generally, recombinant expression of the nucleic acid sequence of this invention will use a stop codon sequence, such as TAA, at the end of the nucleic acid sequence.

The invention also includes polynucleotides capable of hybridizing under reduced stringency conditions, more preferably stringent conditions, and most preferably highly stringent conditions, to polynucleotides described herein.

Examples of stringency conditions are shown in the Stringency Conditions Table below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE I

STRINGENCY CONDITIONS

| Stringency Condition | Polynu-cleotide Hybrid | Hybrid Length (bp)$^f$ | Hybridization Temperature and Buffer$^H$ | Wash Temperature and Buffer$^H$ |
|---|---|---|---|---|
| A | DNA:DNA | >50 | 65EC; 1xSSC -or- 42EC; 1xSSC, 50% formamide | 65EC; 0.3xSSC |
| B | DNA:DNA | <50 | $T_B$; 1xSSC | $T_B$; 1xSSC |
| C | DNA:RNA | >50 | 67EC; 1xSSC -or- 45EC; 1xSSC, 50% formamide | 67EC; 0.3xSSC |
| D | DNA:RNA | <50 | $T_D$; 1xSSC | $T_D$; 1xSSC |
| E | RNA:RNA | >50 | 70EC; 1xSSC -or- 50EC; 1xSSC, 50% formamide | 70EC; 0.3xSSC |
| F | RNA:RNA | <50 | $T_F$; 1xSSC | $T_F$; 1xSSC |
| G | DNA:DNA | >50 | 65EC; 4xSSC -or- 42EC; 4xSSC, 50% formamide | 65EC; 1xSSC |
| H | DNA:DNA | <50 | $T_H$; 4xSSC | $T_H$; 4xSSC |
| I | DNA:RNA | >50 | 67EC; 4xSSC -or- 45EC; 4xSSC, 50% formamide | 67EC; 1xSSC |
| J | DNA:RNA | <50 | $T_J$; 4xSSC | $T_J$; 4xSSC |
| K | RNA:RNA | >50 | 70EC; 4xSSC -or- 50EC; 4xSSC, 50% formamide | 67EC; 1xSSC |
| L | RNA:RNA | <50 | $T_L$; 2xSSC | $T_L$; 2xSSC |
| M | DNA:DNA | >50 | 50EC; 4xSSC -or- 40EC; 6xSSC, 50% formamide | 50EC; 2xSSC |
| N | DNA:DNA | <50 | $T_N$; 6xSSC | $T_N$; 6xSSC |
| O | DNA:RNA | >50 | 55EC; 4xSSC -or- 42EC; 6xSSC, 50% formamide | 55EC; 2xSSC |
| P | DNA:RNA | <50 | $T_P$; 6xSSC | $T_P$; 6xSSC |
| Q | RNA:RNA | >50 | 60EC; 4xSSC -or- 45EC; 6xSSC, 50% formamide | 60EC; 2xSSC |
| R | RNA:RNA | <50 | $T_R$; 4xSSC | $T_R$; 4xSSC | bp$^f$: The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarities.
buffer$^H$: SSPE (1xSSPE is 0.15M NaCl, 10 mM NaH$_2$PO$_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.
$T_B$ through $T_R$: The hybridization temperature for hybrids anticipated to be less than 50 base pairs in length should be 5-10EC less than the melting temperature ($T_m$) of the hybrid, where $T_m$ is determined according to the following equations. For hybrids less than 18 base pairs in length, $T_m$(EC) = 2(# of A + T bases) + 4(# of G + C bases). For hybrids between 18 and 49 base pairs in length, $T_m$(EC) = 81.5 + 16.6(log$_{10}$[Na$^+$]) + 0.41(% G + C) − (600/N), where N is the number of bases in the hybrid, and [Na$^+$] is the concentration of sodium ions in the hybridization buffer ([Na$^+$] for 1xSSC = 0.165M).

Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference.

The invention also provides polynucleotides that are fully complementary to these polynucleotides and also provides antisense sequences. The antisense sequences of the invention, also referred to as antisense oligonucleotides, include both internally generated and externally administered sequences that block expression of polynucleotides encoding the polypeptides of the invention. The antisense sequences of the invention comprise, for example, about 15-20 base pairs. The antisense sequences can be designed, for example, to inhibit transcription by preventing promoter binding to an upstream nontranslated sequence or by preventing translation of a transcript encoding a polypeptide of the invention by preventing the ribosome from binding.

The polynucleotides of the invention are prepared in many ways (e.g., by chemical synthesis, from DNA libraries, from the organism itself) and can take various forms (e.g., single-stranded, double-stranded, vectors, probes, primers). The term "polynucleotide" includes DNA and RNA, and also their analogs, such as those containing modified backbones.

According to further implementations of the present invention, the polynucleotides of the present invention comprise a DNA library, such as a cDNA library.

Fusion Proteins

The present invention also relates to fusion proteins. A "fusion protein" refers to a protein encoded by two, often unrelated, fused genes or fragments thereof. For example, fusion proteins comprising various portions of constant region of immunoglobulin molecules together with another immunogenic protein or part thereof. In many cases, employing an immunoglobulin Fc region as a part of a fusion protein is advantageous for use in therapy and diagnosis resulting in, for example, improved pharmacokinetic properties (see, e.g., EP 0 232 262 A1). On the other hand, for some uses it would be desirable to be able to delete the Fc part after the fusion protein has been expressed, detected and purified. The 2086 polynucleotides of the invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro-protein sequence, or other fusion peptide portions. For example, a marker sequence which facilitates purification of a 2086 polypeptide or fused polypeptide can be encoded (see Gentz et al., 1989, incorporated herein by reference in its entirety). Thus, contemplated in an implementation of the present invention is the preparation of polynucleotides encoding fusion polypeptides permitting His-tag purification of expression products. The polynucleotide may also contain non-coding 5' and 3' sequences, such as transcribed, non-translated sequences, splicing and polyadenylation signals. Such a fused polypeptide can be produced by a host cell transformed/transfected or infected or infected with a recombinant DNA cloning vehicle as described below and it can be subsequently isolated from the host cell to provide the fused polypeptide substantially free of other host cell proteins.

Immunogenic Compositions

One aspect of the present invention provides immunogenic compositions which comprise at least one 2086 proteins or a nucleic acid encoding said proteins. The foregoing have the ability to (1) elicit bactericidal antibodies to multiple strains; (2) react with the surface of multiple strains; (3) confer passive protection against a live challenge; and/or (4) prevent colonization. The formulation of such immunogenic compositions is well known to persons skilled in this field. In certain embodiments, the compositions of the invention include a pharmaceutically acceptable carrier and/or diluent. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antibody. The preparation and use of pharmaceutically acceptable carriers is well known in the art. Except insofar as any conventional media or agent is incompatible with the active ingredient, use thereof in the immunogenic compositions of the present invention is contemplated. According to certain embodiments of the present invention, the pharmaceutically acceptable carrier is a carrier protein.

Carrier Proteins

Carrier proteins are preferably proteins that are non-toxic and non-reactogenic and obtainable in sufficient amount and purity. Carrier proteins should be amenable to standard conjugation procedures. In a particular embodiment of the present invention, $CRM_{197}$ is used as the carrier protein.

$CRM_{197}$ (Wyeth, Sanford, N.C.) is a non-toxic variant (i.e., toxoid) of diphtheria toxin isolated from cultures of *Corynebacterium diphtheria* strain C7 ($\beta$197) grown in casamino acids and yeast extract-based medium. $CRM_{197}$ is purified through ultra-filtration, ammonium sulfate precipitation, and ion-exchange chromatography. Another method of obtaining $CRM_{197}$ is described in U.S. Pat. No. 4,925,792. Alternatively, $CRM_{197}$ is prepared recombinantly in accordance with U.S. Pat. No. 5,614,382. Other diphtheria toxoids are also suitable for use as carrier proteins.

In other embodiments, a carrier protein of the invention is an enzymatically inactive streptococcal C5a peptidase (SCP) (e.g., one or more of the SCP variants described in U.S. Pat. Nos. 6,270,775, 6,355,255 and 6,951,653).

Other suitable carrier proteins include inactivated bacterial toxins such as tetanus toxoid, pertussis toxoid, cholera toxoid (e.g., CT E29H, described in International PCT Publication No. WO2004/083251), *E. coli* LT, *E. coli* ST, *E. coli* DnaK protein, and exotoxin A from *Pseudomonas aeruginosa*. Bacterial outer membrane proteins such as outer membrane complex c (OMPC), porins, transferrin binding proteins, pneumolysin toxin (e.g., U.S. Pat. No. 5,565,204), pneumolysin toxoid (e.g., International PCT Publication No. WO2005/108580) pneumococcal surface protein A (PspA), pneumococcal adhesin protein (PsaA), or *Haemophilus influenzae* protein D, can also be used. Bacterial heat shock proteins, such as mycobacterial hsp-70 can also be used. Other proteins, such as *Staphylococcus epidermidis* proteins SdrG, SitC and ferrochrome binding proteins, and *Staphylococcus aureus* proteins ClfA, ClfB and FnbA can also be used. Still other proteins, such as ovalbumin, keyhole limpet haemocyanin (KLH), glutathione S-transferase (GST), bovine serum albumin (BSA), galactokinase (galK), ubiquitin, $\beta$-galactosidase, influenza NS1 protein, or purified protein derivative of tuberculin (PPD) can also be used as carrier proteins. Virus-like particles, for example from rotavirus VP6 or from bacteriophage Q$\beta$, can also be used.

Adjuvants

Immunogenic compositions as described herein also comprise, in certain embodiments, one or more adjuvants. An adjuvant is a substance that enhances the immune response when administered together with an immunogen or antigen. A number of cytokines or lymphokines have been shown to have immune modulating activity, and thus are useful as adjuvants, including, but not limited to, the interleukins 1-$\alpha$, 1-$\beta$, 2, 4, 5, 6, 7, 8, 10, 12 (see, e.g., U.S. Pat. No. 5,723,127), 13, 14, 15, 16, 17 and 18 (and its mutant forms); the interferons-$\alpha,\beta$ and $\gamma$; granulocyte-macrophage colony stimulating factor (GM-CSF) (see, e.g., U.S. Pat. No. 5,078,996 and ATCC Accession Number 39900); macrophage colony stimulating factor (M-CSF); granulocyte colony stimulating factor (G-CSF); and the tumor necrosis factors $\alpha$ and $\beta$. Still other adjuvants that are useful with the immunogenic compositions described herein include chemokines, including without limitation, MCP-1, MIP-1$\alpha$, MIP-1$\beta$, and RANTES; adhesion molecules, such as a selectin, e.g., L-selectin, P-selectin and E-selectin; mucin-like molecules, e.g., CD34, GlyCAM-1 and MadCAM-1; a member of the integrin family such as LFA-1, VLA-1, Mac-1 and p150.95; a member of the immunoglobulin superfamily such as PECAM, ICAMs, e.g., ICAM-1, ICAM-2 and ICAM-3, CD2 and LFA-3; co-stimulatory molecules such as CD40 and CD40L; growth factors including vascular growth factor, nerve growth factor, fibroblast growth factor, epidermal growth factor, B7.2, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; and Caspase (ICE).

Suitable adjuvants used to enhance an immune response further include, without limitation, MPL™ (3-O-deacylated monophosphoryl lipid A, Corixa, Hamilton, Mont.), which is described in U.S. Pat. No. 4,912,094. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918. One such AGP is 2-[(R)-3-Tetradecanoyloxytetradecanoylamino]ethyl 2-Deoxy-4-O-phosphono-3-O—[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form (AF) or as a stable emulsion (SE).

Still other adjuvants include muramyl peptides, such as N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE); oil-in-water emulsions, such as MF59 (International PCT Publication No. WO 90/14837) (containing 5% Squalene, 0.5% TWEEN 80, and 0.5% SPAN 85 (optionally containing various amounts of MTP-PE) formulated into submicron particles using a microfluidizer such as Model 110Y microfluidizer (Microfluidics, Newton, Mass.)), and SAF (containing 10% Squalene, 0.4% TWEEN 80, 5% pluronic-blocked polymer L121, and thr-MDP, either microfluidized into a submicron emulsion or vortexed to generate a larger particle size emulsion); incomplete Freund's adjuvant (IFA); aluminum salts (alum), such as aluminum hydroxide, aluminum phosphate, aluminum sulfate; Amphigen; Avridine; L121/squalene; D-lactide-polylactide/glycoside; pluronic polyols; killed *Bordetella*; saponins, such as Stimulon™ QS-21 (Antigenics, Framingham, Mass.), described in U.S. Pat. No. 5,057,540, ISCOMATRIX (CSL Limited, Parkville, Australia), described in U.S. Pat. No. 5,254,339, and immunostimulating complexes (ISCOMS); *Mycobacterium tuberculosis*; bacterial lipopolysaccharides; synthetic polynucleotides such as oligonucleotides containing a CpG motif (e.g., U.S. Pat. No. 6,207,646); IC-31 (Intercell AG, Vienna, Austria), described in European Patent Nos. 1,296,713 and 1,326,634; a pertussis toxin (PT) or mutant thereof, a cholera toxin or mutant thereof (, e.g., International PCT Publication Nos. WO00/18434, WO02/098368 and WO02/098369); or an *E. coli* heat-labile toxin (LT), particularly LT-K63, LT-R72, PT-K9/G129; see, e.g., International PCT Publication Nos. WO 93/13302 and WO 92/19265.

Modes of Administration

Such immunogenic compositions can be administered parenterally, e.g., by injection, either subcutaneously or intramuscularly, as well as orally or intranasally. Methods for intramuscular immunization are described by Wolff et al. and by Sedegah et al. Other modes of administration employ oral formulations, pulmonary formulations, suppositories, and transdermal applications, for example, without limitation. Oral formulations, for example, include such normally employed excipients as, for example, pharmaceutical grades of mannitol, lactose, starch, magnesium stearate, sodium saccharine, cellulose, magnesium carbonate, and the like, without limitation.

The immunogenic compositions of this invention may be delivered in the form of ISCOMS (immune stimulating complexes), ISCOMS containing CTB, liposomes or encapsulated in compounds such as acrylates or poly(DL-lactide-co-glycoside) to form microspheres of a size suited to adsorption. The proteins of this invention may also be incorporated into oil emulsions.

Multiple Antigens

The immunogenic agents, including proteins, polynucleotides and equivalents of the present invention may be administered as the sole active immunogen in a immunogenic composition, or alternatively, the composition may include other active immunogens, including other *Neisseria* sp. immunogenic polypeptides, or immunologically-active proteins of one or more other microbial pathogens (e.g. virus, prion, bacterium, or fungus, without limitation) or capsular polysaccharide. The compositions may comprise one or more desired proteins, fragments or pharmaceutical compounds as desired for a chosen indication. In the same manner, the compositions of this invention which employ one or more nucleic acids in the immunogenic composition may also include nucleic acids which encode the same diverse group of proteins, as noted above.

Any multi-antigen or multi-valent immunogenic composition is contemplated by the present invention. For example, the compositions of the present invention may a comprise combinations of two or more 2086 proteins, a combination of 2086 protein with one or more Por A proteins, a combination of 2086 protein with meningococcus serogroup A, C, Y and W135 polysaccharides and/or polysaccharide conjugates, a combination of 2086 protein with meningococcus and pneumococcus combinations, or a combination of any of the foregoing in a form suitable for mucosal delivery. Persons of skill in the art would be readily able to formulate such multi-antigen or multi-valent immunologic compositions.

The present invention also contemplates multi-immunization regimens wherein any composition useful against a pathogen may be combined therein or therewith the compositions of the present invention. For example, without limitation, a patient may be administered the immunogenic composition of the present invention and another immununological composition for immunizing against *S. Pneumoniae*, as part of a multi-immunization regimen. Persons of skill in the art would be readily able to select immunogenic compositions for use in conjunction with the immunogenic compositions of the present invention for the purposes of developing and implementing multi-immunization regimens.

Specific embodiments of this invention relate to the use of one or more polypeptides of this invention, or nucleic acids encoding such, in a composition or as part of a treatment regimen for the prevention or amelioration of *S. pneumoniae* infection. One can combine the 2086 polypeptides or 2086 polynucleotides with any immunogenic composition for use against *S. pneumoniae* infection. One can also combine the 2086 polypeptides or 2086 polynucleotides with any other protein or polysaccharide-based meningococcal vaccine.

The 2086 polypeptides, fragments and equivalents can be used as part of a conjugate immunogenic composition; wherein one or more proteins or polypeptides are conjugated to a carrier protein in order to generate a composition that has immunogenic properties against several serotypes and/or against several diseases. Alternatively, one of the 2086 polypeptides can be used as a carrier protein for other immunogenic polypeptides.

The present invention also relates to a method of inducing immune responses in a mammal comprising the step of providing to said mammal an immunogenic composition of this invention. The immunogenic composition is a composition which is antigenic in the treated animal or human such that the immunologically effective amount of the polypeptide(s) contained in such composition brings about the desired immune response against *N. meningitidis* infection. Preferred embodiments relate to a method for the treatment, including amelioration, or prevention of *N. meningitidis* infection in a human comprising administering to a human an immunologically effective amount of the composition.

The phrase "immunologically effective amount," as used herein, refers to the administration of that amount to a mammalian host (preferably human), either in a single dose or as part of a series of doses, sufficient to at least cause the immune system of the individual treated to generate a response that reduces the clinical impact of the bacterial infection. This may range from a minimal decrease in bacterial burden to prevention of the infection. Ideally, the treated individual will not exhibit the more serious clinical manifestations of the bacterial infection. The dosage amount can vary depending upon specific conditions of the individual. This amount can be determined in routine trials or otherwise by means known to those skilled in the art.

Another specific aspect of the present invention relates to using as the immunogenic composition a vector or plasmid that expresses an protein of this invention, or an immunogenic portion thereof. Accordingly, as a further aspect this invention provides a method of inducing an immune response in a mammal, which comprises providing to a mammal a vector or plasmid expressing at least one isolated 2086 polypeptide. The protein of the present invention can be delivered to the mammal using a live vector, in particular using live recombinant bacteria, viruses or other live agents, containing the genetic material necessary for the expression of the polypeptide or immunogenic portion as a foreign polypeptide.

According to a further implementation of the present invention, a method is provided for diagnosing bacterial meningitis in a mammal comprising: detecting the presence of immune complexes in the mammal or a tissue sample from said mammal, said mammal or tissue sample being contacted with an antibody composition comprising antibodies that immunospecifically bind with at least one polypeptide comprising the amino acid sequence of any of the even numbered SEQ ID NOS: 2-12; wherein the mammal or tissue sample is contacted with the antibody composition under conditions suitable for the formation of the immune complexes.

Viral and Non-Viral Vectors

Preferred vectors, particularly for cellular assays in vitro and in vivo, are viral vectors, such as lentiviruses, retroviruses, herpes viruses, adenoviruses, adeno-associated viruses, vaccinia virus, baculovirus, and other recombinant viruses with desirable cellular tropism. Thus, a nucleic acid encoding a 2086 protein or immunogenic fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in PCT Publication No. WO 95/28494, which is incorporated herein by reference in its entirety.

Viral vectors commonly used for in vivo or ex vivo targeting and therapy procedures are DNA-based vectors and retroviral vectors. Methods for constructing and using viral vectors are known in the art (e.g., Miller and Rosman, *BioTechniques,* 1992, 7:980-990). Preferably, the viral vectors are replication-defective, that is, they are unable to replicate autonomously in the target cell. Preferably, the replication defective virus is a minimal virus, i.e., it retains only the sequences of its genome which are necessary for encapsulating the genome to produce viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., *Molec. Cell. Neurosci.,* 1991, 2:320-330), defective herpes virus vector lacking a glycoprotein L gene, or other defective herpes virus vectors (PCT Publication Nos. WO 94/21807 and WO 92/05263); an attenuated adenovirus vector, such as the vector described by Stratford-Perricaudet et al. (*J. Clin. Invest.,* 1992, 90:626-630; see also La Salle et al., *Science,* 1993, 259:988-990); and a defective adeno-associated virus vector (Samulski et al., J. Virol., 1987, 61:3096-3101; Samulski et al., *J. Virol.,* 1989, 63:3822-3828; Lebkowski et al., *Mol. Cell. Biol.,* 1988, 8:3988-3996), each of which is incorporated by reference herein in its entirety.

Various companies produce viral vectors commercially, including, but not limited to, Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors), incorporated by reference herein in its entirety.

Adenovirus Vectors.

Adenoviruses are eukaryotic DNA viruses that can be modified to efficiently deliver a nucleic acid of this invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see PCT Publication No. WO 94/26914). Those adenoviruses of animal origin which can be used within the scope of the present invention include adenoviruses of canine, bovine, murine (example: May 1, Beard et al., Virology, 1990, 75-81), ovine, porcine, avian, and simian (example: SAV) origin. Preferably, the adenovirus of animal origin is a canine adenovirus, more preferably a CAV2 adenovirus (e.g., Manhattan or A26/61 strain, ATCC VR-800, for example). Various replication defective adenovirus and minimum adenovirus vectors have been described (PCT Publication Nos. WO 94/26914, WO 95/02697, WO 94/28938, WO 94/28152, WO 94/12649, WO 95/02697, WO 96/22378). The replication defective recombinant adenoviruses according to the invention can be prepared by any technique known to the person skilled in the art (Levrero et al., *Gene,* 1991, 101:195; European Publication No. EP 185 573; Graham, EMBO J., 1984, 3:2917; Graham et al., *J. Gen. Virol.,* 1977, 36:59). Recombinant adenoviruses are recovered and purified using standard molecular biological techniques, which are well known to persons of ordinary skill in the art.

Adeno-Associated Viruses.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. The use of vectors derived from the AAVs for transferring genes in vitro and in vivo has been described (see, PCT Publication Nos. WO 91/18088 and WO 93/09239; U.S. Pat. Nos. 4,797,368 and 5,139,941; European Publication No. EP 488 528). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants that are produced are then purified by standard techniques.

Retrovirus Vectors.

In another implementation of the present invention, the nucleic acid can be introduced in a retroviral vector, e.g., as described in U.S. Pat. No. 5,399,346; Mann et al., *Cell,* 1983, 33:153; U.S. Pat. Nos. 4,650,764 and 4,980,289; Markowitz et al., *J. Virol.,* 1988, 62:1120; U.S. Pat. No. 5,124,263; European Publication Nos. EP 453 242 and EP178 220; Bernstein et al., *Genet. Eng.,* 1985, 7:235; McCormick, *BioTechnology,* 1985, 3:689; PCT Publication No. WO 95/07358; and Kuo et al., *Blood,* 1993, 82:845, each of which is incorporated by reference in its entirety. The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Suitable packaging cell lines have been described in the prior art, in particular the cell line PA317 (U.S. Pat. No. 4,861,719); the PsiCRIP cell line (PCT Publication No. WO 90/02806) and the GP+envAm-12 cell line (PCT Publication No. WO 89/07150). In addition, the recombinant retroviral vectors can contain modifications within the LTRs for suppressing transcriptional activity as well as extensive encapsidation sequences which may include a part of the gag gene (Bender et al., *J. Virol.,* 1987, 61:1639). Recombinant retroviral vectors are purified by standard techniques known to those having ordinary skill in the art.

Retroviral vectors can be constructed to function as infectious particles or to undergo a single round of transfection. In the former case, the virus is modified to retain all of its genes except for those responsible for oncogenic transformation properties, and to express the heterologous gene. Non-infectious viral vectors are manipulated to destroy the viral packaging signal, but retain the structural genes required to package the co-introduced virus engineered to contain the heterologous gene and the packaging signals. Thus, the viral particles that are produced are not capable of producing additional virus.

Retrovirus vectors can also be introduced by DNA viruses, which permits one cycle of retroviral replication and amplifies transfection efficiency (see PCT Publication Nos. WO 95/22617, WO 95/26411, WO 96/39036 and WO 97/19182).

Lentivirus Vectors.

In another implementation of the present invention, lentiviral vectors can be used as agents for the direct delivery and sustained expression of a transgene in several tissue types, including brain, retina, muscle, liver and blood. The vectors can efficiently transduce dividing and nondividing cells in these tissues, and effect long-term expression of the gene of interest. For a review, see, Naldini, Curr. Opin. Biotechnol., 1998, 9:457-63; see also Zufferey, et al., *J. Virol.*, 1998, 72:9873-80). Lentiviral packaging cell lines are available and known generally in the art. They facilitate the production of high-titer lentivirus vectors for gene therapy. An example is a tetracycline-inducible VSV-G pseudotyped lentivirus packaging cell line that can generate virus particles at titers greater than 106 IU/mL for at least 3 to 4 days (Kafri, et al., *J. Virol.*, 1999, 73: 576-584). The vector produced by the inducible cell line can be concentrated as needed for efficiently transducing non-dividing cells in vitro and in vivo.

Non-Viral Vectors.

In another implementation of the present invention, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Feigner, et. al., Proc. Natl. Acad. Sci. U.S.A., 1987, 84:7413-7417; Feigner and Ringold, Science, 1989, 337:387-388; see Mackey, et al., *Proc. Natl. Acad. Sci. U.S.A.,* 1988, 85:8027-8031; Ulmer et al., *Science,* 1993, 259:1745-1748). Useful lipid compounds and compositions for transfer of nucleic acids are described in PCT Patent Publication Nos. WO 95/18863 and WO 96/17823, and in U.S. Pat. No. 5,459,127. Lipids may be chemically coupled to other molecules for the purpose of targeting (see Mackey, et. al., supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., PCT Patent Publication No. WO 95/21931), peptides derived from DNA binding proteins (e.g., PCT Patent Publication No. WO 96/25508), or a cationic polymer (e.g., PCT Patent Publication No. WO 95/21931).

It is also possible to introduce the vector in vivo as a naked DNA plasmid. Naked DNA vectors for vaccine purposes or gene therapy can be introduced into the desired host cells by methods known in the art, e.g., electroporation, microinjection, cell fusion, DEAE dextran, calcium phosphate precipitation, use of a gene gun, or use of a DNA vector transporter (e.g., Wu et al., *J. Biol. Chem.,* 1992, 267:963-967; Wu and Wu, *J. Biol. Chem.,* 1988, 263:14621-14624; Canadian Patent Application No. 2,012,311; Williams et al., Proc. Natl. Acad. Sci. USA, 1991, 88:2726-2730). Receptor-mediated DNA delivery approaches can also be used (Curie) et al., *Hum. Gene Ther.,* 1992, 3:147-154; Wu and Wu, *J. Biol. Chem.,* 1987, 262:4429-4432). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir et al., *C.P. Acad. Sci.,* 1988, 321:893; PCT Publication Nos. WO 99/01157; WO 99/01158; WO 99/01175). Accordingly, additional embodiments of the present invention relates to a method of inducing an immune response in a human comprising administering to said human an amount of a DNA molecule encoding a 2086 polypeptide of this invention, optionally with a transfection-facilitating agent, where said polypeptide, when expressed, retains immunogenicity and, when incorporated into an immunogenic composition and administered to a human, provides protection without inducing enhanced disease upon subsequent infection of the human with *Neisseria* sp. pathogen, such as *N. meningitidis*. Transfection-facilitating agents are known in the art and include bupivicaine, and other local anesthetics (for examples see U.S. Pat. No. 5,739,118) and cationic polyamines (as published in International Patent Application WO 96/10038), which are hereby incorporated by reference.

The present invention also relates to an antibody, which may either be a monoclonal or polyclonal antibody, specific for 2086 polypeptides as described above. Such antibodies may be produced by methods that are well known to those skilled in the art.

Bacterial Expression Systems and Plasmids

This invention also provides a recombinant DNA molecule, such as a vector or plasmid, comprising an expression control sequence having promoter sequences and initiator sequences and a nucleotide sequence which codes for a polypeptide of this invention, the nucleotide sequence being located 3' to the promoter and initiator sequences. In yet another aspect, the invention provides a recombinant DNA cloning vehicle capable of expressing a 2086 polypeptide comprising an expression control sequence having promoter sequences and initiator sequences, and a nucleotide sequence which codes for a 2086 polypeptide, the nucleotide sequence being located 3' to the promoter and initiator sequences. In a further aspect, there is provided a host cell containing a recombinant DNA cloning vehicle and/or a recombinant DNA molecule as described above. Suitable expression control sequences and host cell/cloning vehicle combinations are well known in the art, and are described by way of example, in Sambrook et al. (1989).

Once recombinant DNA cloning vehicles and/or host cells expressing a desired a polypeptide of this invention have been constructed by transforming, transfecting or infecting such cloning vehicles or host cells with plasmids containing the corresponding 2086 polynucleotide, cloning vehicles or host cells are cultured under conditions such that the polypeptides are expressed. The polypeptide is then isolated substantially free of contaminating host cell components by techniques well known to those skilled in the art.

The following examples are included to demonstrate preferred embodiments of the invention. It should be appreciated by those skilled in the art that the techniques disclosed in the examples which follow represent techniques discovered by the inventors to function well in the practice of the invention, and thus can be considered to constitute preferred modes for its practice. However, those of skill in the art should, in view of the present disclosure, appreciate that many changes can be made in the specific embodiments which are disclosed and still obtain a like or similar result without departing from the spirit and scope of the invention.

EXAMPLES

Example 1

Identification of a Neisserial Membrane Protein Extract Capable of Eliciting Bactericidal Antibodies Against Heterologous Strains Referring to Table II below, LOS (lipid oligosacharnide)-depleted outer membrane protein preparations have been shown to elicit bactericidal antibodies. These antibodies are often directed towards the PorA of the respective strain. LOS-depleted outer membrane preparations from serogroup B meningococcal strain 8529 (B:15:P1.7b,3) are unusual in this manner because they unexpectedly elicit bactericidal antibodies to several heterologous strains.

TABLE II

BC ACTIVITY OF ANTI-SOMPS AGAINST DIFFERENT STRAINS OF *N. MENINGITIDIS*

| | Anti-serum Week 6 | | | | | | |
|---|---|---|---|---|---|---|---|
| | H44/76 | 5315 | H355 | M982 | 880049 | 8529* | NMB |
| | | | | Serosubtype | | | |
| | P1.7,16 | P1.5 | P1.15 | P1.9 | P1.4 | P1.3 | P1.5,2 |
| sOMPs H44/76 25 µg QS-21 20 µg | 1,000 | <50 | <50 | <50 | <50 | 980 | <50 |
| sOMPs 5315 25 µg QS-21 20 µg | 50 | <50 | <50 | <50 | <50 | 2170 | <50 |
| sOMPs H355 25 µg QS-21 20 µg | <50 | <50 | 450 | <50 | <50 | 860 | <50 |
| sOMPs M982 25 µg QS-21 20 µg | 92 | <50 | <50 | 300 | <50 | 1100 | <50 |
| sOMPs 880049 25 µg QS-21 20 µg | 50 | <50 | <50 | <50 | <50 | 1190 | <50 |
| sOMPs 8529 25 µg QS-21 20 µg | 1,000 | <50 | 450 | 50 | 215 | >4050 (81.7) | <50 |
| sOMPs 2996 25 µg QS-21 20 µg | <50 | <50 | <50 | <50 | <50 | 790 | 148 |
| Whole-cell control serum 25 µg 3DMPL 25 µg | 450 | 50 | 100 | 500 | 150 | >1350 (66.0) | 952 |

To facilitate the isolation and characterization of the antigen(s) responsible for eliciting heterologous bactericidal antibodies, we sought to identify which detergent optimally extracted the antigen(s)

Strains and Culture Conditions.

*N. meningitidis* strain 8529 from a frozen vial was streaked onto a GC plate. (The meningococcal strain 8529 was received from The RIVM, Bilthoven, The Netherlands). The plate was incubated at 36 C/5% $CO_2$ for 7.5 hours. Several colonies were used to inoculate a flask containing 50 mL of modified Frantz medium+GC supplement. The flask was incubated in an air shaker at 36° C. and agitated at 200 RPM for 4.5 hours. 5 mL was used to inoculate a Fernbach flask containing 450 mL of modified Frantz medium+GC supplement. The flask was incubated in an air shaker at 36° C. and agitated at 100 RPM for 11 hours. The entire 450 mL was used to inoculate 8.5 L of modified Frantz medium+GC supplement in a 10 L fermentor.

Composition of Modified Frantz Medium:

| | |
|---|---|
| Glutamic acid | 1.3 g/L |
| Cysteine | 0.02 |
| Sodium phosphate, dibasic, 7 hydrate | 10 |
| Potassium chloride | 0.09 |
| Sodium chloride | 6 |
| Ammonium chloride | 1.25 |
| Dialyzed yeast extract (YE) | 40 ml |
| (25% YE soln. dialyzed against 5 volumes of $dH_2O$ overnight, then autoclaved) | |
| GC supplement 100X, filter sterilize | |
| Dextrose | 400 g/L |
| Glutamic acid | 10 |
| Cocarboxylase | 0.02 |
| Ferric nitrate | 0.5 |

The following parameters were controlled during fermentation: Temperature=36° C.; pH=7.4; Dissolved Oxygen=20%. Several drops of P-2000 antifoam were added to control foaming. The culture was grown to stationary phase. Cells were harvested by centrifugation at OD650=5.25. A total of 100-300 grams of wet cell paste is typically harvested from ~8.5 L of culture.

Partial Purification of Outer Membrane Protein Fractions from Meningococci which Elicit Heterologous Bactericidal Antibodies:

100 gms wet weight of cells were suspended, to a volume five times the wet weight, with 10 mM HEPES-NaOH, pH 7.4, 1 mM Na2EDTA and lysed by passage through a 110Y microfluidizer equipped with a chamber at ~18,000 psi. The cell lysate was clarified and the cell envelope isolated by centrifugation at 300,000×g for 1 hour at 10° C. The cell envelopes were washed 2× with the same buffer by suspension with a homogenizer followed by centrifugation as above. The cell envelopes were then extracted with 320 mL of 1% (w/v) TRITON X-100 in 10 mM HEPES-NaOH, pH 7.4, 1 mM $MgCl_2$. Referring to Table III below, results from sequential differential detergent extractions using TRITON X-100 and ZWITTERGENT 3-14 followed by immunization of mice, allowed us to determine that the TRITON extracts optimally extracted the candidate(s) of interest. This TRITON X-100 extract, eliciting bactericidal antibody response against four out of five strains listed in Table III, was then fractionated by preparative isoelectric focusing (IEF) in a BioRad Rotophor unit. Ampholyte concentrations were 1% pH 3-10 mixed with 1% pH 4-6. As shown in Table III, several fractions were found to elicit a heterologous bactericidal response. The fractions obtained from IEF, which focused in the pH range of 5.5-7.8, elicited a heterologous response to the most strains as determined by the bactericidal assay. The pooled IEF fractions were concentrated and the ampholytes removed by ethanol precipitation. A further purification was achieved by adsorbing some of the proteins obtained in the pH range of about 5.5-7.8 on an anion exchange column and comparing the bactericidal activity obtained after immunizing mice with the adsorbed and unadsorbed proteins. Referring again to Table II, while many proteins were adsorbed to the anion exchange resin, the proteins that were not adsorbed by the column elicited more heterologous bactericidal antibodies.

TABLE III

| | | BC$_{50}$ TARGET STRAIN | | | | |
|---|---|---|---|---|---|---|
| Method | Fraction | H44/76 | 880049 | H355 | 539* | M982 |
| LOS-DEPLETED DETERGENT Extractions | sOMPs | 1,000 | 215 | 450 | NC | 50 |
| | CYTOPLASMIC EXTRACT | 200 | NT | NT | NT | NT |
| | TX-100 | >800 | >800 | >800 | >800 | <25 |
| | ZWITTERGENT 3-12 | 400 | >25 | 100 | 400 | <25 |
| | ZWITTERGENT 3-14 | <25 | NT | NT | NT | NT |
| | Zw.3-14 + NaCl | <25 | NT | NT | NT | NT |
| | SARCOSYL | <25 | NT | NT | NT | NT |
| | Zw.3-14 + heat | <25 | NT | NT | NT | NT |
| Preparative IEF | Fractions 1-3 (pH 2.3-3.9) | 50 | NT | NT | NT | NT |
| | Fraction 4 (pH 4.1) | >800 | <25 | 100 | <25 | NT |
| | Fraction 5 (pH 4.3) | >800 | <25 | 100 | 200 | NT |
| | Fraction 6 (pH 4.5) | 400 | NT | NT | NT | NT |
| | Fraction 7 (pH 4.8) | <25 | NT | NT | NT | NT |
| | Fractions 8-9 (pH 5.0-5.3) | <25 | NT | NT | NT | NT |
| | Fractions 10-17 (pH 5.5-7.8) | >800 | 200 | <800 | <800 | NT |
| Anion Exchange | Adsorbed | 400 | NT | 100 | 100 | NT |
| | Unadsorbed | >6,400 | NT | <800 | <800 | NT |

NT: not tested
*Clinical isolate 539 is a homologous strain to 8529, isolated from the same outbreak As shown in FIG. 1A, two major proteins were present in the unadsorbed fraction as determined by SDS-PAGE. To identify these proteins, two types of analysis were performed. One analysis was to perform limited proteolytic degradation (See FIG. 1A, and FIG. 1B) followed by isolation of peptides and direct protein sequencing. The other analysis was to perform SDS-PAGE followed by gel excision, proteolytic digestion, and LC-MS/MS (Liquid Chromatography tandem Mass Spectrometry), (see FIG. 3) to obtain mass spectral information on the components of the preparations of interest. (See peptide mapping and sequencing methods described later in this section)

The N. meningitidis A Sanger genomic sequence was analyzed using the methods and algorithms described in Zagursky and Russell, 2001, BioTechniques, 31:636-659. This mining analysis yielded over 12,000 possible Open Reading Frames (ORFs). Both the direct sequence data and the mass spectral data described above indicated that the major components of the unadsorbed fraction were the products of several ORFs present in an analysis of the Sanger database. The three predominant proteins identified by this methodology correspond to ORFs 4431, 5163 and 2086, (see FIGS. 1B and 3).

Although ORF 4431 was the most predominant protein identified in the fractions, mouse antibodies to recombinant lipidated 4431 were not bactericidal and did not provide a protective response in an animal model. Additional analysis of ORF 5163 is in progress.

The second most predominant component of the preparations described herein corresponds to the product of ORF 2086.

Immunogenicity Methods:
Preparation of Antisera:

Except where noted, protein compositions/vaccines were formulated with 25 µg of total protein and were adjuvanted with 20 µg QS-21. A 0.2 mL dose was administered by subcutaneous (rump) injection to 6-8 week old female Swiss-Webster mice at week 0 and 4. Bleeds were collected at week 0 and 4, and a final exsanguination bleed was performed on week 6.

Bactericidal Assay:

Bactericidal assays were performed essentially as described (See Mountzouros and Howell, 2000, J. Clin. Microbiol. 38(8):2878-2884). Complement-mediated antibody-dependent bactericidal titers for the SBA were expressed as the reciprocal of the highest dilution of test serum that killed 50% of the target cells introduced into the assays (BC$_{50}$ titer).

Methods used to identify 2086 protein:
Cyanogen Bromide Cleavage and Direct Sequencing of Fragments:

Cyanogen Bromide cleavage of Anion Exchange Unadsorbed Fraction (AEUF). The AEUF was precipitated with 90% cold ethanol and was solubilized with 10 mg/mL cyanogen bromide in 70% formic acid to a protein concentration of 1 mg/mL. The reaction was performed overnight at room temperature in the dark. The cleaved products were dried down by speed vacuum, and the pellet was solubilized with HE/0.1% reduced TX-100. SDS-PAGE followed by N-terminal amino acid sequencing was used to identify the components of this fraction.

Protease Digestion/Reverse Phase/N-Terminal Sequencing to Identify Components:

The AEUF was digested with GluC (V8), LysC or ArgC. The protein to enzyme ratio was 30 µg protein to 1 µg enzyme. The digestion was carried out at 37° C. overnight. The digested protein mixture (30 µg) was passed over a seven micron Aquapore RF-300 column and was eluted with a gradient of 10-95% acetonitrile in 0.1% trifluoroacetic acid, and peaks were collected manually. A no protein blank was also run, and the peaks from this were subtracted from the sample chromatogram. Peaks occurring only in the sample run were analyzed by mass spectrometer, and those samples giving a clear mass were analyzed for N-terminal amino acid sequencing.

N-Terminal Amino Acid Sequencing:

For bands excised from a blot, the protein sample was transferred from an SDS gel to a PVDF membrane, stained with AMIDO BLACK (10% acetic acid, 0.1% amido black in deionized water) and destained in 10% acetic acid. The desired protein band was then excised from all ten lanes using a methanol cleaned scalpel or mini-Exacto knife and placed in the reaction cartridge of the Applied Biosystems 477A Protein Sequencer. For direct sequencing of samples in solution, the Prosorb cartridge was assembled and the PVDF wetted with 60 µL of methanol. The PVDF was rinsed with 50 µL of deionized water and the sample (50 µL) was loaded to the PVDF. After 50 µL of deionized water was used to rinse the sample, the Prosorb PVDF was punched out, dried, and placed in the reaction cartridge of the Applied Biosystems 477A Protein Sequencer. For both methods, the Applied Biosystems N-terminal Sequencer was then run under optimal blot conditions for 12 or more cycles (1 cycle Blank, 1 cycle Standard, and 10 or more cycles for desired residue identification) and PTH-amino acid detection was done on the Applied Biosystems 120A PTH Analyzer. The cycles were collected both on an analog chart recorder and digitally via the instrument software. Amino acid assignment was done using the analog and digital data by comparison of a standard set of PTH-amino acids and their respective retention times on the analyzer (cysteine residues were destroyed during conversion and were not detected). Multiple sequence information can be obtained from a single residue and primary versus secondary assignments were made based on signal intensity.

LC-MS/MS

Protein samples purified by IEF were further analyzed by SDS-polyacrylamide gel electrophoresis. Proteins were visualized by Coomaasie blue staining, and bands of interest were excised manually, then reduced, alkylated and digested with trypsin (Promega, Madison, Wis.) in situ using an automated in-gel tryptic digestion robot (1). After digestion, peptide extracts were concentrated to a final volume of 10-20 μL using a Savant SpeedVac Concentrator (ThermoQuest, Holdbrook, N.Y.).

Peptide extracts were analyzed on an automated microelectrospray reversed phase HPLC. In brief, the microelectrospray interface consisted of a Picofrit fused silica spray needle, 50 cm length by 75 um ID, 8 um orifice diameter (New Objective, Cambridge Mass.) packed with 10 um C18 reversed-phase beads (YMC, Wilmington, N.C.) to a length of 10 cm. The Picofrit needle was mounted in a fiber optic holder (Melles Griot, Irvine, Calif.) held on a home-built base positioned at the front of the mass spectrometer detector. The rear of the column was plumbed through a titanium union to supply an electrical connection for the electrospray interface. The union was connected with a length of fused silica capillary (FSC) tubing to a FAMOS autosampler (LC-Packings, San Francisco, Calif.) that was connected to an HPLC solvent pump (ABI 140C, Perkin-Elmer, Norwalk, Conn.). The HPLC solvent pump delivered a flow of 50 μL/min which was reduced to 250 nL/min using a PEEK microtight splitting tee (Upchurch Scientific, Oak Harbor, Wash.), and then delivered to the autosampler using an FSC transfer line. The LC pump and autosampler were each controlled using their internal user programs. Samples were inserted into plastic autosampler vials, sealed, and injected using a 5 μL sample loop.

Figure 3:
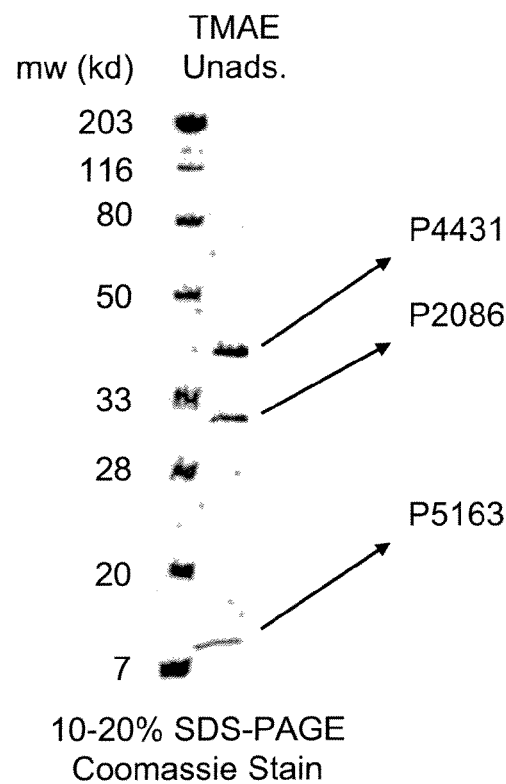
FIG. 3 depicts the results from the experiments from the identification of the two major proteins and one minor protein by analysis of TMAE Flow Through components by LC-MS/MS and the corresponding SDS-PAGE.

Microcapillary HPLC-Mass Spectrometry:

Extracted peptides from in-gel digests were separated by the microelectrospray HPLC system using a 50 minute gradient of 0-50% solvent B (A: 0.1M HOAc, B: 90% MeCN/0.1M HOAc). Peptide analyses were done on a Finnigan LCQ ion trap mass spectrometer (ThermoQuest, San Jose, Calif.) operating at a spray voltage of 1.5 kV, and using a heated capillary temperature of 150° C. Data were acquired in automated MS/MS mode using the data acquisition software provided with the instrument. The acquisition method included 1 MS scan (375-1200 m/z) followed by MS/MS scans of the top 3 most abundant ions in the MS scan. The dynamic exclusion and isotope exclusion functions were employed to increase the number of peptide ions that were analyzed (settings: 3 amu=exclusion width, 3 min=exclusion duration, 30 secs=pre-exclusion duration, 3 amu=isotope exclusion width). Automated analysis of MS/MS data was performed using the SEQUEST computer algorithm incorporated into the Finnigan Bioworks data analysis package (ThermoQuest, San Jose, Calif.) using the database of proteins derived from the complete genome of *N. meningitidis* (from Sanger). The results of the study are illustrated in FIG. 3.

Example 2

Cloning of Recombinant Lipidated P2086 (RLP2086)

A.) Native Leader Sequence:
Source Materials:

The ORF 2086 gene was amplified by PCR from a clinical isolate of a serogroup B *Neisseria meningitidis* strain designated 8529. The serogroup, serotype and serosubtype of this strain is shown in parentheses; 8529 (B:15, P1:7b,3). This meningococcal strain was received from The RIVM, Bilthoven, The Netherlands.

PCR Amplification and Cloning Strategy:

A visual inspection of ORF 2086 indicated that this gene had a potential lipoprotein signal sequence. Additional analysis using a proprietary Hidden Markov Model Lipoprotein algorithm confirmed that ORF 2086 contains a lipoprotein signal sequence. In order to recombinantly express P2086 in a more native-like conformation, oligonucleotide primers were designed to amplify the full length gene with the lipoprotein signal sequence intact and were based on an analysis of the Sanger sequence for *N. meningitidis* A ORF 2086. The 2086 gene was amplified by polymerase chain reaction (PCR) [ABI 2400 thermal cycler, Applied Biosystems, Foster City, Calif.] from *N. meningitidis* strain 8529. The correct size amplified product was ligated and cloned into pCR2.1-TOPO (Invitrogen). The plasmid DNA was restriction digested with NdeI and BamHI, gel purified and ligated into pET-27b(+) vector (Novagen).

Figure 4:
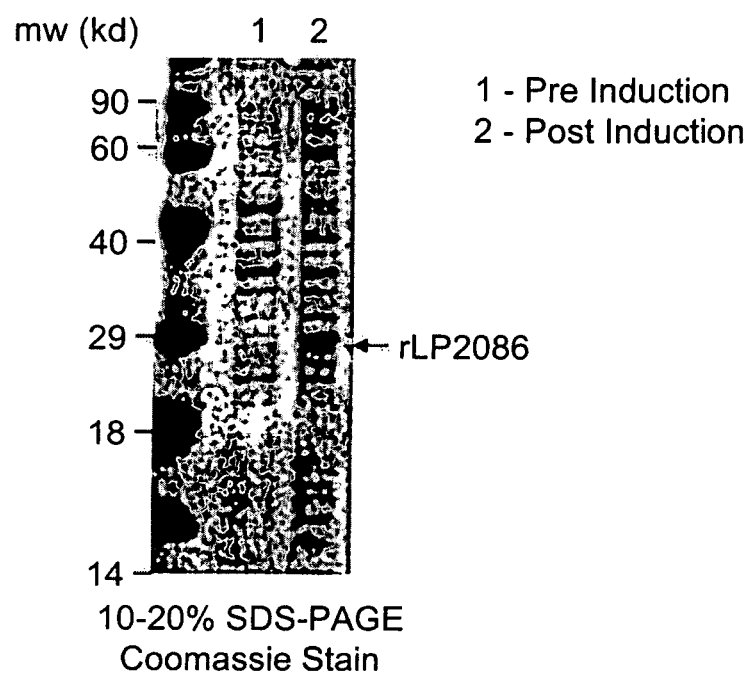
FIG. 4 is an SDS-PAGE gel from the recombinant expression of 2086 protein.
Figure 5:
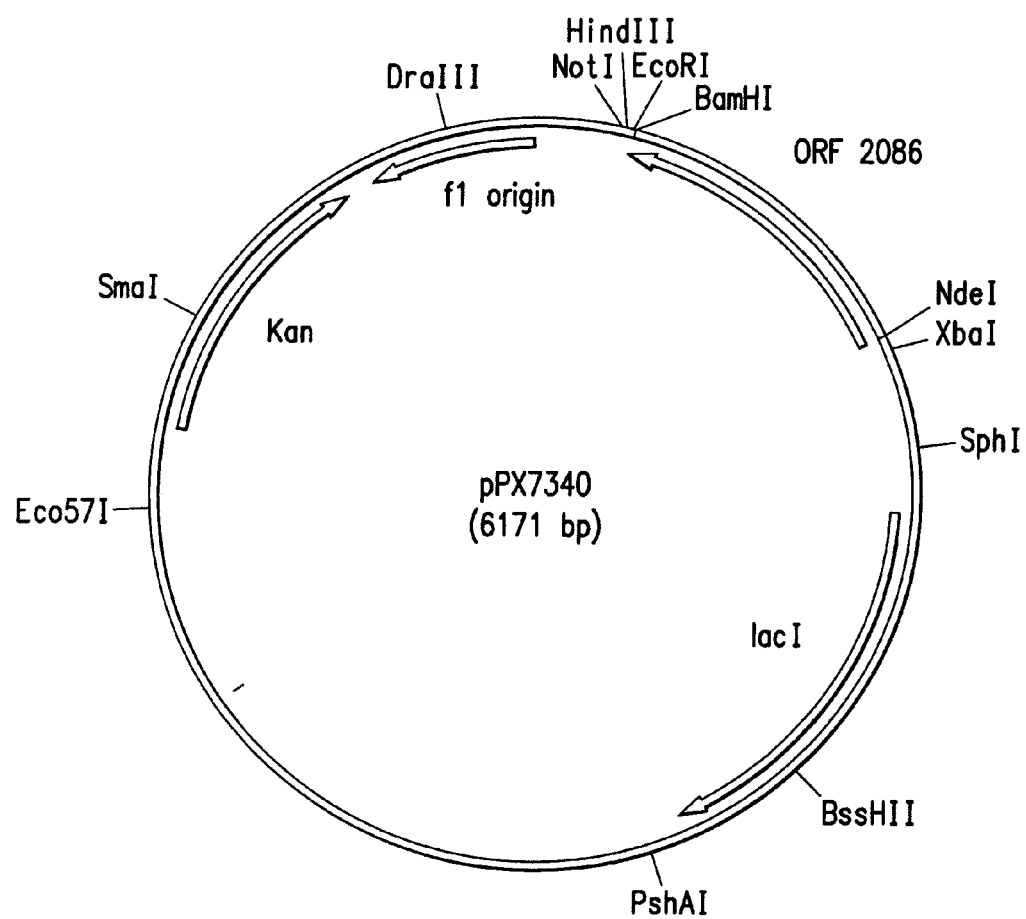
FIG. 5 is a schematic diagram of plasmid pPX7340, as described in the examples herein.

Oligonucleotide primers described herein, were synthesized on a PerSeptive Biosystems oligonucleotide synthesizer, Applied Biosystems, Foster City Calif., using β-Cyanoethylphosphoramiditechemistry, Applied Biosystems, Foster City Calif.

rLP2086 Lipoprotein Expression Utilizing Native Leader Sequence:

Referring to FIG. 5, plasmid pPX7340 was transformed/transfected or infected into BLR(DE3) pLysS host cells (Life Sciences). One transformant was selected and inoculated into 50 mL of Terrific Broth containing 2% glucose, kanamycin (30 μg/mL), chloramphenicol (30 μg/mL), and tetracycline (12 μg/mL). The OD600 for the overnight culture was 6.0. The overnight culture was diluted out in 1 liter of Terrific Broth with 1% glycerol and the same antibiotics. The starting OD600 was 0.4. After 2 hours the OD600 was 1.6 and a pre-induced sample was taken. Cells equivalent to an OD600=1 were centrifuged and the supernatant was removed. The whole cell pellet was resuspended in 150 μL Tris-EDTA buffer and 150l of 2×SDS-PAGE sample buffer. IPTG was added to a final concentration of 1 mM. After 3.5 hours a post-induced sample was taken as described and analyzed on SDS-PAGE (See FIG. 4).

Purification of rLP2086:

The rLP2086 was solubilized from *E. coli* following differential detergent extraction. Unlike the P2086 in its native environment, the rLP2086 was not significantly solubilized by TRITON X-100 or ZWITTERGENT 3-12. The bulk of the rLP2086 was solubilized with sarcosyl, indicating that it interacts with the outer membrane components of *E. coli* differently than it does in *N. meningitidis*. Once solubilized the rLP2086 was purified similarly to the native protein in that many of the contaminating *E. coli* proteins could be removed by adsorbtion to an anion exchange resin at pH 8. Despite being greater than one half a pH unit above its theoretical pI, the rLP2086 remained unadsorbed at pH 8. Further purification was achieved by adsorbtion of the rLP2086 to a cation exchange resin at pH 4.5.

Figure 2:
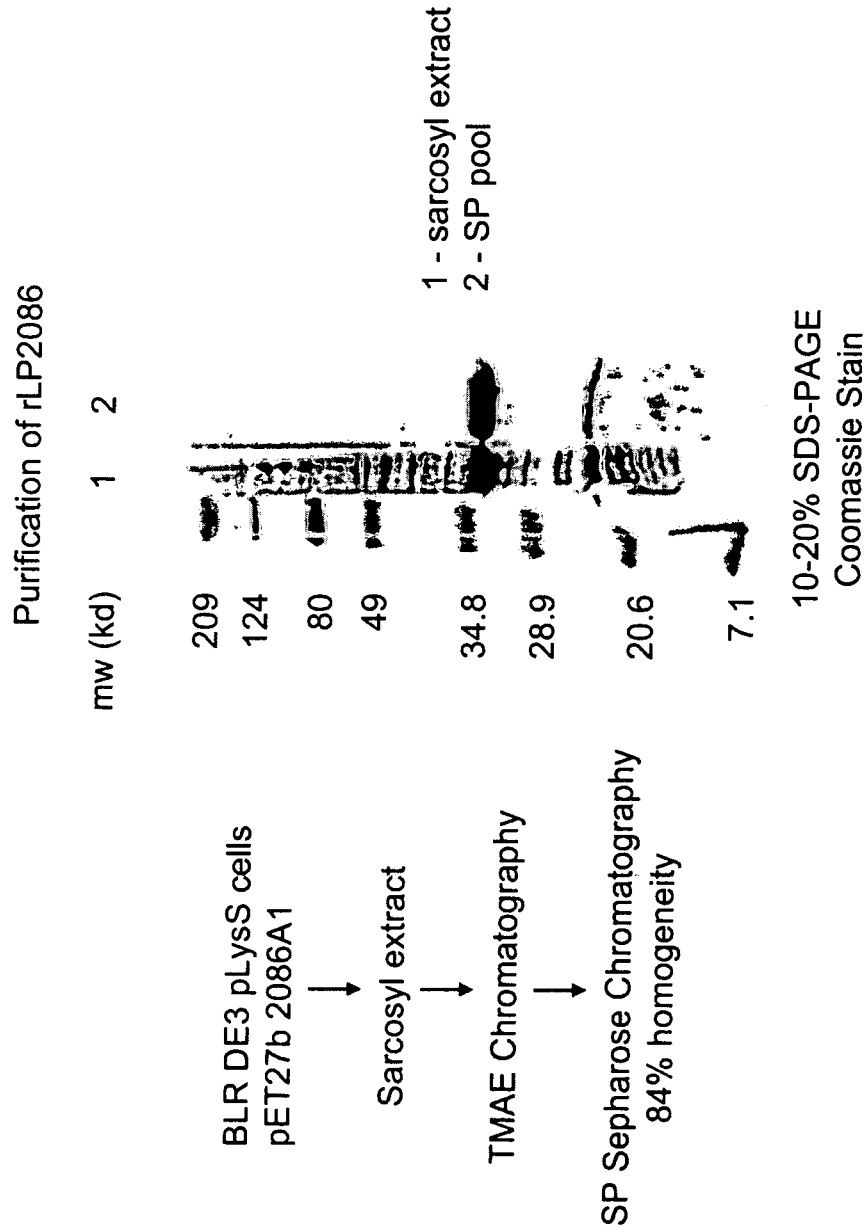
FIG. 2 depicts the purification scheme and homogeneity as determined by SDS-PAGE of rLP2086.

The homogeneity of the rLP2086 is shown in FIG. 2 following SDS-PAGE. The mass of rLP2086 was determined by MALDI-TOF mass spectral analysis to be 27,836. This mass differs from the theoretical mass of 27,100 by 736, which approximates the mass of the N-terminal lipid modification common to bacterial lipoproteins. Both native and rLP2086 appear to be outer membrane lipoproteins. Attempts with N-terminal sequencing were blocked and this is consistent with the terminal modification.

Purification Methods:

Frozen pellets of BLR DE3 pLysS cells expressing P2086 were resuspended in 10 mM HEPES-NaOH/1 mM EDTA/1 μg/mL Pefabloc SC protease inhibitor (Roche) pH 7.4 (HEP) at 20 mL/g wet cell weight and lysed by microfluidizer (Microfluidics Corporation Model 110Y). The cell lysate was centrifuged at 150,000×g for one hour. The pellet was washed twice with HEP and centrifuged twice, and the resulting membrane pellet was frozen overnight. The pellet was solubilized with 10 mM HEPES-NaOH/1 mM MgCl2/1% TX-100 pH 7.4 for 30 minutes, followed by centrifugation at 150,000×g for 30 minutes. This was repeated three times. The membrane pellet was washed as above twice with 50 mM Tris-HCl/5 mM EDTA/1% ZWITTERGENT 3-12 pH 8, followed by two washes each of 50 mM Tris-HCl/5 mM EDTA/1% ZWITTERGENT 3-14 pH 8 and 50 mM Tris-HCl/5 mM EDTA/1% ZWITTERGENT 3-14/0.5M NaCl pH 8.

The rLP2086 was then solubilized with 50 mM Tris-HCl/5 mM EDTA/1% sarcosyl pH 8. This sarcosyl extract was adjusted to 1% ZWITTERGENT 3-14 (Z3-14) and dialyzed twice against a 30 fold excess of 50 mM Tris-HCl/5 mM EDTA/1% Z3-14. The dialyzed rLP2086 extract was precipitated with 90% ethanol to remove remaining sarcosyl, and solubilized with 50 mM Tris-HCl/5 mM EDTA/1% Z3-14 pH 8 (TEZ). Insoluble material was removed by centrifugation, the supernatant was passed over an anion exchange chromatography column, and rLP2086 was collected in the unbound fraction. The unbound material was then dialyzed twice against a 30 fold excess of 25 mM NaAc/1% Z3-14 pH 4.5, and passed over a cation exchange chromatography column. The rLP2086 was eluted with a 0-0.3M NaCl gradient and analyzed by SDS-PAGE (COOMASSIE stain). The rLP2086 pool was determined to be 84% pure by laser densitometry.

Surface Reactivity and Bactericidal Activity of Antisera to rLP2086 Subfamily B.

Referring to Table VII, antisera to purified rLP2086 from the Subfamily B strain 8529, demonstrated surface reactivity to all ten 2086 Subfamily B strains tested by whole cell ELISA. Bactericidal activity was detected against nine of ten 2086 Subfamily B strains expressing heterologous serosubtype antigens, PorAs. These strains are representative of strains causing serogroup B meningococcal disease throughout western Europe, the Americas, Australia, and New Zealand. The only strain which was not killed in the bactericidal assay, 870227, reacted strongly with the anti-rLP2086 (Subfamily B) sera by whole cell ELISA, indicating that this strain expresses a protein with epitopes in common to P2086.

The 2086 Subfamily A strains listed in Table VII, were also tested for surface reactivity by whole cell ELISA. Two out of three of these strains appeared to have a very low level of reactivity, indicating that some 2086 Subfamily A strains may not be cross-reactive with antibodies raised to rLP2086 Subfamily B. The PCR amplification procedure used to identify the 2086 Subfamily B gene from strain 8529 was also performed on strains 870446, NMB and 6557. No 2086 Subfamily B PCR amplified product was detected.

Immunogenicity Methods:

Preparation of Antisera:

Vaccines were formulated as described previously in Example 1. However, a 10 μg dose was used.

Whole Cell Enzyme-Linked Immunosorbant Assay (ELISA):

N. meningitidis whole cell suspensions were diluted to an optical density of 0.1 at 620 nm in sterile 0.01M phosphate, 0.137M NaCl, 0.002M KCl (PBS). From this suspension, 0.1 mL were added to each well of Nunc Bac T 96 well plates (Cat#2-69620). Cells were dried on the plates at room temperature for three days, then were covered, inverted and stored at 4° C. Plates were washed three times with wash buffer (0.01 M Tris-HCl, 0.139M NaCl/KCl, 0.1% dodecylpoly(oxyethyleneneglycolether)$_n$ n=23 (BRIJ-35®, available from ICI Americas, Inc., Wilmington, Del.), pH 7.0-7.4). Dilutions of antisera were prepared in PBS, 0.05% TWEEN-20/Azide and 0.1 mL was transferred to the coated plates. Plates were incubated for two hours at 37° C. Plates were washed three times in wash buffer. Goat-anti-mouse IgG AP (Southern Biotech) was diluted at 1:1500 in PBS/0.05% TWEEN-20, 0.1 mL was added to each well, and plates were incubated at 37° C. for two hours. Plates were washed (as above). Substrate solution was prepared by diluting p-nitrophenyl phosphate (Sigma) in 1M diethanolamine/0.5 mM $MgCl_2$ to 1 mg/mL. Substrate was added to the plate at 0.1 mL per well and incubated at room temperature for one hour. The reaction was stopped with 50 μL/well of 3N NaOH and plates were read at 405 nm with 690 nm reference.

B.) P4 Leader Sequence:

PCR Amplification and Cloning Strategy:

In order to optimize rLP2086 expression, the 2086 gene was cloned behind the P4 signal sequence of nontypable *Haemophilus influenzae* (Green et al., 1991). Primers utilized for lipoprotein cloning are listed in Table IV and are identified by compound numbers: 5658, 5660, 6473, 6543 and 6385. ORF 2086 was amplified from *N. meningitidis* B strain 8529 using primers with the following compound numbers 5658 and 5660. ORF 2086 was amplified from *N. meningitidis* serogroup B strain CDC1573 using primers with the following compound numbers 6385 and 5660. ORF 2086 was amplified from *N. meningitidis* serogroup B strain 2996 using primers with the following compound numbers 6473 and 6543. The N-terminal (5') primers were designed to be homologous to the mature region of the 2086 gene (starting at the serine residue at amino acid position 3 just downstream of the cysteine). The restriction site BamHI (GGATTC) was incorporated into the 5' end of each N-terminal primer and resulted in the insertion of a glycine residue in the mature protein at amino acid position 2. The C-terminal (3') primers were designed to be homologous to the C-terminal end of the 2086 gene and included the Stop codon as well as an SphI site for cloning purposes. The amplified fragment from each *N. meningitidis* B strain was cloned into an intermediate vector and screened by sequence analysis.

Plasmid DNA from correct clones was digested with BamHI and SphI restriction enzymes (New England Biolabs, (NEB)). A vector designated pLP339 (supplied by applicants' assignee) was chosen as the expression vector. This vector utilizes the pBAD18-Cm backbone (Beckwith et al., 1995) and contains the P4 lipoprotein signal sequence and P4 gene of nontypable *Haemophilus influenzae* (Green et al., 1991). The pLP339 vector was partially digested with the restriction enzyme BamHI and then subjected to SphI digestion. The amplified 2086 fragments (BamHI/SphI) were each ligated separately into the pLP339 vector (partial BamHI/SphI). This cloning strategy places the mature 2086 gene behind the P4 lipoprotein signal sequence. The BamHI site remains in the cloning junction between the P4 signal sequence and the 2086 gene (See the plasmid construct shown in FIG. 7). The following is an example of the sequence at the BamHI cloning junction:

[P4 signal sequence]—TGT GGA TCC—[remaining 2086 mature nucleic acid sequence]

[P4 signal sequence]—Cys Gly Ser—[remaining 2086 mature amino acid sequence]

Figure 7:
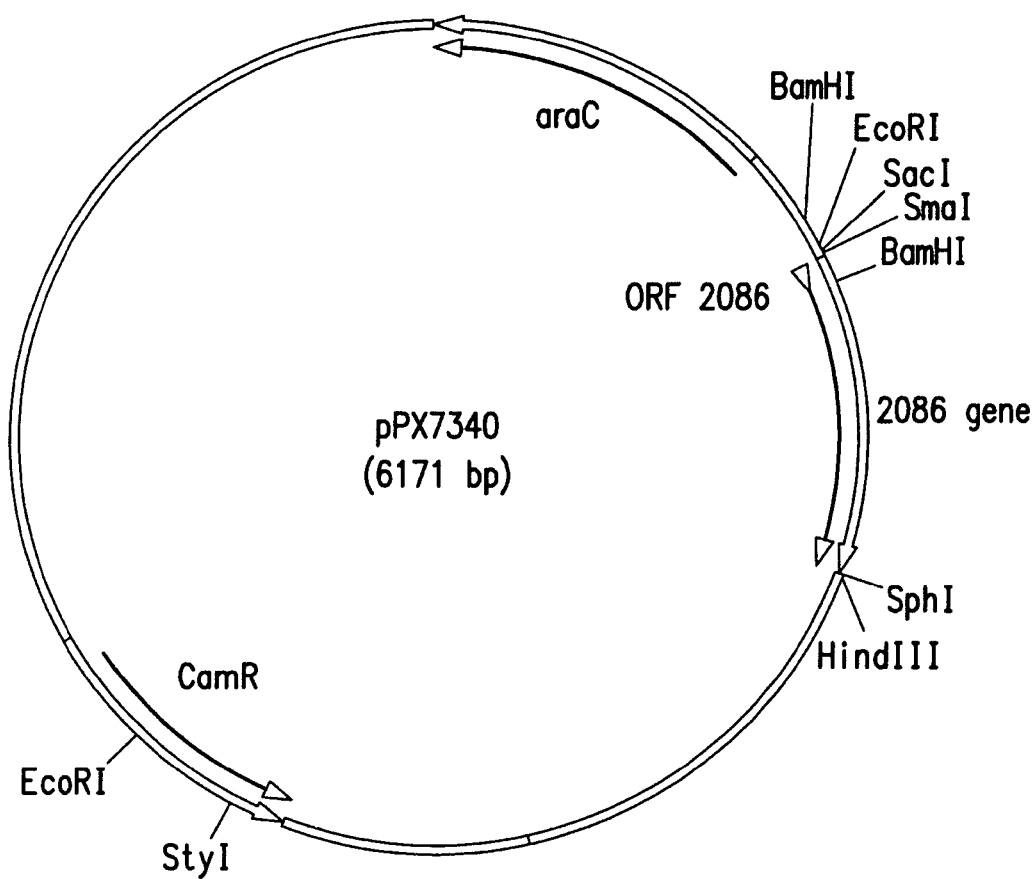
FIG. 7 is a schematic diagram of plasmid pPX7343 as described in the examples herein.
Figure 9A:
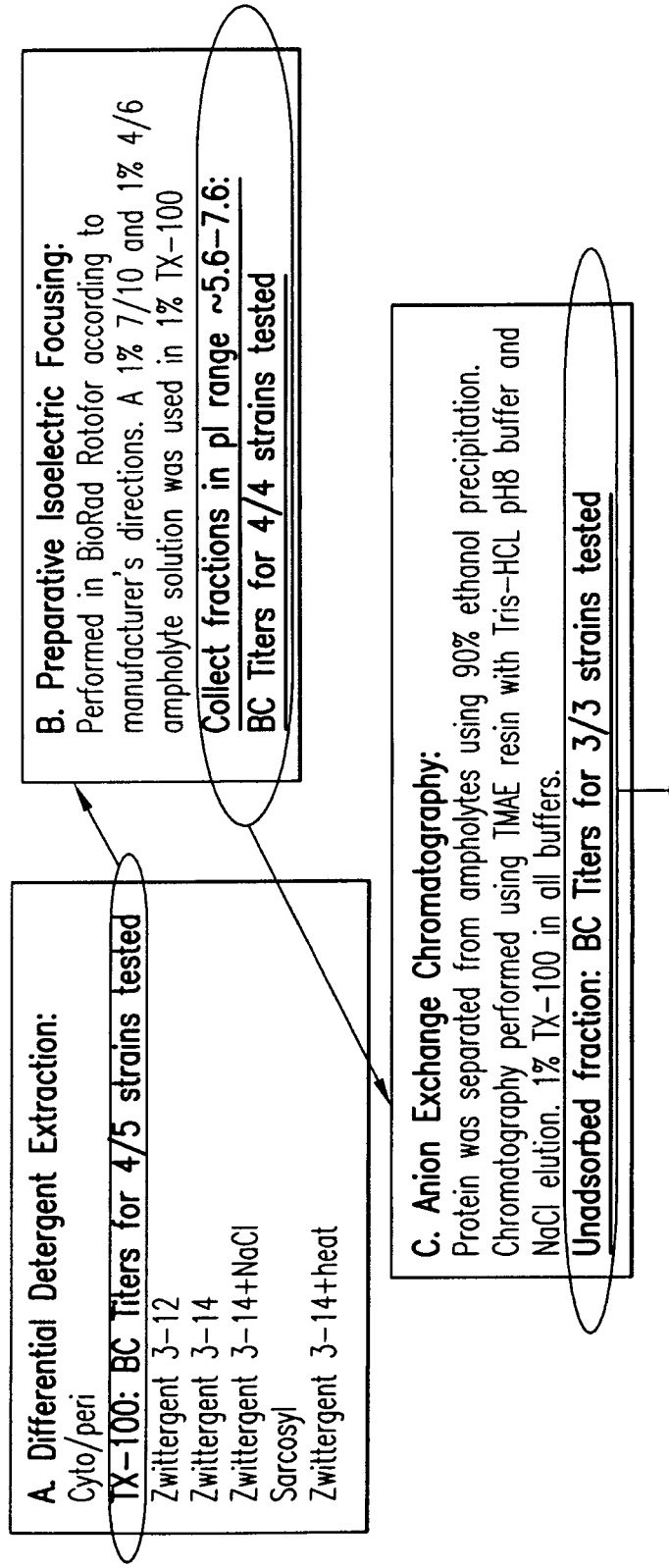
FIG. 9A is a flow chart showing the preliminary steps in the identification of an immunogenic component in a neisserial strain.
Figure 9B:
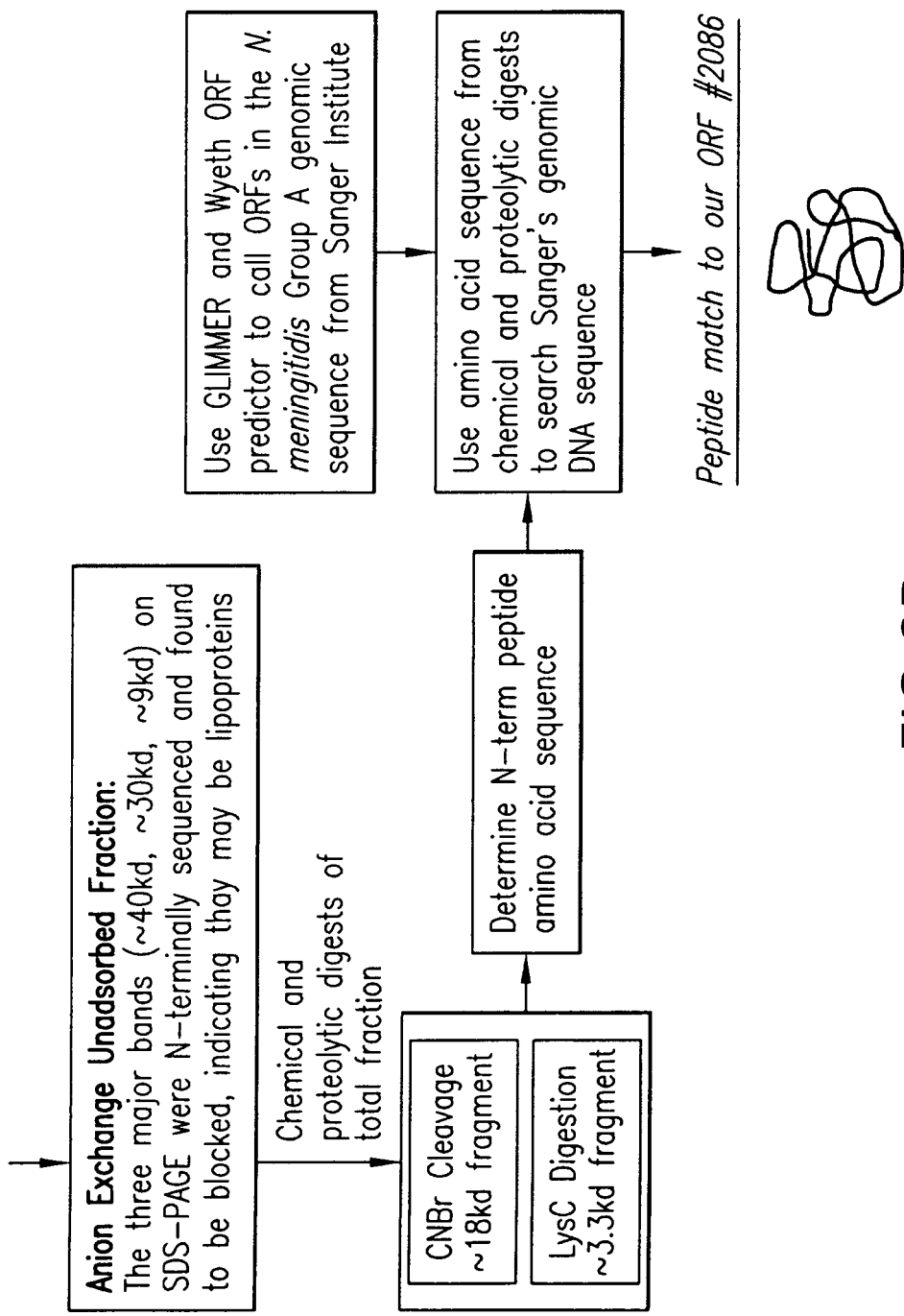
FIG. 9B is a flow chart showing the final steps in the identification of an immunogenic component in a neisserial strain.

Referring to FIG. 7, each amplified fragment was cloned into a modified pBAD18-Cm vector containing the P4 leader sequence. Fermentation was performed on recombinant *E. coli* BLR pPX7343 which expresses rP4LP2086 (recombinant P4 lipidated 2086) to try to increase the cell density by adding additional glucose. The fermentor was filled with 10 L complete M9 Minimal medium, according to Sambrook, supplemented with 1% glucose.

The initial concentration of glucose in the fermentor was 45 g/L. The fermentor was inoculated to initial OD of ~0.25. At ~OD 25, additional 20 g/L glucose was added. The culture was induced with 1% arabinose at glucose depletion at OD 63.4. The fermentation continued until 3 hours after induction. Samples were saved at t=0, 1, 2, 3 post induction and protein quantified using BSA. At t=3, protein yield is ~0.35 g/L, and 7% total cellular protein. A total of 895 grams of wet cell paste was harvested from ~10 L of culture.

Purification of the rP4LP2086 was performed using the same methods as described above in Example 2, section A.

Oligonucleotide primers described herein, were synthesized on a PerSeptive Biosystems oligonucleotide synthesizer, Applied Biosystems, Foster City Calif., using □-Cyanoethylphosphoramidite chemistry, Applied Biosystems, Foster City Calif. The primers used for PCR amplification of the ORF 2086 gene families are listed in Table IV, which shows non-limiting examples of primers of the present invention.

TABLE IV

PRIMERS

| Compound No. | Primer | Restriction sites |
| --- | --- | --- |
| 4623 | Reverse | BamHI |
| 4624 | Forward | NdeI |
| 4625 | Forward | |
| 5005 | Forward | |
| 5007 | Reverse | |
| 5135 | Reverse | BglII |
| 5658 | Forward | BamHI |
| 5660 | Reverse | SphI |
| 6385 | Forward | BamHI |
| 6406 | Forward | BglII and NdeI |
| 6470 | Forward | |
| 6472 | Reverse | |
| 6473 | Forward | BamHI |
| 6474 | Forward | BglII and NdeI |
| 6495 | Forward | |
| 6496 | Reverse | |
| 6543 | Reverse | SphI |
| 6605 | Reverse | BglII |
| 6721 | Forward | BglII and NdeI |

Example 3

Development Genetics for Non-Lipidated Mature 2086 Protein

To further evaluate the immunogenicity of the 2086 protein, cloning and expression of the non-lipidated form of P2086 were performed.
PCR Gene Amplification of the ORF 2086:

The 2086 gene from various stains can be amplified with the primers as described in PCT/US02/32369 (published as WO 03/063766 on Aug. 7, 2003) and PCT/US04/11901 (published as WO 04/094596 on Nov. 4, 2004) which are incorporated herein by reference.

Features of these primers include, a synthetic BglII restriction site in each primer, a synthetic NdeI restriction site in compound numbers 6406 and 6474 and termination codons in all three reading frames are present in compound numbers 5135 and 6605. Primer numbers 6406 and 6474 amplify the 2086 gene with an ATG (Met) fused to the second amino terminal codon (ACG) representing a single amino acid substitution (replaces TGC Cys) of the mature 2086 polypeptide.

The PCR cloning vector was TOPO-PCR2.1, Invitrogen, Valencia, Calif.

The vector used to express non-lipidated 2086 protein was pET9a from Novagen, Madison, Wis.

The *E. coli* cloning strain was Top10, Invitrogen, Carlsbad, Calif.

The *E. coli* expression strain was BLR(DE3)pLysS, Novagen, Madison, Wis.

The culture media for cloning purposes was Terrific Broth liquid or agar, according to Sambrook et al., with 1% sterile glucose substituted for glycerol, and the appropriate antibiotic (ampicillin or kanamycin).

Plasmid purification was with Qiagen Spin Miniprep Kit (Valencia, Calif.).
Preparation of the Production Strain or Cell Line for Non-Lipidated 2086 Expression:

The 2086 gene was amplified by polymerase chain reaction (PCR) [AmpliTaq and ABI 2400 thermal cycler, Applied Biosystems, Foster City, Calif.] from chromosomal DNA derived from meningococcal strain 8529. The PCR amplification of the 2086 gene utilized two oligonucleotide primers in each reaction identified by compound numbers 6474 and 5135. The amplified 2086 PCR product was cloned directly into the TOPO-PCR2.1 cloning vector and selected on Terrific Broth agar supplemented with 100 μg/ml ampicillin and 20 μg/ml X-Gal. White colonies were selected and grown. Plasmid DNA was prepared using a Qiagen miniprep kit and the plasmids were screened for the PCR fragment insert. PCR insert plasmids were subjected to DNA sequencing (Big Dye chemistry on an ABI377 sequencer, Applied Biosystems, Foster City, Calif.).

Plasmids exhibiting the correct DNA sequence were digested with BglII restriction enzyme and the BglII fragment was gel purified using a GeneClean II purification kit (Bio101, Carlsbad, Calif.). The purified BglII fragment was cloned into the BamHI site of the expression vector pET9a. The pET9a/2086 clones were selected on Terrific Broth plates supplemented with 30 μg/ml kanamycin. Kanamycin resistant clones were grown and miniprep plasmid DNA was prepared. The plasmids were screened for the appropriate orientation of the 2086 gene in the BamHI site. Correctly oriented plasmids represent a fusion of the T7-antigen to the amino terminus of 2086 gene (rP2086T7). These rP2086T7 gene fusions were transformed into BLR(DE3)pLysS, selected on Terrific Broth/Kan plates, grown in Terrific Broth and induced to express the rP2086T7 fusion protein with 1 mM IPTG (isopropyl β-D-thiogalactopyranoside). The rP2086T7 fusion protein expressed at high levels.

Figure 6:
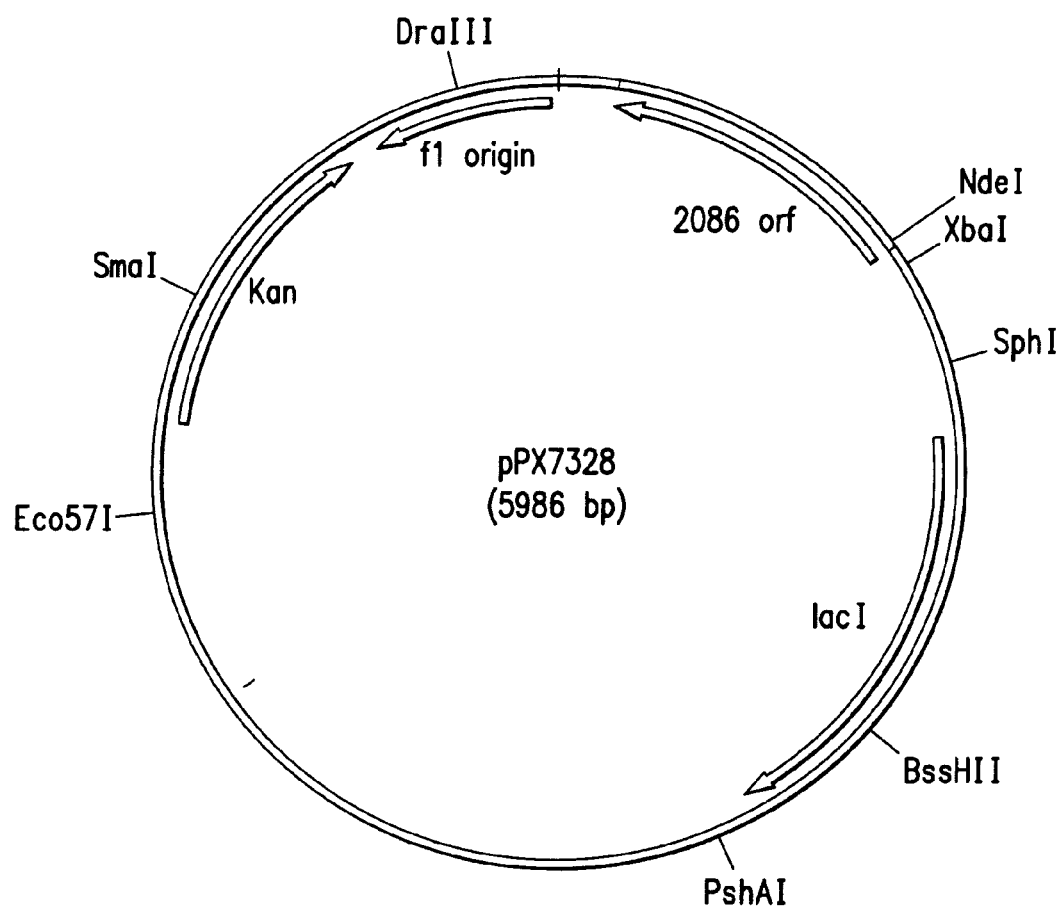
FIG. 6 is a schematic diagram of plasmid pPX7328 as described in the examples herein.

These fusion plasmids were then subjected to a NdeI restriction digest, which deletes the T7-antigen and links the mature 2086 gene directly to the ATG start provided by the vector. These NdeI deleted plasmids were transformed into Top10 cells and selected on Terrific Broth/Kan plates. Candidate clones were grown and miniprep plasmid DNA was prepared. The plasmid DNA was subjected to DNA sequencing to confirm the deletion and the integrity of the 2086 gene sequence. These plasmids are represented by the plasmid map designated pPX7328 (FIG. 6). Plasmids representing the correct DNA sequence were transformed into BLR(DE3)pLysS, selected on Terrific Broth/Kan plates, grown in Terrific Broth and induced to express the 2086 protein with IPTG. The pET9a vector failed to express the mature 2086 protein, in strain BLR(DE3)pLysS, when the T7-Tag was removed.

Production of Non-Lipidated 2086 Protein:

Purified plasmid DNA was used to transform the expression strain BLR(DE3)pLysS. BLR(DE3)pLysS cells carrying the plasmids are resistant to kanamycin and can be induced to express high levels of PorA protein by the addition of 1 mM IPTG. The rP2086T7 fusion protein can be expressed as insoluble inclusion bodies in the E. coli cell line BLR(DE3) pLysS at ~40% of total protein. This purified fusion protein was used to immunize mice and generated significant levels of bactericidal antibodies against a heterologous meningococcal strain. (See Table V)

2086 Non-Lipidated Gene Mutagenesis:

PCR primer mutagenesis was performed on the 5' end of the 2086 gene. Expression studies are under way to determine if the T7-Tag can be removed while exhibiting the high expression levels of mature rP2086T7.

Purification of Non-Lipidated rP2086T7:

E. coli BLR(DE3)pLysS cells expressing non-lipidated rP2086T7 were lysed by microfluidizer in 10 mM Hepes-NaOH/5 mM EDTA/1 mM Pefabloc SC pH 7.4. The cell lysate was then centrifuged at 18,000×g for 30 minutes. The inclusion body pellet was washed three times with 50 mM Tris-HCl/5 mM EDTA/1% TRITON X-100 pH 8 followed by centrifugation each time at 24,000×g for 30 min. The inclusion body pellet was then washed twice with 50 mM Tris-HCl/5 mM EDTA/1% ZWITTERGENT 3-14 pH 8 followed by centrifugation each time at 24,000×g for 15 min. The inclusion body pellet was then solubilized with 50 mM Tris-HCl/5 mM EDTA/4M Urea pH 8 for two hours followed by centrifugation to remove insoluble material. The supernatant (solubilized rP2086T7) was split into four equal samples. One sample was adjusted to 50 mM Tris-HCl/5 mM EDTA/ 250 mM NaCl/2M Urea pH8 (no detergent), one was adjusted to 50 mM Tris-HCl/5 mM EDTA/250 mM NaCl/2M Urea/1% hydrogenated TRITON X-100 pH8 (TX-100), one was adjusted to 50 mM Tris-HCl/5 mM EDTA/250 mM NaCl/2M Urea/1% ZWITTERGENT 3-12 pH8 (Z3-12), and one was adjusted to 50 mM Tris-HCl/5 mM EDTA/250 mM NaCl/2M Urea/1% ZWITTERGENT 3-14 pH8 (Z3-14) using stock solutions. To remove the urea, samples were dialyzed to completion against the respective buffer containing no urea. The samples were then dialyzed to completion against the respective buffer containing no urea and 60 mM NaCl to reduce the NaCl concentration. Insoluble material was removed by centrifugation at 2,000×g for 15 minutes, and the resulting supernatant (refolded rP2086T7) was used for further experiments. Homogeneity of rP2086T7 was found to be 91-95% as determined using COOMASSIE stained SDS-PAGE and laser densitometry.

Immunogenicity Procedure—As described in Example 2

This purified fusion protein was used to immunize mice and generated significant levels of bactericidal antibodies against a heterologous meningococcal strain. (See Table V below):

TABLE V

Bactericidal titers of mouse antibody raised to rP2086T7

| MOUSE SERUM | DESCRIPTION | HETEROLOGOUS STRAIN/H44/76 |
|---|---|---|
| AF780 week 6 | r2086T7, 10 ug | 3200 |
| Week 0 pool | Pre-immune serum | 10 |
| AE203 week 6 | rLP2086, 10 ug (positive control)* | 6400 |

(*positive control sera generated by immunization of mice with rLP2086)

Example 4

Development of Chimeric Clones of ORF 2086

The N-terminal region of the 2086 gene from strain CDC-1573 contains a repeated segment not present in the 2086 gene from strains 8529 and 2996 (see FIG. 8). It appears that this repeated segment is responsible for increased levels of recombinant 2086 protein expression from two E. coli based expression systems (pET and pBAD). The recombinant protein expression level from the CDC-1573 2086 gene was significantly better in the pET and pBAD expression systems as compared to the recombinant expression levels from the 2086 gene with strains 8529 and 2996 using the same systems. The N-terminal region of the 2086 gene from all three strains is relatively homologous, except for this repeated segment. Therefore, it is reasonable to assume that by fusing the CDC-1573 N-terminus to the 2086 genes from strains 8529 and 2996, that the recombinant 2086 protein levels expressed from these genes will increase when using the pET and pBAD systems.

Materials and Methods:

Chromosomal DNA from strains 8529 and 2996 was purified and used as a template for PCR amplification of the chimeric 2086 gene. PCR primers with the compound numbers 6721 and 5135 were used to amplify the chimeric 2086 gene from strain 8529 and PCR primers with the compound numbers 6721 and 6605 were used to amplify the chimeric 2086 gene from strain 2996. The PCR products were cloned directly into the PCR2.1 TOPO vector from Invitrogen and then screened by DNA sequence analysis to identify an intact chimeric 2086 gene. That gene was then cleaved from the PCR2.1 vector with BglII and the BglII fragment was inserted into the BamHI site of the pET9a plasmid. Plasmid inserts were screened for the appropriate orientation and then subjected to an NdeI digestion. The linear NdeI fragments were self-ligated to achieve the deletion of a small NdeI fragment containing the T7-tag sequence contributed by the pET9a vector. This deletion directly links the T7 promoter to the 5' end of the chimeric 2086 gene. The NdeI deleted plasmid was transformed into *E. coli* strain BL21(DE3) and kanamycin resistant colonies were screened for chimeric 2086 protein expression with IPTG induction.

Initial studies indicate that the chimeric 2086 gene from strain 2996 expresses about twice as much recombinant protein as compared to the native 2996/2086 gene when expressed in the pET9a system. The pBAD system has not been tested yet.

Although only one experiment has been performed, the data indicate that there is an enhanced utility from the chimeric 2086 gene. The generation of CDC-1573 N-terminal fusions to the 2086 genes from strains 8529 and 2996 provides enhanced recombinant 2086 protein expression.

Example 5

2086 PCR Screening of *N. meningitidis* Strains

In order to determine the conservation of the 2086 gene among clinical isolates, PCR amplification was performed on 88 *N. meningitidis* strains.

Initial PCR identification of ORF 2086 utilized primers listed in Table IV (see Example 2 above) identified by compound numbers: 4623, 4624 and 4625. These primers were designed based on Sanger's *N. meningitidis* serogroup A sequence. To facilitate screening a large number of strains, internal primers were designed for the 2086 gene. A total of 88 *N. meningitidis* strains were screened by PCR with the newly designed internal 2086 primers identified by compound numbers 5005 and 5007. With these primers the applicants were able to identify the 2086 gene from 63 of the 88 (~70%) N. meningitidis strains, (see Table VIA).

Expanded regions surrounding the 2086 gene in Sanger's N. meningitidis serogroup A sequence and TIGR's N. meningitidis serogroup B sequence were examined and aligned. Primers were designed to correspond to regions upstream and downstream of the 2086 gene. The purpose was to utilize these primers to amplify greater than full length 2086 genes from a variety of N. meningitidis strains for sequence comparison. PCR amplification of one strain (6557), using Compound Nos. 6470 and 6472 resulted in a low yield of product. The strain 6557 amplified product was cloned and plasmid DNA was submitted for sequence analysis. Results indicated a new type of 2086 gene with greater sequence variability than had previously been seen. The 2086 gene from strain 6557 was ~75% identical at the amino acid level to the other strains sequenced. Interestingly, strain 6557 was one of the 30% of strains that had previously tested negative by 2086 PCR screening described above.

Internal primers specific to the C-terminal variable regions within strain 6557 were designed. These primers were used to screen for the more variable 2086 gene in the ~30% of strains that had previously tested negative by 2086 PCR screening. All available *N. meningitidis* strains (n=88) were screened by PCR with these newly identified internal 2086 primers (identified by compound numbers 6495 and 6496. Only the ~30% of *N. meningitidis* strains that had previously tested negative by PCR for 2086 were PCR positive in this screen. The set of genes amplified from the previously PCR negative (~30%) strains should represent a new type of 2086 gene or a second family of 2086 genes and herein are designated 2086 Subfamily A. The set of 2086 genes amplified from the ~70% of strains with the 8529 derived primers are herein designated Subfamily B.

*N. meningitidis* strains used for PCR amplification studies were selected from the following tables, Table VIA and Table VIB. The strains listed in the tables are provided as examples of *N. meningitidis* strains in addition to those previously disclosed herein, without limitation. The strains listed in Table VIA are classified in 2086 protein Subfamily A and the strains listed in Table VIB are classified in 2086 protein Subfamily B. The strains listed in each table are grouped by serosubtype. The strains are available from the following four sources as indicated in the table: MPHL-Manchester Public Health Laboratory, Manchester, UK; RIVM, Bilthoven, The Netherlands; University of Iowa, College of Medicine, Department of Microbiology, Iowa City, Iowa; and Walter Reed Army Institute of Research, Washington, D.C.

TABLE VIA

| Strain | Serosubtype | Source |
|---|---|---|
| M97 251854 | B:4z, PI:4 | MPHL |
| M98 250622 | B:2b, PI:10 | MPHL |
| M98 250572 | B:2b, PI:10 | MPHL |
| M98 250771 | B:4z, PI:14 | MPHL |
| M98 250732 | B:4z, PI:14 | MPHL |
| M98 250809 | B:15, PI:7,16 | MPHL |
| M97 252697 | B:1, PI:6 | MPHL |
| M97 252988 | B:4, PI:6 | MPHL |
| M97 252976 | B:4, PI:6 | MPHL |
| M97 252153 | B:4, PI:6 | MPHL |
| M97 253248 | B:15, PI:7, NT | MPHL |
| CDC1610 | P1:NT 4(15) | CDC |
| CDC1521 | P1.6,3 2b(4) | CDC |
| CDC1034 | P1.7 4(15) | CDC |
| L8 | P1.7,1 15(4) | Walter Reed |
| CDC1492 | P1.7,1 4(15) | CDC |
| 870446 | P1.12a,13 | RIVM |
| CDC2369 | P1.(9),14 | CDC |
| 6557 | P1.(9),14 | RIVM |
| 2996 | P1.5,2 | RIVM |
| NmB | P1.5,2 | UIOWA |
| L3 | P1.5,2 | Walter Reed |
| B16B6 | P1.5,2 | RIVM |
| CDC1135 | | CDC |
| L5 | P1.NT | Walter Reed |
| L4 | PI.21,16 | Walter Reed |

TABLE VIB

| Strain | Serosubtype | Source |
|---|---|---|
| M98 250670 | B:1, PI:4 | MPHL |
| M98 250024 | B:1, PI:4 | MPHL |
| M97 253524 | B:1, PI:4 | MPHL |
| M97 252060 | B:1, PI:4 | MPHL |
| M97 251870 | B:4z, PI:4 | MPHL |
| M97 251836 | B:4z, PI:4 | MPHL |
| M97 251830 | B:4z, PI:4 | MPHL |
| M97 251905 | B:4z, PI:4 | MPHL |
| M97 251898 | B:4z, PI:4 | MPHL |
| M97 251885 | B:4z, PI:4 | MPHL |
| M97 251876 | B:4z, PI:4 | MPHL |
| M97 251994 | B:4z, PI:4 | MPHL |
| M97 251985 | B:4z, PI:4 | MPHL |
| M97 251957 | B:4z, PI:4 | MPHL |
| M97 251926 | B:4z, PI:4 | MPHL |
| M97 252045 | B:4z, PI:4 | MPHL |
| M97 252038 | B:4z, PI:4 | MPHL |
| M97 252026 | B:4z, PI:4 | MPHL |
| M97 252010 | B:4z, PI:4 | MPHL |
| M97 252098 | B:4z, PI:4 | MPHL |
| M97 252083 | B:4z, PI:4 | MPHL |
| M97 252078 | B:4z, PI:4 | MPHL |
| M98 250735 | B:4z, PI:15 | MPHL |
| M98 250797 | B:4z, PI:15 | MPHL |
| M98 250768 | B:4z, PI:15 | MPHL |
| M98 250716 | B:2b, PI:10 | MPHL |
| M98 250699 | B:4z, PI:10 | MPHL |
| M98 250393 | B:4z, PI:10 | MPHL |
| M98 250173 | B:4z, PI:10 | MPHL |
| M97 253462 | B:4z, PI:14 | MPHL |
| M98 250762 | B:15, PI:7,16 | MPHL |
| M98 250610 | B:15, PI:7,16 | MPHL |
| M98 250626 | B:15, PI:7,16 | MPHL |
| M97 250571 | B:15, PI:16 | MPHL |
| M97 252097 | B:15, PI:16 | MPHL |
| M97 253092 | B:1, PI:6 | MPHL |
| M97 252029 | B:15, PI:7, NT | MPHL |
| M97 251875 | B:15, PI:7, NT | MPHL |
| CDC1127 | PI.7,16 4(15) | CDC |
| CDC982 | PI.7,16 4(15) | CDC |
| CDC1359 | PI.7,16 4(15) | CDC |
| CDC798 | PI.7,16 15(4) | CDC |
| CDC1078 | PI.7,16 15(4) | CDC |
| CDC1614 | PI.7,16 15(4) | CDC |
| CDC1658 | PI.7,16 15(4) | CDC |
| H44/76 | PI.7,16 15(4) | RIVM |
| CDC1985 | P1.7,13 4(15) | CDC |
| L6 | P1.7,1 ?(4) | Walter Reed |
| CDC1573 | P1.7,1 4(15) | CDC |
| L7 | P1.7,(9),1 | Walter Reed |
| CDC937 | P1.7,3 | CDC |
| 8529 | P1.7,3 | RIVM |
| 880049 | P1.7b,4 | RIVM |
| CDC2367 | P1.15 4(15) | CDC |
| H355 | P1.19,15 | RIVM |
| CDC1343 | P1.14 4(15) | CDC |
| M982 | P1.22,9 | RIVM |
| 870227 | P1.5c,10 | RIVM |
| B40 | P1.5c,10 | RIVM |
| 5315 | P1.5c,10 | RIVM |
| CDC983 | P1.5,2 | CDC |
| CDC852 | P1.5,2 | CDC |
| 6940 | P1.18,25 (6) | RIVM |

Other strains are readily available as isolates from infected individuals.

Example 6

Reactivity of RLP2086 Antisera Against Meningococcal Strains

The following table, Table VII, shows the cross-reactive and cross protection capacity of the rLP2086 as described above. As indicated in the table, the rLP2086 was processed and analyzed using a variety of techniques including whole cell ELISA (WCE) titers, bactericidal assay (BCA) and Infant Rat (IR) assays to determine the bacterial cell surface reactivity of a polyclonal antibody raised against the 2086 protein.

TABLE VII

REACTIVITY OF RLP2086-8529 ANTISERA AGAINST MULTIPLE *MENINGOCOCCAL* STRAINS

| Strain | Serosubtype | WCE | BC | IR |
|---|---|---|---|---|
| 2086 Subfamily A | | | | |
| 870446 | P1.12a,13 | 808,615 | >800 | |
| NmB | P1.5a,2c | 47,954 | <100 | |
| 6557 | P1.22a,14a | 169,479 | <25 | − |
| 2086 Subfamily B | | | | |
| 880049 | P1.7b,4 | 1,402,767 | 100 | + |
| H44/76 | P1.7,16 | 8,009,507 | >6400 | |
| H355 | P1.19,15 | 10,258,475 | 3,200 | + |
| 6940 | P1.18,25(6) | 5,625,410 | 800 | |
| 870227 | P1.5c,10 | 4,213,324 | <25 | + |
| 252097 | P1.7b,16 | 10,354,512 | >800 | |
| 539/8529 | P1.7b,3 | 11,635,737 | 3,200 | |
| M982 | P1.22,9 | 1,896,800 | 800 | |
| CDC-1573 | P1.7a,1 | 208,259 | 25 | |
| CDC-937 | P1.7b,(3) | 9,151,863 | >800 | |

+ greater than 10 fold reduction in bacteremia
− less than 10 fold reduction in bacteremia Example 7

Various constructs for expressing ORF2086 protein were prepared. The following table, Table VIII, is an r2086 construct table which is provided for the purpose of showing examples and illustrating an implementation of the present invention, without limitation thereto.

Example 8

Further studies with LOS depleted outer membrane proteins identified additional strains producing outer membrane protein(s) other than PorA which were capable of eliciting bactericidal antibodies to strains expressing heterologous serosubtypes. The following describes further studies to identify additional proteins according to one embodiment of the present invention, and specifically outer membrane lipoproteins, which can reduce the number of proteins required in a meningococcal immunogenic composition. These further studies supplement the studies described in the previous examples.

Figure 12A:
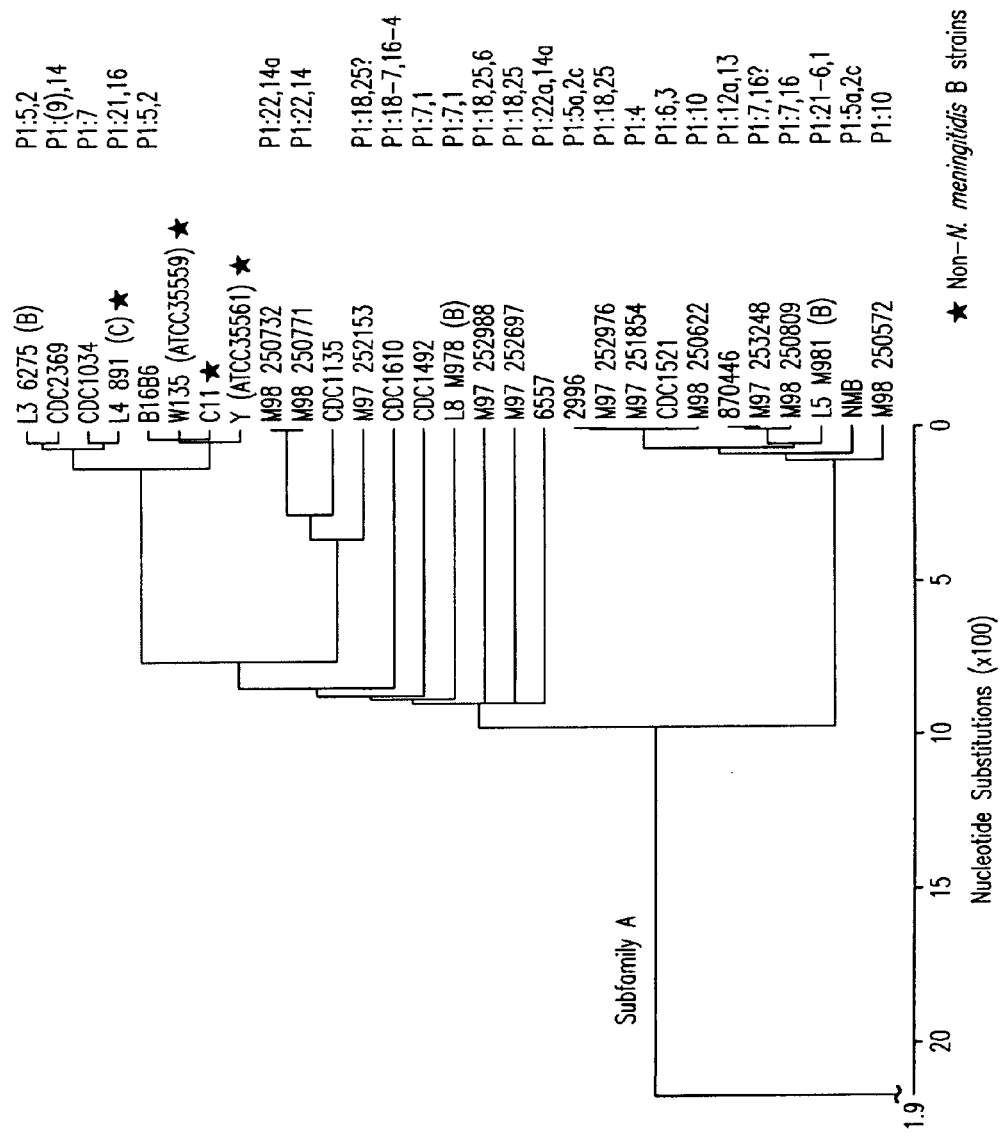
FIG. 12 is a phylogenetic tree showing an organization of the subfamilies and groups of ORF2086 proteins according an implementation of the present invention.
Figure 12B:
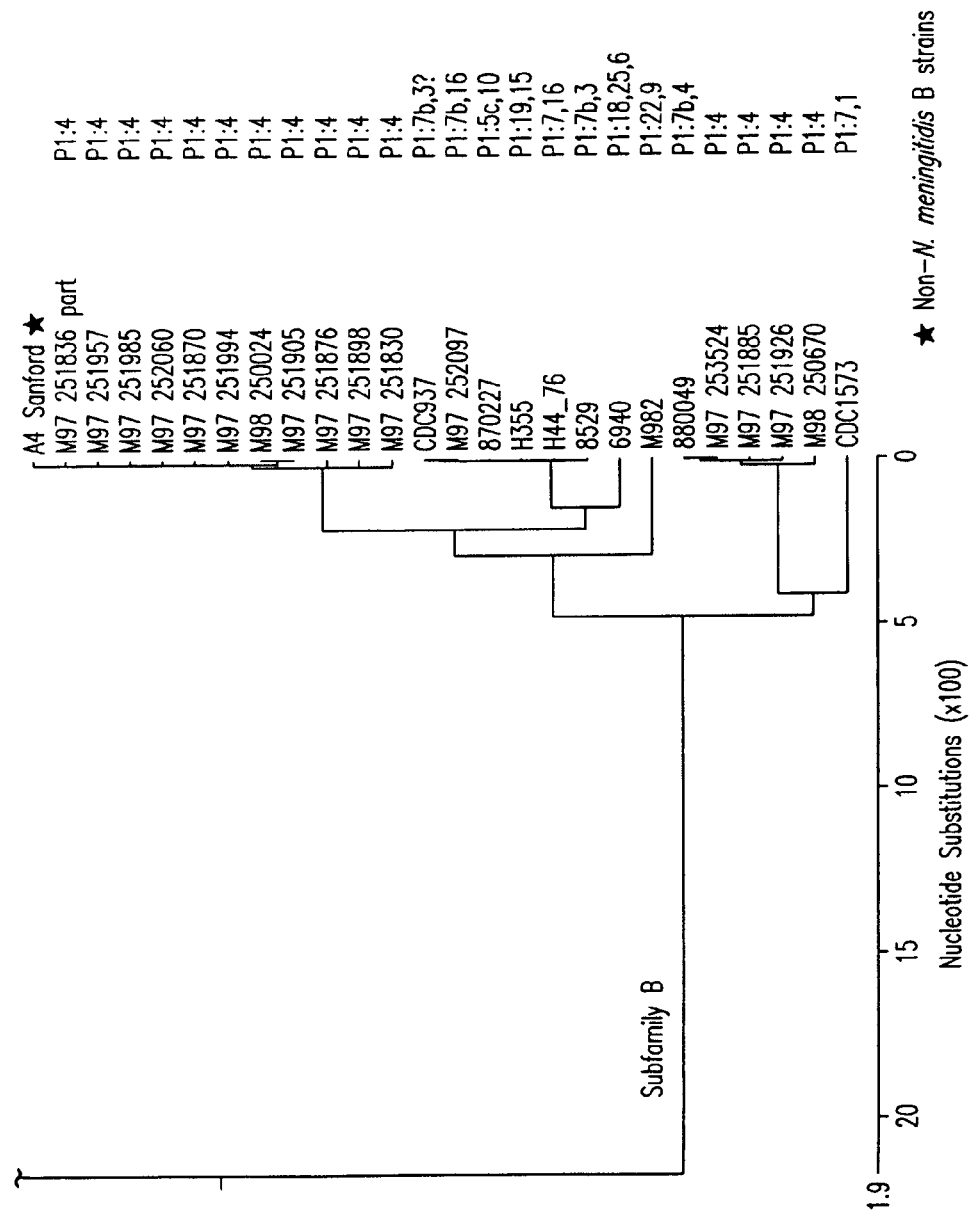
Figure 13:
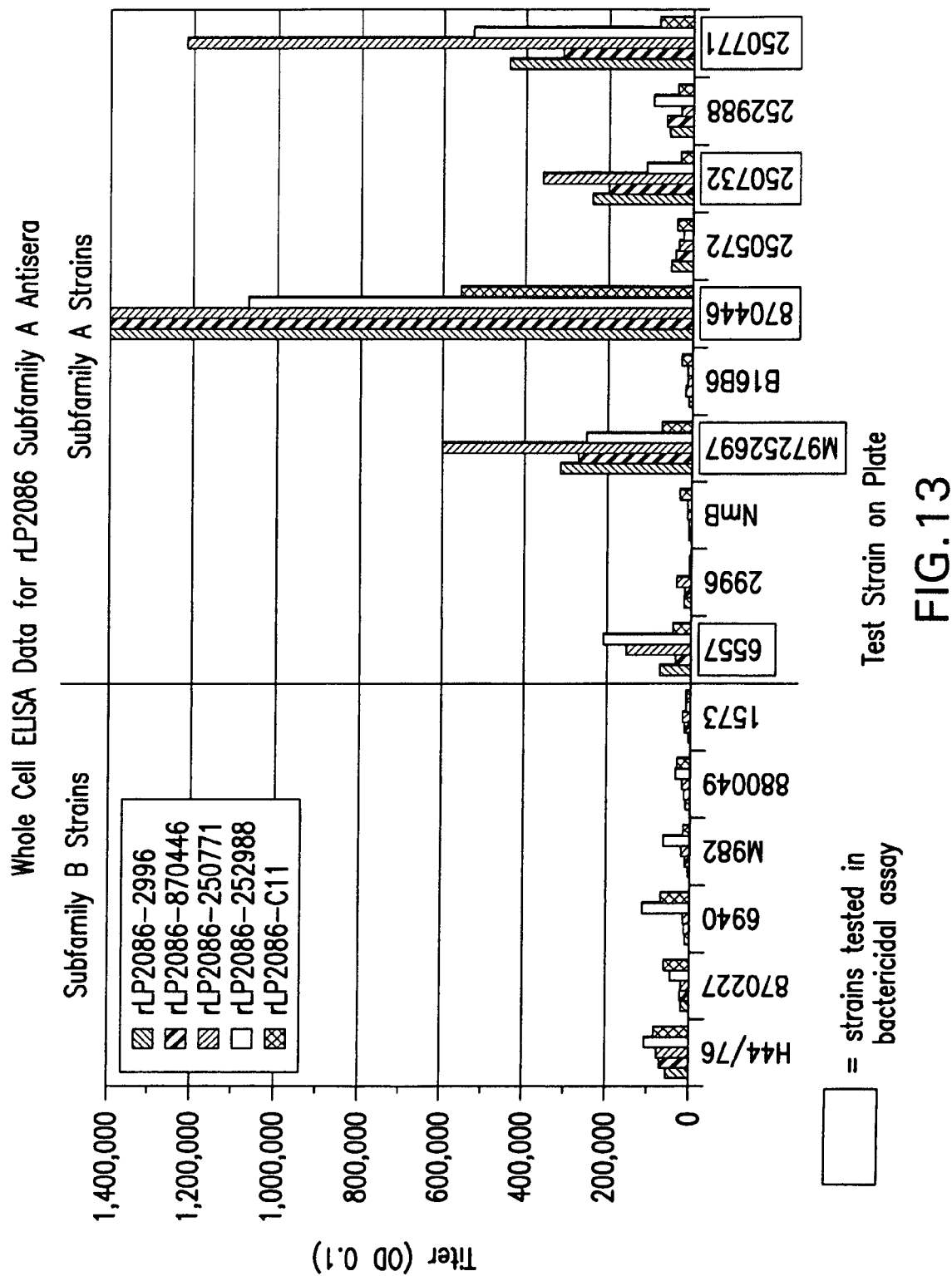
FIG. 13 is a graphic illustration of whole cell ELISA data for the rLP2086 Subfamily A antisera.
Figure 14:
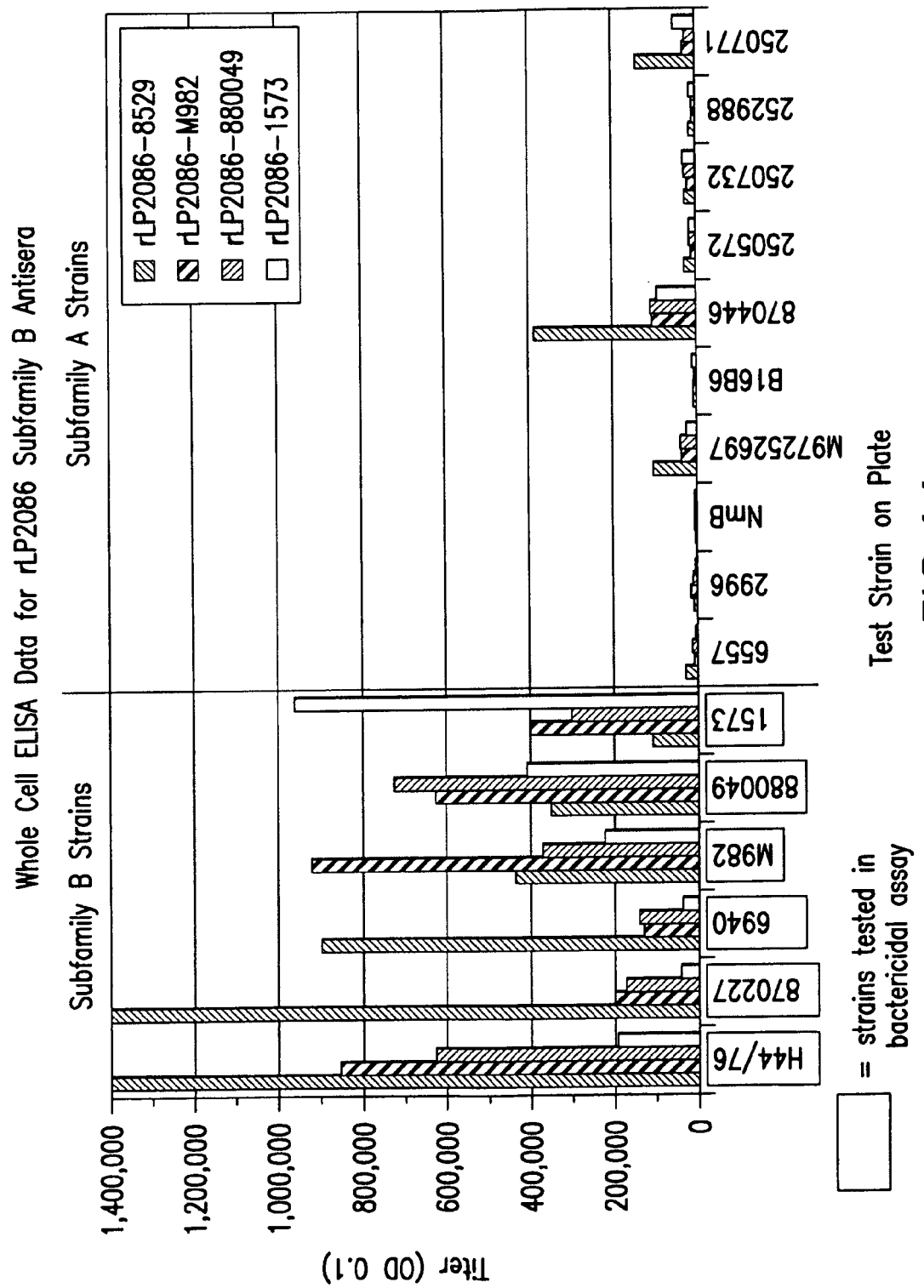
FIG. 14 is a graphical illustration of whole cell ELISA data for the rLP2086 Subfamily B antisera.
Figure 15:
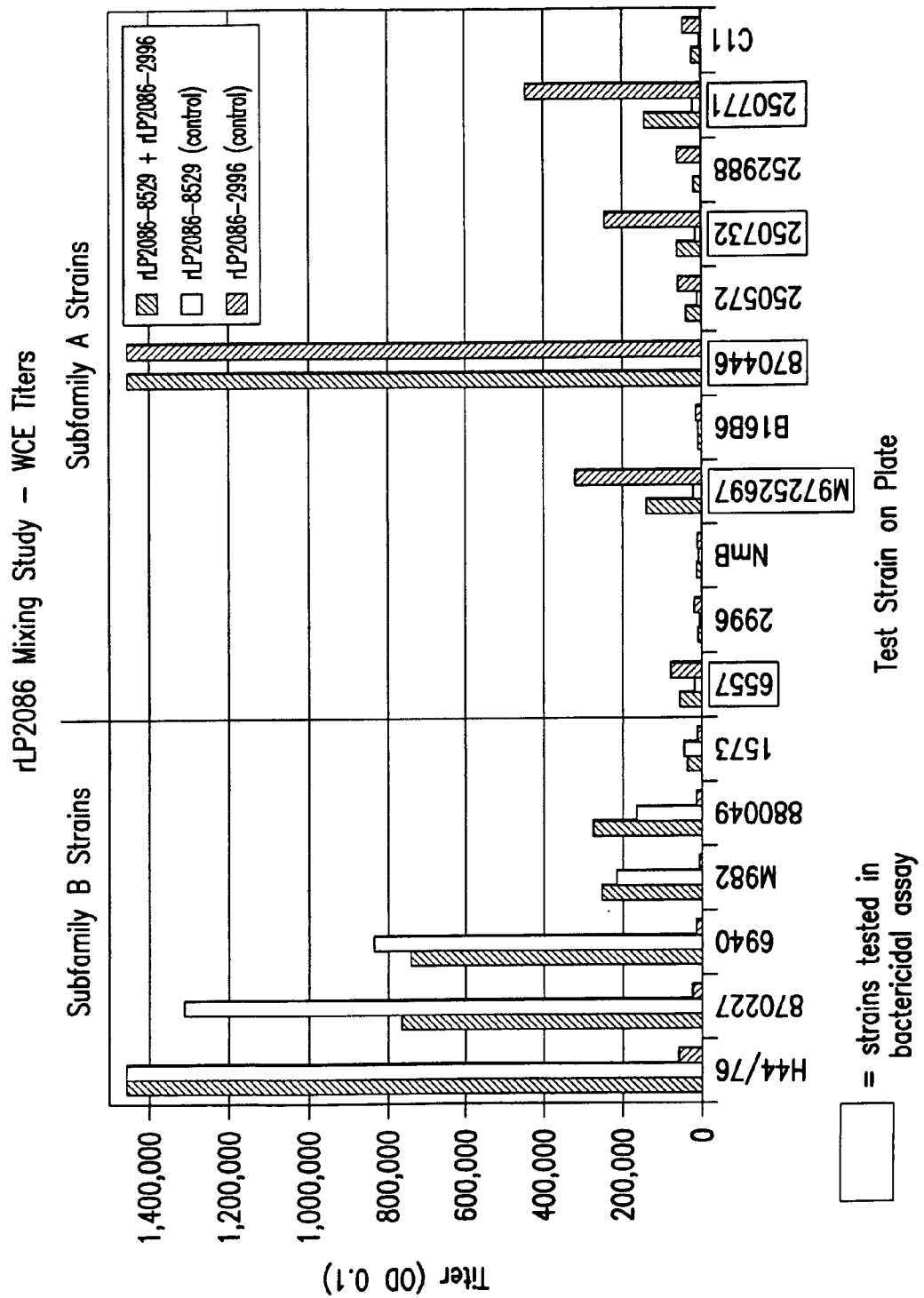
FIG. 15 is a graphical illustration of the results of the rLP2086 mixing study—WCE Titers.
Figure 16:
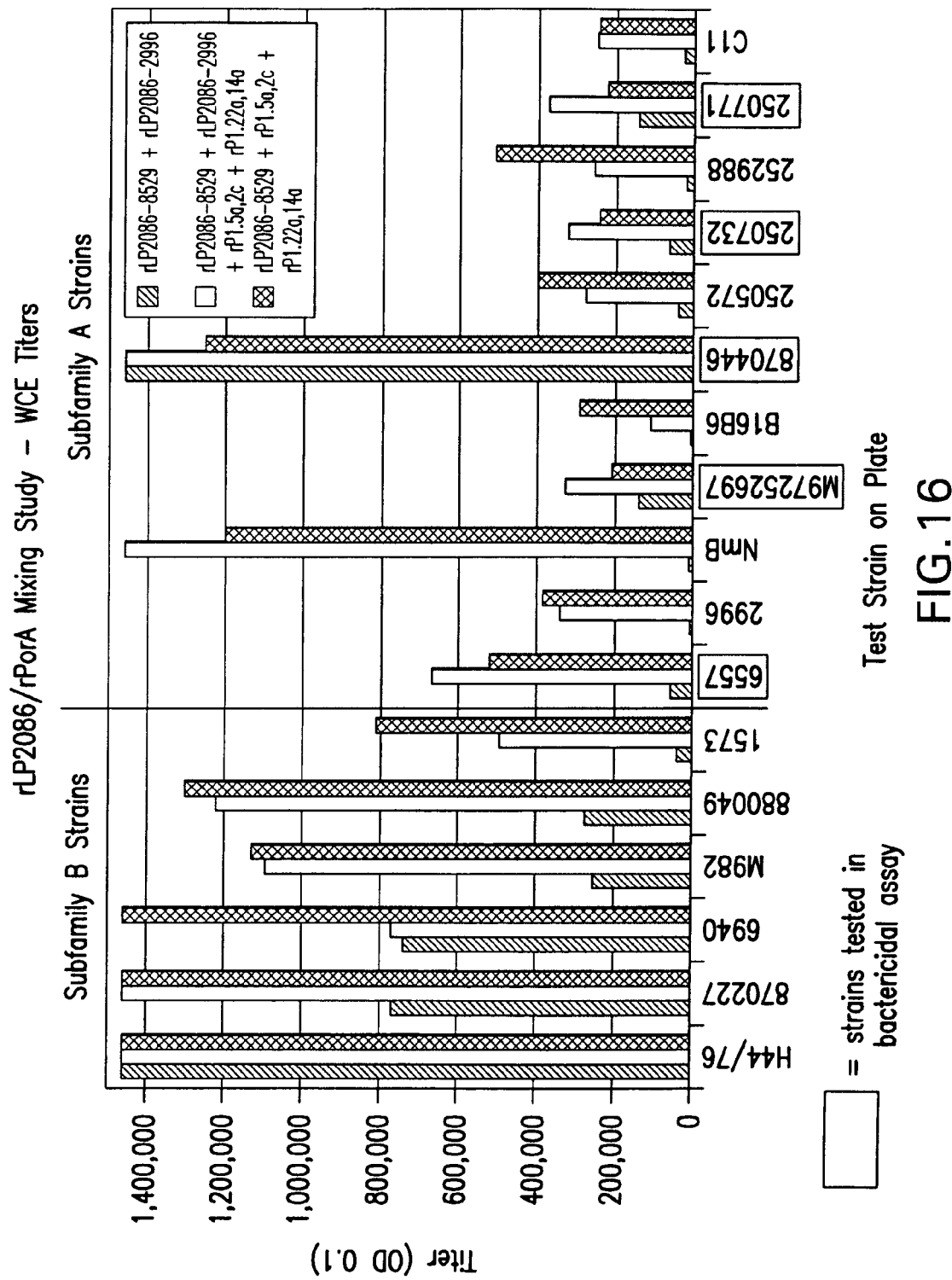
FIG. 16 is a graphical illustration of the results of the rLP2086/rPorA mixing study—WCE Titers.

Subcellular fractionation, differential detergent extraction, isoelectric focusing, and ion exchange chromatography were used in conjunction with immunization and bactericidal assays against multiple strains to identify small groups of proteins of interest. Direct sequencing of the main components indicated that the N-termini were blocked. Internal protein sequences were obtained by direct sequencing of polypeptides derived from chemical and proteolytic digests. The genomic sequence of a group A meningococcal strain was downloaded from the Sanger Center and analyzed by our Bioinformatics group using existing and proprietary algorithms to create a searchable database. The peptide sequence data indicated that ORF2086 was of interest. Primers based on this orf were used to PCR the P2086 gene from strain 8529. Analysis of the gene sequence, the fact that the N-terminus was blocked, and its subcellular location indicated that P2086 is a lipidated outer membrane protein(LP2086). rLP2086-8529 and variants from other meningococcal strains were recombinantly expressed as lipoproteins in *E. coli* using the *H. influenzae* P4 signal sequence. These recombinant proteins were isolated from *E. coli* membranes by differential detergent extraction, purified using ion exchange chromatography, and used to immunize mice. Mouse anti-LP2086 sera were able to facilitate bactericidal activity against several different serosubtype strains of *N. meningitidis*. Further analysis of the P2086 genes from many *N. meningitidis* strains showed that these sequences fell into two groups designated Subfamily A and Subfamily B. (See FIG. 12) The antisera raised against the Subfamily B proteins were bactericidal against nine strains expressing Subfamily B proteins, and one strain expressing a Subfamily A protein. Subfamily A antisera were bactericidal against Subfamily A strains. A mixture of one rPorA and one rLP2086 elicited complemen-

TABLE VIII

R2086 CONSTRUCT SUMMARY

| Construct | Promoter | Leader | Expression | Extraction | Vector | % total Protein |
|---|---|---|---|---|---|---|
| pPX7340 | T7 | native | COOMASSIE | sarcosyl soluble | pET27b | 2.5% processed lipoprotein |
| pPX7341 | T7 | P4 | COOMASSIE | sarcosyl soluble | pET27b | 5% processed lipoprotein |
| pPX7343 | Arabinose | P4 | COOMASSIE | sarcosyl soluble | pBAD18 cm | 7-10% processed lipoprotein |
| pPX7325 | T7 | T7-tag fusion/mature | COOMASSIE | inclusion bodies | pET9a | 40-50% mature protein |
| pPX7328 | T7 | mature | COOMASSIE | Soluble | pET9a | 10% mature protein | tary antibodies extending vaccine coverage beyond that induced by either protein alone.

These observations lead to the following conclusions. rLP2086 antigens are capable of eliciting bactericidal antibodies against meningococcal strains expressing heterologous PorAs and heterologous P2086 proteins. The P2086 family of antigens may be a useful vaccine or immunogenic either alone or in combination with other neisserial antigens.

The following describes the foregoing study in detail. A complex mixture of soluble outer membrane proteins (sOMPs) was found to elicit PorA independent bactericidal antibody against strains expressing heterologous PorA proteins. A process of differential detergent extraction, isoelectric focusing and ion exchange chromatography followed by mouse immunization was used to follow the immunologically active components.

At each step, sera was assayed for surface reactivity and bactericidal activity against several strains containing serosubtype antigens that are representative of the worldwide epidemiology of meningococcal disease.

This process of separation and immunization was used to identify a novel cross-reactive immunogenic candidate for Group B N. meningitidis.

Generation of PorA deficient strains—The porA chromosomal locus was cloned into plasmid pPX7016 from strain 2996. Within the plasmid the porA promoter, the S/D box and the first 38 N-terminal codons have been deleted and replaced with a self contained KanR expressing cassette. The plasmids were linearized with restriction enzymes and naturally transformed into the serosubtype strains PI:5,2; PI:9; PI:7,16; PI:15; PI:4; P1:3 & PI:10. Kanamycin resistant transformants were selected and screened for the loss of PorA by serosubtype specific monoclonals in an ELISA.

Bactericidal Assay: See Mountzourous, K. T. and Howell, A. P. Detection of Complement-Mediated Antibody-Dependent Bactericidal Activity in a Flourescence-Based Serum Bactericidal Assay for Group B *Neisseria meningitidis*. J Clin Microbiol. 2000; 38:2878-2884.

Whole Cell Enzyme Linked immunosorbant Assay (ELISA): *N. meningitidis* whole cell suspensions were diluted to an optical density of 0.1 at 620 nm in sterile 0.01 M phosphate, 0.137M NaCl, 0.002M KCl (PBS). From this suspension, 0.1 mL were added to each well of Nunc Bac T 96 well plates (Cat#2-69620). Cells were dried on the plates at 37° C. overnight, then were covered, inverted and stored at 4° C. Plates were washed three times with wash buffer (0.01M Tris-HCl, 0.139M NaCl/KCl, 0.1% BRIJ-35, pH 7.0-7.4). Dilutions of antisera were prepared in PBS, 0.05% TWEEN-20/Azide and 0.1 mL was transferred to the coated plates and incubated for two hours at 37° C. Plates were washed three times in wash buffer. Goat-anti-mouse IgG AP (Southern Biotech) was diluted at 1:1500 in PBS/0.05% TWEEN-20, 0.1 mL was added to each well, and plates were incubated at 37° C. for two hours. Plates were washed (as above). Substrate solution was prepared by diluting p-nitrophenyl phosphate (Sigma) in diethanolamine at 1 mg/ml. Substrate was added to the plate at 0.1 mL per well and incubated at room temperature for one hour. The reaction was stopped with 50 ul/well of 3N NaOH and plates were read at 405 nm with 690 nm reference.

Recombinant PorA Induction: The BLR(DE3)/pET9a strains were grown overnight at 37° C. in HySoy Broth (Sheffield Products) supplemented with Kan-30 and 2% glucose. In the morning the O/N cultures were diluted 1/20 in HySoy Broth Kan-30 and 1% glycerol and grown at 37° C. for 1 hour. These cultures were induced by the addition of IPTG to a final concentration of 1 mM. The cultures were grown for an additional 2-3 hours and then harvested.

Recombinant PorA Purification: The rPorA was solubilized from *E. coli* inclusion bodies with 8M Urea, and refolded by dialysis against buffer containing no urea. The refolded rPorA was then concentrated by diafiltration and buffer exchanged by G25 column into NaPO4 pH6. The dialyzed rPorA was then run on a cation exchange column (FRACTOGEL) and eluted with 1M NaCl.

The sOMPs from strain 8529 (P1.7-2,3) elicit PorA independent bactericidal activity in mice against strains expressing heterologous serosubtypes. The following table, Table IX, shows the bactericidal activity in the studied strains.

TABLE IX

| Test Strain | Serosubtype | $BC_{50}$ Titer[1] |
|---|---|---|
| 539 | P1.7-2,3 | 1280 |
| 539 PorA- | NST[2] | 1080 |
| H44/76 | P1.7,16 | 3285 |
| H44/76 PorA- | NST | 2620 |
| H355 | P1.19,15 | >1350 |
| H355 PorA- | NST | >1350 |
| 880049 | P1.7-2,4 | 290 |
| 880049 PorA- | NST | 85 |
| M982 | P1.22,9 | 85 |
| M982 PorA- | NST | <50 |

Preparation of sOMPs: *N. meningitidis* membranes were extracted with TX-100, ZWITTERGENT 3-14, and ZWITTERGENT 3-14 + 0.5M NaCl. The sOMPs referred to above were solubilized in the ZWITTERGENT 3-14/0.5M NaCl extract. The extraction is performed using techniques well known to persons skilled in the art, for example, see U.S. Pat. No. 6,355,253 which is hereby incorporated by reference.
Immunogenicity: Female Swiss-Webster mice were immunized with 25 ug total protein adjuvanted with 20 ug QS-21 at weeks 0 and 4. An exsanguination bleed and data analysis were done at week 6.
[1]Bactericidal ($BC_{50}$) titers represented as the reciprocal of the dilution of anti-sera which reduces viable cell count by 50%. Week 0 normal mouse sera had $BC_{50}$ titers of <25
[2]NST = Non Serosubtypable The following tables, Table X and Table XI, show the purification and characterization summary for recombinant lipidated P2086 (rLP2086) for both Subfamily A and Subfamily B.

Subfamily A rLP2086 Purification

TABLE X

| rLP2086 Variant | A.A. Homology (%)[1] | Theoretical pI | Purity (%)[2] |
|---|---|---|---|
| 870446 | 75 | 6.1 | 80 |
| 2996 | 71 | 5.9 | 95 |
| M97 252988 | 71 | 6.3 | 96 |
| C11 | 68 | 6.4 | 82 |
| M98 250771 | 62 | 6.1 | 83 |

Subfamily B rLP2086 Purification

TABLE XI

| rLP2086 Variant | A.A. Homology (%)[1] | Theoretical pI | Purity (%)[2] |
|---|---|---|---|
| 8529 | 100 | 7.5 | 96 |
| M982 | 94 | 6.3 | 96 |
| 88049 | 92 | 6.2 | 90 |
| CDC1573 | 87 | 5.6 | 93 |

Purification Method: All variants were solubilized from *E. coli* membranes with TX-100 (exception rLP2086-8529 which was solubilized with SARCOSYL or Urea). Further purification was achieved with a combination of anion exchange (TMAE), size exclusion and/or cation exchange (S FRACTOGEL) chromatography in a Tris-HCl or NaPO4 buffer.
[1]Amino acid homology as compared to P2086 from strain 8529
[2]Purity as determined by SDS-PAGE and laser densitometry of colloidal COOMASSIE stained band (Simply Blue stain)
Immunogenicity of a Subfamily B member, rLP2086-8529, tested against homologous and heterologous strains Table XII below shows immunogenicity of a Subfamily B member, rLP2086-8529, tested against homologous and heterologous strains

TABLE XII

| Target Strain | P2086 Subfamily | Target Strain Serosubtype | A.A. Homology[a] | Whole Cell ELISA[b] Titer | BC$_{50}$ Titer[c] |
|---|---|---|---|---|---|
| 539 | B | P1.7-2,3 | 100 | >1,458,000 | 3,200 |
| H44/76 | B | P1.7,16 | 100 | >1,458,000 | 3,200 |
| H355 | B | P1.19,15 | 100 | >1,458,000 | 3,200 |
| CDC937 | B | P1.7-2,3-4 | 100 | >1,458,000 | >800 |
| M97 252097 | B | P1.7-2,16 | 100 | >1,458,000 | >800 |
| 870227 | B | P1.5-2,10 | 100 | >1,458,000 | <25 |
| 6940 | B | P1.18,25,6 | 97 | 900,162 | >800 |
| M982 | B | P1.22,9 | 94 | 435,909 | 200 |
| 880049 | B | P1.7-2,4 | 92 | 349,912 | 400 |
| CDC1573 | B | P1.7-1,1 | 87 | 102,508 | 25 |
| 870446 | A | P1.12-1,13 | 71 | 389,829 | 800 |
| M98 250771 | A | P1.22,14 | 62 | 139,397 | <25 |
| NmB | A | P1.5-1,2-2 | 71 | <2,000 | <25 |

Vaccination Procedure: 6-8 week old female Swiss-Webster mice were immunized with 10 ug rLP2086-8529 + 20 ug QS-21 at week 0 and week 4. Data analysis was performed on the week 6 exsanguination bleed.
[a]Amino acid homology of P2086 as compared with rLP2086-8529
[b]Endpoint titers expressed as the reciprocal of the dilution at absorbance = 0.1
[c]BC50 titers represented as the reciprocal of the dilution of anti-sera which reduces viable cell count by 50%. Week 0 normal mouse sera had BC50 titers of <10.

Table XIII shows immunogenicity of a Subfamily B member, rLP2086-2996, tested against homologous and heterologous strains.

TABLE XIII

| Target Strain | P2086 Subfamily | Target Strain Serosubtype | A.A. Homology[a] | Whole Cell ELISA[b] Titer | BC$_{50}$ Titer[c] |
|---|---|---|---|---|---|
| NmB | A | P1.5-1,2-2 | 99.6 | 8,979 | <25 |
| 870446 | A | P1.12-1,13 | 99 | <1,458,000 | >800 |
| M97 252697 | A | P1.18,25,6 | 98 | 320,732 | >800 |
| 6557 | A | P1.22-1,14-1 | 98 | 17,319 | <25 |
| M98 250732 | A | P1.22,14-1 | 89 | 241,510 | >800 |
| M98 250771 | A | P1.22,14 | 89 | 447,867 | 800 |
| H44/76 | B | P1.7,16 | 72 | 56,386 | <25 |

Vaccination Procedure: 6-8 week old female Swiss-Webster mice were immunized with 10 ug rLP2086-2996 + 20 ug QS-21 at week 0 and week 4. Data analysis was performed on the week 6 exsanguination bleed.
[a]Amino acid homology of P2086 as compared with rLP2086-2996
[b]Endpoint titers expressed as the reciprocal of the dilution at absorbance = 0.1
[c]Bactericidal (BC50) titers represented as the reciprocal of the dilution of anti-sera which reduces viable cell count by 50%. Week 0 normal mouse sera had BC50 titers of <10.

Table XIV below shows that antisera to rLP2086 and rPorA are complimentary when mixed and assayed for bactericidal activity.

TABLE XIV

| Antisera | H44/76 (P1.7,16) | NMB (P1.5-1,2-2) | 880049 (P1.7-2,4) | H355 (P1.19,15) | 870227 (P1.5-2,10) | 6557 (P1.22-1,14-1) |
|---|---|---|---|---|---|---|
| Anti-rLP2086 + three rPorA antisera | >3,200 | >800 | 200 | >800 | 200 | 200 |
| Controls anti-rLP2086 | 6,400 | <25 | 100 | 3,200 | <25 | <25 |
| Corresponding monovalent rPorA antisera | — | 1,600 | — | — | 200 | 400 |

Vaccination Procedure: 6-8 week old female Swiss-Webster mice were immunized with either 10 ug rLP2086-8529/20 ug QS-21, or 15 ug rPorA/100 ug MPL at week 0 and week 4. Data analysis was performed on the week 6 exsanguination bleed.
a Bactericidal (BC50) titers represented as the reciprocal of the dilution of anti-sera which reduces viable cell count by 50%. Week 0 normal mouse sera had BC50 titers of <10.

The following table, Table XV, shows that mixtures of rLP2086 Subfamilies and two rPorAs elicit bactericidal antibody in mice.

TABLE XV

| Antigen | H44/76 SfB[b] P1.7,16 | 6940 SfB P1.1825,6 | 880049 SfB P1.7-2,4 | M982 SfB P1.22,9 | M98 250771 SfA[b] P1.22,14 | M98 250732 SfA P1.22,14-1 | M97 252697 SfA P1.18,25,6 | 870446 SfA P1.12-1,13 | NmB SfA P1.5-1,2-2 | 6557 SfA P1.22-1,14-1 |
|---|---|---|---|---|---|---|---|---|---|---|
| rLP2086-8529 + rLP2086-2996 | >800 | >800 | 200 | 400 | 800 | >800 | >800 | >800 | — | <25 |
| rLP2086-8529 + rLP2086-2996 + rP1.5-1,2-2 + rP1.22-1,14-1 | >800 | 800 | 100 | 200 | 400 | 400 | >800 | >800 | >800 | 200 |
| Monovalent Controls[c] | >800 | >800 | 200 | 400 | 800 | >800 | >800 | >800 | >800 | 800 |

Vaccination Procedure: 6-8 week old female Swiss-Webster mice were immunized with 10 ug of each protein + 20 ug QS-21 at week 0 and week 4. Data analysis was performed on the week 6 exsanguination bleed.
a Bactericidal (BC50) titers represented as the reciprocal of the dilution of anti-sera which reduces viable cell count by 50%. Week 0 normal mouse sera had BC50 titers of <10.
[b]SfA—Subfamily A, SfB—Subfamily B
[c]Relevant monovalent control: rLP2086-8529, rLP2086-2996, rP1.5-1,2-2 or rP1.22-1,14-1 antisera The following summarizes the results of the above described studies. Anti-rLP2086 antisera is bactericidal against 13/16 test strains. Eleven strains expressing different serosubtypes are killed by anti-P2086 sera. Bactericidal activity of anti-rLP2086 sera is complimentary to anti-rPorA sera. Mixtures of P2086 and PorA elicit complimentary bactericidal antibodies in mice. Differential detergent extraction, purification and immunization in conjunction with a functional antibody assay against many strains can be used to identify new vaccine candidates. P2086 has been identified as a vaccine candidate that elicits bactericidal antibody against strains heterologous in both P2086 and rPorA. Thus, the 2086 family of proteins may be a useful vaccine either alone or in combination with other neisserial antigens.

Example 9

Meningococcal strains, of varying serogroups, were screened by PCR for the presence of the ORF 2086 gene. Ultimately, over one hundred meningococcal strains were screened.

Two sets of internal PCR primers specific to the C-terminal variable regions were utilized to discriminate between Subfamily A and B gene sequences. The presence of a PCR amplified product of approximately 350 bp indicated that the 2086 gene sequence was present on the chromosome. All strains yielded a single PCR product of the expected size. The nucleotide sequences of full-length ORF 2086 genes were determined, aligned (DNAStar MegAlign) and used to generate a phylogenetic tree.

2086 genes were recombinantly expressed as an rLP2086 lipoprotein in a pBAD arabinose inducible promoter system or as an rP2086 non-lipidated protein in an IPTG inducible pET system. These recombinant proteins were expressed in *E. coli* B. The purified recombinant protein was used to immunize mice and the mouse antisera was assayed for its serum IgG titers and its bactericidal activity against a variety of heterologous meningococcal strains.

ORF 2086 was amplified by PCR from one of the following: whole meningococcal cells, purified chromosomal DNA or plasmid DNA templates.

Figure 10B:
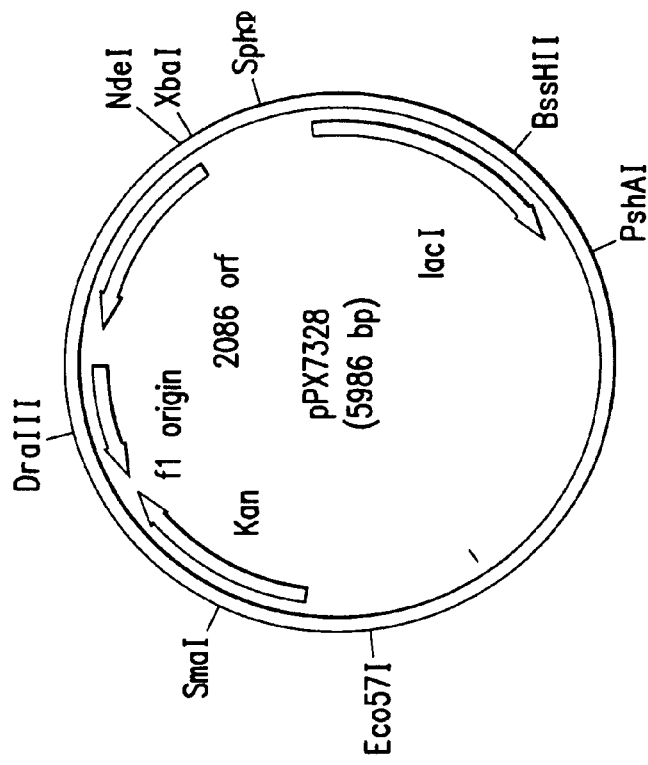
FIG. 10B is a schematic diagram of the pET9a-T7 vector for recombinant expression of nonlipidated form of ORF2086.
Figure 10A:
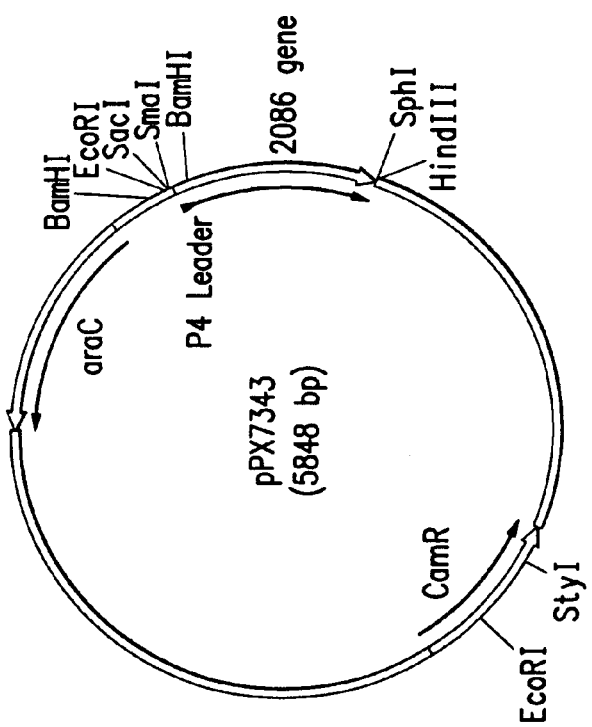
FIG. 10A is a schematic diagram of the pBAD arabinose inducible promoter which drives the expression of the P4 signal/ORF2086 fusion protein to express a lipidated form of rP2086 as described in the examples herein.
Figures 11A, 11B:
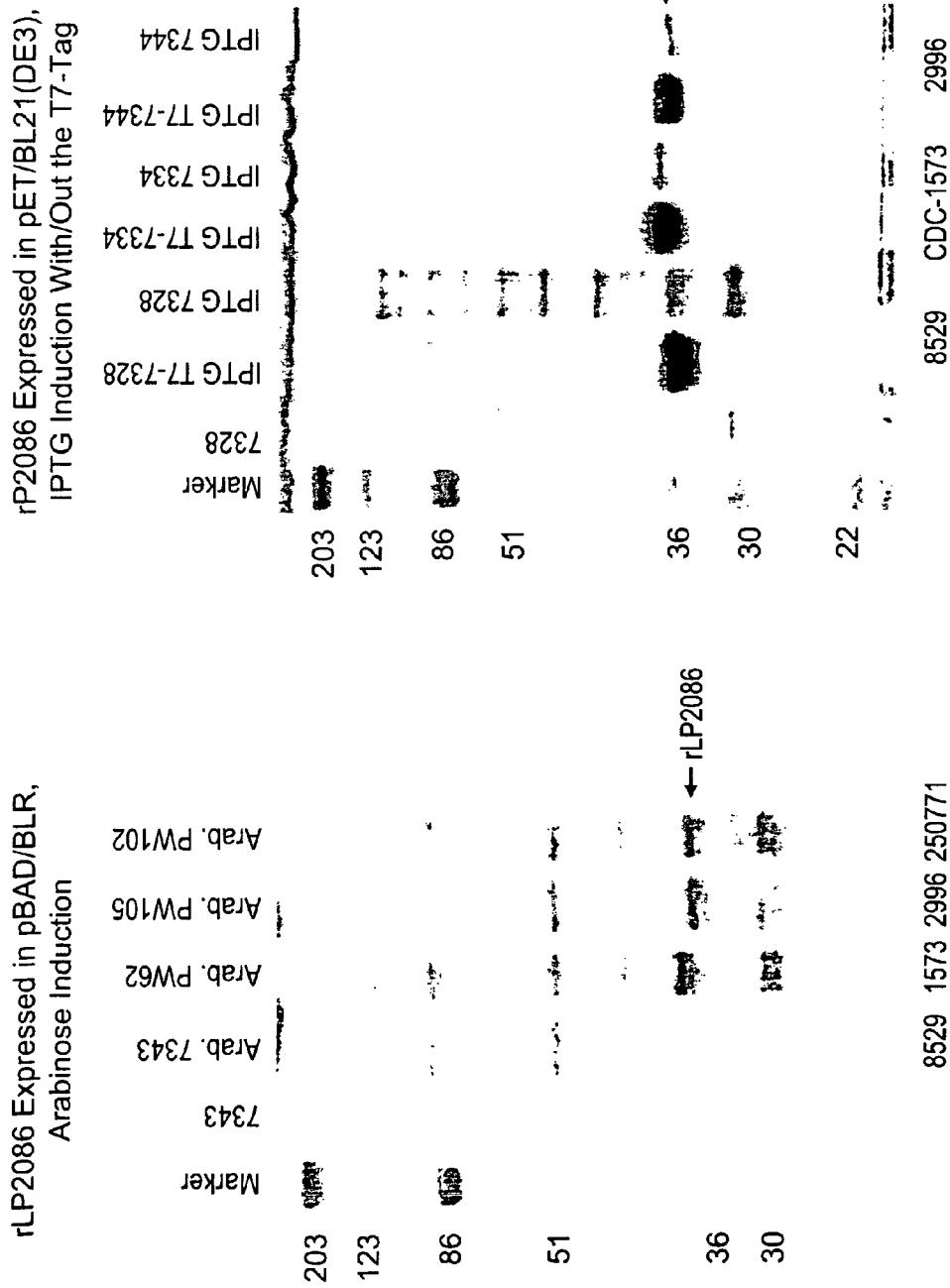
FIG. 11A is a photograph representing whole cell lysates of *E. coli* B expressing the rLP2086 protein.
FIG. 11B shows whole cell lysates of *E. coli* B expressing the rP2086 protein.

ORF 2086 genes were cloned into the vector pLP339, which fuses the *Haemophilus* P4 leader sequence to the 5' end of the ORF 2086 genes. *E. coli* strain BLR was used as the host strain for recombinant expression of the lipidated form of rP2086 from the pBAD/ORF 2086 clones. (See FIG. 10A) The pBAD arabinose inducible promoter drives the expression the P4 signal/ORF 2086 fusion protein to express a lipidated form of rP2086. P2086 genes lacking a signal sequence, were cloned into a pET9a vector behind the highly active T7 phage promoter. *E. coli* strain BL21(DE3) was used as the host strain for recombinant expression of a non-lipidated form of ORF 2086 from the pET9a/ORF 2086 clones. The DE3 lysogen in *E. coli* strain BL21 can be induced to express the T7 RNA polymerase under the control of the lacUV5 promoter by addition of IPTG. See, WCE; *FEMS Micro. Lett.*, 48 (1987) 367-371 and BCA; *J. Clin. Microbiol.*, 38 (2000) 2878-2884.

The gene, ORF2086, was cloned and sequenced from different *N. meningitidis* strains. The nucleotide sequences were aligned (DNAStar MegAlign) and used to generate a phylogenetic tree. This tree reveals two distinct subfamilies of the ORF 2086 gene nucleotide sequence. The two subfamilies of genes are similar at their 5' ends, but contain considerable variation near their 3' ends. Although there appears to be significant variability, certain key regions of the gene are highly homologous among the different strains. Without intending to be bound by theory, these conserved regions may provide functional continuity for the protein and may be indicative of cross-protective epitopes to be exploited as vaccine targets.

The 2086 gene was cloned from several serogroup B meningococcal strains and expressed with and without the lipidation signal sequence. The non-lipidated form fused to the T7-Tag expressed at the highest level. The T7-Tag sequence may provide stability to the mRNA and significantly enhances the level of polypeptide translated. This fusion protein appears to deposit in inclusion bodies and can be purified and refolded readily with known protocols. The lipidated and non-lipidated forms of P2086 are expressed at approximately 5 to 8% of total cellular protein, with the exception of the T7-Tag fusions, which express rP2086 as approximately 50% of total protein. The non-lipidated form of the protein appears to be soluble and localized in the cytoplasm. The lipidated form of the protein appears to be associated with the membrane fractions and is solubilized with detergent. The protein in its native lipidated form may have superior tertiary structure for antigen presentation and/or the attached lipid may act as an adjuvant stimulating a greater immunogenic response.

All *N. meningitidis* B strains tested appear to have one 2086-like gene. At least two families of the 2086 gene are represented. 2086 homologs have been identified by PCR screening in the following:

*N. meningitidis* A, B, C, W135, Y

*N. lactamica*

*N. gonorrhoeae* FA1090

Several ORF 2086 genes have been cloned and recombinantly expressed

Lipidated versions of P2086 were expressed from various meningococcal strains.

These recombinant proteins have been purified and used to vaccinate mice.

The resulting antisera is bactericidal.

Non-lipidated versions of P2086 were expressed from various strains.

rLP2086 consistently elicits a greater immune response than rP2086.

rLP2086 also exhibits enhanced bactericidal activity against both homologous and heterologous meningococcal strains.

Example 11

The following further demonstrates that P2086 is expressed in neisserial strains and provides additional specific examples of P2086 expression in several strains.

Cell lysates were prepared with cells from plate cultures resuspended in SDS sample buffer and heated at 98° C. for four minutes. Samples were loaded at ~30-50 ug total protein per well on 10-20% pre-cast gels (ICN) and run at 175V. The gels were transferred to a nitrocellulose membrane, which was then blocked for 30 min. with 5% powdered milk in Tris-buffered saline (BLOTTO). The primary antibody used was a pool of polyclonal antisera raised against individual rLP2086 variants in mice.

Figure 18:
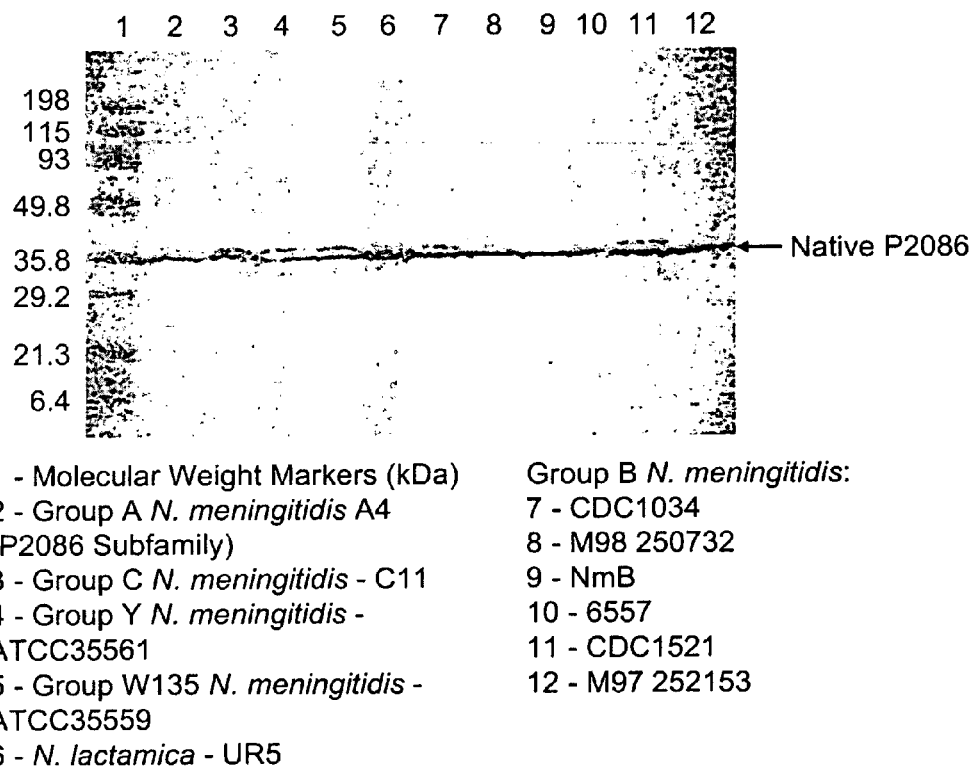
FIG. 18 is a Western Blot showing reactivity of rLP2086 mouse antisera to P2086 Subfamily A *N. meningitidis* and *N. lactamica* whole cell lysates.

Referring to FIGS. 17 and 18, a Western Blot shows the reactivity of rLP2086 mouse antisera to P2086 Subfamily A and B whole cell lysates. For the Subfamily A cell lysate blot, the antisera used were raised against rLP2086-2996, -870446 and −250771 with rLP2086-250771 diluted at 1/500 in BLOTTO and the others diluted at 1/1000 in BLOTTO. For the Subfamily B cell lysate blot, the antisera used were raised against rLP2086-8529 (diluted 1/1000 in BLOTTO), -CDC1573, -M982 and -880049 (these three diluted 1/500 in BLOTTO). The primary antisera and blot were incubated at 4° C. overnight. The blot was washed, a goat-anti-mouseAP secondary was added at 1/500 in BLOTTO, and the blot was incubated for 30 min. at room temperature. After washing, the blot was developed using the BCIP/NBT Membrane Phosphatase Substrate System (KPL).

BIBLIOGRAPHY

References referred to herein above are noted below and are incorporated herein by reference in their entirety:

1. 1997. Case definitions for Infectious Conditions Under Public Health Surveillance. CDC.
2. 1995 Sambrook, J. and D. W. Russell. 1995. Current Protocols in Molecular Biology. John Wiley & Sons, Inc., New York.
3. 1994. Griffin, A. M. and Griffin, H. G., ed., Computer Analysis of Sequence Data, Part I. Humana Press, New Jersey.
4. 1993. Smith, D. W. ed., Biocomputing: Informatics and Genome Projects. Academic Press, New York
5. 1991. Gribskov, M. and Devereux, J., ed. Sequence Analysis Primer. Stockton Press, New York.
6. 1988. Lesk, A. M., ed. Computational Molecular Biology. Oxford University Press, New York.
7. Abdillahi, H., and J. T. Poolman. 1988. *Neisseria meningitidis* group B serosubtyping using monoclonal antibodies in whole-cell ELISA. *Microbial Pathogenesis* 4(1):27-32.
8. Achtman, M. 1995. Epidemic spread and antigenic variability of *Neisseria meningitidis. Trends in Microbiology* 3(5):186-92.
9. Alm, R. A., L. S. Ling, D. T. Moir, B. L. King, E. D. Brown, P. C. Doig, D. R. Smith, B. Noonan, B. C. Guild, B. L. deJonge, G. Carmel, P. J. Tummino, A. Caruso, M. Uria-Nickelsen, D. M. Mills, C. Ives, R. Gibson, D. Merberg, S. D. Mills, Q. Jiang, D. E. Taylor, G. F. Vovis, and T. J. Trust. 1999. Genomic-sequence comparison of two unrelated isolates of the human gastric pathogen *Helicobacter pylori* [published erratum appears in Nature 1999 Feb. 25; 397 (6721):719]. *Nature.* 397:176-80.
10. Altschul, S. F., T. L. Madden, A. A. Schaffer, J. Zhang, Z. Zhang, W. Miller, and D. J. Lipman. 1997. Gapped BLAST and PSI-BLAST: a new generation of protein database search programs. Nucleic Acids Res. 25:3389-402.
11. Anderson, T. F. 1951. Techniques for the preservation of three-dimensional structure in preparing specimens for the electron microscope. Trans N Y Acad. Sci. 13:130-134.
12. Ambrosch, F., G. Wiedermann, P. Crooy, and A. M. George. 1983. Immunogenicity and side-effects of a new tetravalent meningococcal polysaccharide vaccine. *Bulletin of the World Health Organization* 61(2):317-23.
13. Benson, G. 1999. Tandem repeats finder: a program to analyze DNA sequences. Nucleic Acids Res. 27:573-80.
14. Carillo, H., D. Lipman, and J. Siam. 1988. *Applied Math* 48:1073.
15. Chen, C. C., and P. P. Cleary. 1989. Cloning and expression of the streptococcal C5a peptidase gene in *Escherichia coli*: linkage to the type 12 M protein gene. *Infect. Immun.* 57:1740-1745.
16. Chmouryguina, I., A. Suvorov, P. Ferrieri, and P. P. Cleary. 1996. Conservation of the C5a peptidase genes in group A and B streptococci. *Infect. Immun.* 64:2387-2390.
17. Cockerill, F. R., 3rd, R. L. Thompson, J. M. Musser, P. M. Schlievert, J. Talbot, K. E. Holley, W. S. Harmsen, D. M. Ilstrup, P. C. Kohner, M. H. Kim, B. Frankfort, J. M. Manahan, J. M. Steckelberg, F. Roberson, and W. R. Wilson. 1998. Molecular, serological, and clinical features of 16 consecutive cases of invasive streptococcal disease. Southeastern Minnesota Streptococcal Working Group. *Clin Infect Dis.* 26:1448-58.
18. Courtney, H. S., Y. Li, J. B. Dale, and D. L. Hasty. 1994. Cloning, sequencing, and expression of a fibronectin/fibrinogen-binding protein from group A streptococci. *Infect Immun.* 62:3937-46.
19. Cserzo, M., E. Wallin, I. Simon, G. von Heijne, and A. Elofsson. 1997. Prediction of transmembrane alpha-helices in prokaryotic membrane proteins: the dense alignment surface method. *Protein Engineering.* 10:673-6.
20. Cunningham, M. W., and A. Quinn. 1997. Immunological crossreactivity between the class I epitope of streptococcal M protein and myosin. *Adv Exp Med. Biol.* 418:887-92.
21. Dale, J. B., R. W. Baird, H. S. Courtney, D. L. Hasty, and M. S. Bronze. 1994. Passive protection of mice against group A streptococcal pharyngeal infection by lipoteichoic acid. *J Infect Dis.* 169:319-23.
22. Dale, J. B., M. Simmons, E. C. Chiang, and E. Y. Chiang. 1996. Recombinant, octavalent group A streptococcal M protein vaccine. *Vaccine.* 14:944-8.
23. Dale, J. B., R. G. Washburn, M. B. Marques, and M. R. Wessels. 1996. Hyaluronate capsule and surface M protein in resistance to opsonization of group A streptococci. *Infect Immun.* 64:1495-501.
24. Eddy, S. R. 1996. Hidden Markov models. *Cur Opin Struct Bio.* 6:361-5.
25. Ellen, R. P., and R. J. Gibbons. 1972. M protein-associated adherence of *Streptococcus pyogenes* to epithelial surfaces: prerequisite for virulence. *Infect Immun.* 5:826-830.
26. Eng, J. K., A. L. McCormack, and J. R. Yates, 3rd. 1994. An approach to correlate tandem mass-spectral data of peptides with amino-acid-sequences in a protein database. *Am Soc Mass Spectrometry.* 5:976-89.
27. Fischetti, V. A., V. Pancholi, and O, Schneewind. 1990. Conservation of a hexapeptide sequence in the anchor region of surface proteins from gram-positive cocci. *Mol. Microbiol.* 4:1603-5.
28. Fogg, G. C., and M. G. Caparon. 1997. Constitutive expression of fibronectin binding in *Streptococcus pyogenes* as a result of anaerobic activation of rofA. *J. Bacteriol.* 179:6172-80.
29. Foster, T. J., and M. Hook. 1998. Surface protein adhesins of *Staphylococcus aureus*. Trends Microbiol. 6:484-8.
30. Fraser, C. M., S. Casjens, W. M. Huang, G. G. Sutton, R. Clayton, R. Lathigra, O. White, K. A. Ketchum, R. Dodson, E. K. Hickey, M. Gwinn, B. Dougherty, J. F. Tomb, R. D. Fleischmann, D. Richardson, J. Peterson, A. R. Kerlavage, J. Quackenbush, S. Salzberg, M. Hanson, R. van Vugt, N. Palmer, M. D. Adams, J.
31. Gocayne, J. C. Venter, and et al. 1997. Genomic sequence of a Lyme disease spirochaete, *Borrelia burgdorferi* [see comments]. *Nature.* 390:580-6.
32. Goldschneider, I., E. C. Gotschlich, and M. S. Artenstein. 1969. Human immunity to the meningococcus. I. The role of humoral antibodies. *Journal of Experimental Medicine* 129(6):1307-26.
33. Goldschneider, I., E. C. Gotschlich, and M. S. Artenstein. 1969. Human immunity to the meningococcus. II. Development of natural immunity. *Journal of Experimental Medicine* 129(6):1327-48.
34. Gotschlich, E. C., I. Goldschneider, and M. S. Artenstein. 1969. Human immunity to the meningococcus. IV. Immunogenicity of group A and group C meningococcal polysaccharides in human volunteers. *Journal of Experimental Medicine* 129(6):1367-84.
35. Gotschlich, E. C., I. Goldschneider, and M. S. Artenstein. 1969. Human immunity to the meningococcus. V. The effect of immunization with meningococcal group C polysaccharide on the carrier state. *Journal of Experimental Medicine* 129(6):1385-95.
36. Green, B. A., Farley, J. E., Quinn-Dey, T., Deich, R. A., and Zlotnick, G. W. 1991. The e (P4) Outer Membrane Protein of *Haemophilus influenzae*: Biologic Activity of Anti-e Serum and Cloning and Sequencing of the Structural Gene. *Infect. Immun.* 59: 3191-3198.
37. Guzman, L-M, Belin, D., Carson, M. J., Beckwith, J. 1995. Tight Regulation, Modulation, and High-Level Expression by Vectors Containing the Arabinose PBAD Promoter. *J. Bacteriology* 177:4121-4130.
38. Hacker, J., G. Blum-Oehler, I. Muhldorfer, and H. Tschape. 1997. Pathogenicity islands of virulent bacteria: structure, function and impact on microbial evolution. *Mol. Microbiol.* 23:1089-97.
39. Hanski, E., and M. Caparon. 1992. Protein F, a fibronectin-binding protein, is an adhesion of the group A *streptococcus Streptococcus pyogenes. Proc Natl Acad. Sci., USA.* 89:6172-76.
40. Hanski, E., P. A. Horwitz, and M. G. Caparon. 1992. Expression of protein F, the fibronectin-binding protein of *Streptococcus pyogenes* JRS4, in heterologous streptococcal and enterococcal strains promotes their adherence to respiratory epithelial cells. *Infect Immun.* 60:5119-5125.
41. Hernandez-Sanchez, J., J. G. Valadez, J. V. Herrera, C. Ontiveros, and G. Guarneros. 1998. lambda bar minigene-mediated inhibition of protein synthesis involves accumulation of peptidyl-tRNA and starvation for tRNA. *EMBO Journal.* 17:3758-65.
42. Huang, T. T., H. Malke, and J. J. Ferretti. 1989. The streptokinase gene of group A streptococci: cloning, expression in *Escherichia coli*, and sequence analysis. *Mol. Microbiol.* 3:197-205.
43. Hynes, W. L., A. R. Dixon, S. L. Walton, and L. J. Aridgides. 2000. The extracellular hyaluronidase gene (hylA) of *Streptococcus pyogenes. FEMS Microbiol Lett.* 184:109-12.
44. Hynes, W. L., L. Hancock, and J. J. Ferretti. 1995. Analysis of a second bacteriophage hyaluronidase gene from *Streptococcus pyogenes*: evidence for a third hyaluronidase involved in extracellular enzymatic activity. *Infect Immun.* 63:3015-20.
45. Isberg, R. R., and G. Tran Van Nhieu. 1994. Binding and internalization of microorganisms by integrin receptors. *Trends Microbio.* 2:10-4.
46. Jones, K. F., and V. A. Fischetti. 1988. The importance of the location of antibody binding on the M6 protein for opsonization and phagocytosis of group A M6 streptococci. *J Exp Med.* 167:1114-23.
47. Kihlberg, B. M., M. Collin, A. Olsen, and L. Bjorck. 1999. Protein H, an antiphagocytic surface protein in *Streptococcus pyogenes. Infect Immun.* 67:1708-14.
48. Koebnik, R. 1995. Proposal for a peptidoglycan-associating alpha-helical motif in the C-terminal regions of some bacterial cell-surface proteins [letter; comment]. *Molecular Microbiology.* 16:1269-70.
49. Kuipers, O. P., H. J. Boot, and W. M. de Vos. 1991. Improved site-directed mutagenesis method using PCR. *Nucleic Acids Res.* 19:4558.
50. Kyte, J., and R. F. Doolittle. 1982. A simple method for displaying the hydropathic character of a protein. *Journal of Molecular Biology* 157:105-132.
51. Landt, O., H. P. Grunert, and U. Hahn. 1990. A general method for rapid site-directed mutagenesis using the polymerase chain reaction. *Gene* 96:125-128.
52. Loessner, M. J., S. Gaeng, and S. Scherer. 1999. Evidence for a holin-like protein gene fully embedded out of frame in the endolysin gene of *Staphylococcus aureus* bacteriophage 187. *J. Bacteriol.* 181:4452-60.
53. Lukashin, A. V., and M. Borodovsky. 1998. GeneMark.hmm: new solutions for gene finding. *Nucleic Acids Res.* 26:1107-15.
54. Lukomski, S., C. A. Montgomery, J. Rurangirwa, R. S. Geske, J. P. Barrish, G. J. Adams, and J. M. Musser. 1999. Extracellular cysteine protease produced by *Streptococcus pyogenes* participates in the pathogenesis of invasive skin infection and dissemination in mice. *Infect Immun.* 67:1779-88.
55. Madore, D. V. 1998. Characterization of immune response as an indicator of *Haemophilus influenzae* type b vaccine efficacy. *Pediatr Infect Dis J.* 17:S207-10.
56. Matsuka, Y. V., S. Pillai, S. Gubba, J. M. Musser, and S. B. Olmsted. 1999. Fibrinogen cleavage by the *Streptococcus pyogenes* extracellular cysteine protease and generation of antibodies that inhibit enzyme proteolytic activity. *Infect Immun.* 67:4326-33.
57. Mazmanian, S. K., G. Liu, H. Ton-That, and O. Schneewind. 1999. *Staphylococcus aureus* sortase, an enzyme that anchors surface proteins to the cell wall. *Science.* 285: 760-3.
58. McAtee, C. P., K. E. Fry, and D. E. Berg. 1998. Identification of potential diagnostic and vaccine candidates of *Helicobacter* pylori by "proteome" technologies. *Helicobacter.* 3:163-9.
59. McAtee, C. P., M. Y. Lim, K. Fung, M. Velligan, K. Fry, T. Chow, and D. E. Berg. 1998. Identification of potential diagnostic and vaccine candidates of *Helicobacter pylori* by two-dimensional gel electrophoresis, sequence analysis, and serum profiling. *Clin Diagn Lab Immunol.* 5:537-42.
60. McAtee, C. P., M. Y. Lim, K. Fung, M. Velligan, K. Fry, T. P. Chow, and D. E. Berg. 1998. Characterization of a *Helicobacter pylori* vaccine candidate by proteome techniques. *J Chromatogr B Biomed Sci Appl.* 714:325-33.
61. Mejlhede, N., J. F. Atkins, and J. Neuhard. 1999. Ribosomal-1 frameshifting during decoding of *Bacillus subtilis* cdd occurs at the sequence CGA AAG. *J. Bacteriol.* 181: 2930-7.
62. Molinari, G., S. R. Talay, P. Valentin-Weigand, M. Rohde, and G. S. Chhatwal. 1997. The fibronectin-binding protein of *Streptococcus pyogenes*, SfbI, is involved in the internalization of group A streptococci by epithelial cells. *Infect Immun.* 65:1357-63.
63. Mountzouros, K. T., and A. P. Howell. 2000. Detection of complement-mediated antibody-dependent bactericidal activity in a fluorescence-based serum bactericidal assay for group B *Neisseria meningitidis. J. Clin. Microbiol.* 38(8):2878-2884.
64. Nakai, K., and M. Kanehisa. 1991. Expert system for predicting protein localization sites in gram-negative bacteria. *Proteins.* 11:95-110.
65. Navarre, W. W., and O, Schneewind. 1999. Surface proteins of gram-positive bacteria and mechanisms of their targeting to the cell wall envelope. *Microbiol. Mol Biol Rev.* 63:174-229.
66. Nielsen, H., J. Engelbrecht, S. Brunak, and G. von Heijne. 1997. Identification of prokaryotic and eukaryotic signal peptides and prediction of their cleavage sites. *Protein Engineering.* 10:1-6.
67. Nizet, V., B. Beall, D. J. Bast, V. Datta, L. Kilburn, D. E. Low, and J. C. De Azavedo. 2000. Genetic locus for streptolysin S production by group A *streptococcus. Infect Immun.* 68:4245-54.
68. Nordstrand, A., W. M. McShan, J. J. Ferretti, S. E. Holm, and M. Norgren. 2000. Allele substitution of the streptoki- 68. nase gene reduces the nephritogenic capacity of group A streptococcal strain NZ131. *Infect Immun.* 68:1019-25.
69. Olmsted, S. B., S. L. Erlandsen, G. M. Dunny, and C. L. Wells. 1993. High-resolution visualization by field emission scanning electron microscopy of *Enterococcus faecalis* surface proteins encoded by the pheromone-inducible conjugative plasmid pCF10. *J. Bacteriol.* 175:6229-37.
70. Park, J., and S. A. Teichmann. 1998. DIVCLUS: an automatic method in the GEANFAMMER package that finds homologous domains in single- and multi-domain proteins. *Bioinformatics.* 14:144-50.
71. Parkhill, J., M. Achtman, K. D. James, S. D. Bentley, C. Churcher, S. R. Klee, G. Morelli, D. Basham, D. Brown, T. Chillingworth, R. M. Davies, P. Davis, K. Devlin, T. Feltwell, N. Hamlin, S. Holroyd, K. Jagels, S. Leather, S. Moule, K. Mungall, M. A. Quail, M. A. Rajandream, K. M. Rutherford, M. Simmonds, J. Skelton, S. Whitehead, B. G. Spratt, and B. G. Barrell. 2000. Complete DNA sequence of a serogroup A strain of *Neisseria meningitidis* Z2491 [see comments]. *Nature.* 404:502-6.
72. Pierschbacher, M. D., and E. Ruoslahti. 1987. Influence of stereochemistry of the sequence Arg-Gly-Asp-Xaa on binding specificity in cell adhesion. *J Biol. Chem.* 262:17294-8.
73. Pizza, M., V. Scarlato, V. Masignani, M. M. Giuliani, B. Arico, M. Comanducci, G. T. Jennings, L. Baldi, E. Bartolini, B. Capecchi, C. L. Galeotti, E. Luzzi, R. Manetti, E. Marchetti, M. Mora, S. Nuti, G. Ratti, L. Santini, S. Savino, M. Scarselli, E. Storni, P. Zuo, M. Broeker, E. Hundt, B. Knapp, E. Blair, T. Mason, H. Tettelin, D. W. Hood, A. C. Jeffries, N.J. Saunders, D. M. Granoff, J. C. Venter, E. R. Moxon, G. Grandi, and R. Rappuoli. 2000. Identification of vaccine candidates against serogroup B meningococcus by whole-genome sequencing. *Science* 287(5459):1816-20.
74. Podbielski, A., A. Flosdorff, and J. Weber-Heynemann. 1995. The group A streptococcal virR49 gene controls expression of four structural vir regulon genes. *Infect Immun.* 63:9-20.
75. Poolman, J. T. 1996. Bacterial outer membrane protein vaccines. The meningococcal example. *Advances in Experimental Medicine & Biology* 397:73-7.
76. Prot T., S. Louise Moffatt, C. J. Berkahn, and J. D. Fraser. 1999. Identification and Characterization of Novel Superantigens from *Streptococcus pyogenes*. *J Exp Med.* 189:89-102.
77. Pugsley, A. P. 1993. The complete general secretory pathway in gram-negative bacteria. *Microbiol. Rev.* 57:50-108.
78. Quinn, A., K. Ward, V. A. Fischetti, M. Hemric, and M. W. Cunningham. 1998. Immunological relationship between the class I epitope of streptococcal M protein and myosin. *Infect Immun.* 66:4418-24.
79. Reda, K. B., V. Kapur, D. Goela, J. G. Lamphear, J. M. Musser, and R. R. Rich. 1996. Phylogenetic distribution of streptococcal superantigen SSA allelic variants provides evidence for horizontal transfer of ssa within *Streptococcus pyogenes*. *Infect Immun.* 64:1161-5.
80. Sambrook, J., and D. W. Russell. 2001. *Molecular cloning a laboratory manual*, Third ed, vol. 3. Cold Spring Harbor Laboratory Press, Cold Spring Harbor, N.Y.
81. Salzberg, S. L., A. L. Delcher, S. Kasif, and O. White. 1998. Microbial gene identification using interpolated Markov models. *Nucleic Acids Res.* 26:544-8.
82. Saukkonen, K., H. Abdillahi, J. T. Poolman, and M. Leinonen. 1987. Protective efficacy of monoclonal antibodies to class 1 and class 3 outer membrane proteins of *Neisseria meningitidis* B:15:P1.16 in infant rat infection model: new prospects for vaccine development. *Microbial Pathogenesis* 3(4):261-7.
83. Sedegah et al. 1994. *Immunology.* 91, 9866-9870.
84. Sonnenberg, M. G., and J. T. Belisle. 1997. Definition of *Mycobacterium tuberculosis* culture filtrate proteins by two-dimensional polyacrylamide gel electrophoresis, N-terminal amino acid sequencing, and electrospray mass spectrometry. *Infect Immun.* 65:4515-24.
85. Sonnhammer, E. L., S. R. Eddy, and R. Durbin. 1997. Pfam: a comprehensive database of protein domain families based on seed alignments. *Proteins.* 28:405-20.
86. Stevens, D. L. 1995. Streptococcal toxic-shock syndrome: spectrum of disease, pathogenesis, and new concepts in treatment. *Emerg Infect Dis.* 1:69-78.
87. Stockbauer, K. E., L. Magoun, M. Liu, E. H. Burns, Jr., S. Gubba, S. Renish, X. Pan, S. C. Bodary, E. Baker, J. Coburn, J. M. Leong, and J. M. Musser. 1999. A natural variant of the cysteine protease virulence factor of group A streptococcus with an arginine-glycine-aspartic acid (RGD) motif preferentially binds human integrins alphavbeta3 and alphaIIbbeta3 *Proc Natl Acad. Sci., USA.* 96:242-7.
88. Tettelin, H., N. J. Saunders, J. Heidelberg, A. C. Jeffries, K. E. Nelson, J. A. Eisen, K. A. Ketchum, D. W. Hood, J. F. Peden, R. J. Dodson, W. C. Nelson, M. L. Gwinn, R. DeBoy, J. D. Peterson, E. K. Hickey, D. H. Haft, S. L. Salzberg, O. White, R. D. Fleischmann, B. A. Dougherty, T. Mason, A. Ciecko, D. S. Parksey, E. Blair, H. Cittone, E. B. Clark, M. D. Cotton, T. R. Utterback, H. Khouri, H. Qin, J. Vamathevan, J. Gill, V. Scarlato, V. Masignani, M. Pizza, G. Grandi, L. Sun, H. O, Smith, C. M. Fraser, E. R. Moxon, R. Rappuoli, and J. C. Venter. 2000. Complete genome sequence of *Neisseria meningitidis* serogroup B strain MC58. *Science* 287(5459):1809-15.
89. Ton-That, H., G. Liu, S. K. Mazmanian, K. F. Faull, and O, Schneewind. 1999. Purification and characterization of sortase, the transpeptidase that cleaves surface proteins of *Staphylococcus aureus* at the LPXTG motif. *Proc Natl Acad Sci USA.* 96:12424-12429.
90. von Heinje, G. 1987. Sequence Analysis in Molecular Biology. Academic Press, New York.
91. Weldingh, K., I. Rosenkrands, S. Jacobsen, P. B. Rasmussen, M. J. Elhay, and P. Andersen. 1998. Two-dimensional electrophoresis for analysis of *Mycobacterium tuberculosis* culture filtrate and purification and characterization of six novel proteins. *Infect Immun.* 66:3492-500.
92. Wolff et al., 1990. *Science.* 247, 1465-1468.
93. Yutsudo, T., K. Okumura, M. Iwasaki, A. Hara, S. Kamitani, W. Minamide, H. Igarashi, and Y. Hinuma. 1994. The gene encoding a new mitogenic factor in a *Streptococcus pyogenes* strain is distributed only in group A streptococci. *Infection and Immunity.* 62:4000-4004.
94. Zagursky, R. J. and D. Russell. 2001. Bioinformatics: Use in Bacterial Vaccine Discovery. *BioTechniques.* 31:636-659.

The invention now being fully described, it will be apparent to one of ordinary skill in the art that many changes and modifications can be made thereto without departing from the spirit or scope of the invention as set forth herein. The foregoing describes the preferred embodiments of the present invention along with a number of possible alternatives. These embodiments, however, are merely for example and the invention is not restricted thereto.

What is claimed is:

1. An isolated polypeptide comprising the amino acid sequence set forth in any of the even numbered sequences of SEQ ID NOS:2-12.

2. The polypeptide of claim 1, wherein the polypeptide is encoded by the nucleic acid sequence of any one of the odd numbered sequences of SEQ ID NOS: 1-11.

3. The polypeptide of claim 1, wherein the polypeptide comprises the amino acid sequence of any of the even numbered sequences of SEQ ID NOS: 2-6.

4. The polypeptide of claim 3, wherein the polypeptide is encoded by the nucleic acid sequence of any one of the odd numbered sequences of SEQ ID NOS: 1-5.

5. The polypeptide of claim 1, wherein the polypeptide comprises the amino acid sequence of any of the even numbered sequences of SEQ ID NOS:8-12.

6. The polypeptide of claim 5, wherein the polypeptide is encoded by the nucleic acid sequence of any one of the odd numbered sequences of SEQ ID NOS: 7-11.

7. The polypeptide of claim 1, wherein the polypeptide has a molecular weight of 26,000 to 30,000 Daltons as measured by mass spectroscopy.

8. The polypeptide of claim 1, wherein the polypeptide has a molecular weight of 28-35 kDa as measured on a 10%-20% SDS polyacrylamide gel.

9. The polypeptide of claim 1, wherein the polypeptide is non-lipidated.

10. The polypeptide of claim 1, wherein the polypeptide is a recombinant protein.

11. A composition comprising the polypeptide of claim 1.

12. The composition of claim 11, wherein said composition additionally comprises a carrier.

13. The composition of claim 11, wherein said composition additionally comprises an adjuvant.

14. The composition of claim 13, wherein said adjuvant comprises a liquid.

15. The composition of claim 11, wherein said composition additionally comprises a polysaccharide.

16. An isolated polypeptide prepared by a process comprising isolating and purifying from *Neisseria meningitidis* or recombinantly preparing any of:
   (a) a polypeptide comprising the amino acid sequence of any of even numbered SEQ ID NOS: 2-12 or
   (b) a polypeptide encoded by a polynucleotide comprising the nucleic acid sequence of any of odd numbered SEQ ID NOS: 1-11.

17. A method of inducing an immune response against *Neisseria meningitidis* in a mammal comprising administering to the mammal an immunologically effective amount of the composition of claim 11.

18. The method of claim 17, wherein said composition is administered parenterally.

19. The method of claim 17, wherein said composition is administered mucosally.

20. The composition of claim 11, wherein the composition additionally comprises an additional peptide, polypeptide or protein.

21. An isolated polypeptide comprising the amino acid sequence set forth in SEQ ID NO: 12.

22. The polypeptide of claim 21, wherein the polypeptide consists of the amino acid sequence set forth in SEQ ID NO: 12.

23. The polypeptide of claim 21, wherein the polypeptide is non-lipidated.

24. An immunogenic composition comprising an isolated polypeptide having the amino acid sequence set forth in SEQ ID NO: 12.

25. The composition of claim 14, wherein the polypeptide is non-lipidated.

* * * * *

SEQUENCE LISTING

<160> NUMBER OF SEQ ID NOS: 15

<210> SEQ ID NO 1
<211> LENGTH: 786
<212> TYPE: DNA
<213> ORGANISM: Neisseria

<400> SEQUENCE: 1

```
tgcagcagcg gaggcggcgg aagcggaggc ggcggtgtcg ccgccgacat cggcacgggg     60
cttgccgatg cactaactgc gccgctcgac cataaagaca aaggtttgaa atccctgaca    120
ttggaagact ctattcccca aaacggaaca ctaaccctgt cggcacaagg tgcggaaaaa    180
actttcaaag ccggcgacaa agacaacagc ctcaacacgg gcaaactgaa gaacgacaaa    240
atcagccgct tcgactttgt gcaaaaaatc gaagtggacg gacaaaccat cacgctggca    300
agcggcgaat ttcaaatata caacaggac cactccgccg tcgttgccct acagattgaa    360
aaaatcaaca accccgacaa aatcgacagc ctgataaacc aacgctcctt ccttgtcagc    420
ggtttgggcg gagaacatac cgccttcaac caactgcccg gcggcaaagc cgagtatcac    480
ggcaaagcat tcagctccga cgacccgaac ggcaggctgc actactccat tgatttacc     540
aaaaaacagg gttacggcag aatcgaacac ctgaaaacac ccgagcaaaa tgtcgagctt    600
gcctccgccg aactcaaagc agatgaaaaa tcacacgccg tcattttggg cgacacgcgc    660
tacggcagcg aagaaaaagg cacttaccac ctcgcccttt tcggcgaccg cgcccaagaa    720
atcgccggct cggcaaccgt gaagataggg gaaaaggttc acgaaatcgg catcgccggc    780
aaacag                                                              786
```

<210> SEQ ID NO 2
<211> LENGTH: 262
<212> TYPE: PRT
<213> ORGANISM: Neisseria

<400> SEQUENCE: 2

```
Cys Ser Ser Gly Gly Gly Ser Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asp His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175
```

```
Ile Asp Phe Thr Lys Lys Gln Gly Tyr Gly Arg Ile Glu His Leu Lys
            180                 185                 190

Thr Pro Glu Gln Asn Val Glu Leu Ala Ser Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260
```

<210> SEQ ID NO 3
<211> LENGTH: 792
<212> TYPE: DNA
<213> ORGANISM: Neisseria

<400> SEQUENCE: 3

```
tgcggatcca gcagcggagg cggcggaagc ggaggcggcg tgtcgccgc cgacatcggc      60
acggggcttg ccgatgcact aactgcgccg ctcgaccata agacaaagg tttgaaatcc     120
ctgacattgg aagactctat tccccaaaac ggaacactaa ccctgtcggc acaaggtgcg   180
gaaaaaactt tcaaagccgg cgacaaagac aacagcctca cacgggcaa actgaagaac    240
gacaaaatca gccgcttcga ctttgtgcaa aaatcgaag tggacggaca aaccatcacg    300
ctggcaagcg gcgaatttca aatatacaaa caggaccact ccgccgtcgt tgccctacag   360
attgaaaaaa tcaacaaccc cgacaaaatc gacagcctga taaccaacg ctccttcctt    420
gtcagcggtt tgggcggaga acataccgcc ttcaaccaac tgcccggcgg caaagccgag   480
tatcacggca agcattcag ctccgacgac ccgaacggca gctgcacta ctccattgat     540
tttaccaaaa acagggtta cggcagaatc gaacacctga aacacccga gcaaaatgtc     600
gagcttgcct ccgccgaact caaagcagat gaaaaatcac acgccgtcat tttgggcgac   660
acgcgctacg gcagcgaaga aaaaggcact taccacctcg cccttttcgg cgaccgcgcc   720
caagaaatcg ccggctcggc aaccgtgaag ataggggaaa aggttcacga aatcggcatc   780
gccggcaaac ag                                                        792
```

<210> SEQ ID NO 4
<211> LENGTH: 263
<212> TYPE: PRT
<213> ORGANISM: Neisseria

<400> SEQUENCE: 4

```
Cys Gly Ser Ser Gly Gly Gly Ser Gly Gly Gly Gly Val Ala Ala
1               5                   10                  15

Asp Ile Gly Thr Gly Leu Ala Asp Ala Leu Thr Ala Pro Leu Asp His
            20                  25                  30

Lys Asp Lys Gly Leu Lys Ser Leu Thr Leu Glu Asp Ser Ile Pro Gln
        35                  40                  45

Asn Gly Thr Leu Thr Leu Ser Ala Gln Gly Ala Glu Lys Thr Phe Lys
    50                  55                  60

Ala Gly Asp Lys Asp Asn Ser Leu Asn Thr Gly Lys Leu Lys Asn Asp
65                  70                  75                  80

Lys Ile Ser Arg Phe Asp Phe Val Gln Lys Ile Glu Val Asp Gly Gln
                85                  90                  95
```

```
Thr Ile Thr Leu Ala Ser Gly Glu Phe Gln Ile Tyr Lys Gln Asp His
            100                 105                 110

Ser Ala Val Ala Leu Gln Ile Glu Lys Ile Asn Asn Pro Asp Lys
        115                 120                 125

Ile Asp Ser Leu Ile Asn Gln Arg Ser Phe Leu Val Ser Gly Leu Gly
    130                 135                 140

Gly Glu His Thr Ala Phe Asn Gln Leu Pro Gly Gly Lys Ala Glu Tyr
145                 150                 155                 160

His Gly Lys Ala Phe Ser Ser Asp Pro Asn Gly Arg Leu His Tyr
                165                 170                 175

Ser Ile Asp Phe Thr Lys Lys Gln Gly Tyr Gly Arg Ile Glu His Leu
            180                 185                 190

Lys Thr Pro Glu Gln Asn Val Glu Leu Ala Ser Ala Glu Leu Lys Ala
        195                 200                 205

Asp Glu Lys Ser His Ala Val Ile Leu Gly Asp Thr Arg Tyr Gly Ser
    210                 215                 220

Glu Glu Lys Gly Thr Tyr His Leu Ala Leu Phe Gly Asp Arg Ala Gln
225                 230                 235                 240

Glu Ile Ala Gly Ser Ala Thr Val Lys Ile Gly Lys Val His Glu
                245                 250                 255

Ile Gly Ile Ala Gly Lys Gln
            260

<210> SEQ ID NO 5
<211> LENGTH: 786
<212> TYPE: DNA
<213> ORGANISM: Neisseria

<400> SEQUENCE: 5
atgagcagcg gaggcggcgg aagcggaggc ggcggtgtcg ccgccgacat cggcacgggg      60
cttgccgatg cactaactgc gccgctcgac cataaagaca aggtttgaa atccctgaca      120 ttggaagact ctattcccca aaacggaaca ctaaccctgt cggcacaagg tgcggaaaaa      180
actttcaaag ccggcgacaa agacaacagc ctcaacacgg caaactgaa gaacgacaaa      240 atcagccgct tcgactttgt gcaaaaaatc gaagtggacg acaaaccat cacgctggca      300 agcggcgaat tcaaatata caaacaggac cactccgccg tcgttgccct acagattgaa      360
aaaatcaaca ccccgacaa aatcgacagc ctgataaaacc aacgctcctt ccttgtcagc      420
ggtttgggcg gagaacatac cgccttcaac caactgcccg gcggcaaagc cgagtatcac      480
ggcaaagcat tcagctccga cgacccgaac ggcaggctgc actactccat tgattttacc      540
aaaaaacagg gttacggcag aatcgaacac ctgaaaacac ccgagcaaaa tgtcgagctt      600
gcctccgccg aactcaaagc agatgaaaaa tcacacgccg tcattttggg cgacacgcgc      660
tacggcagcg aagaaaagg cacttaccac ctcgcccttt tcggcgaccg cgcccaagaa      720
atcgccggct cggcaaccgt gaagataggg gaaaaggttc acgaaatcgg catcgccggc      780
aaacag                                                               786

<210> SEQ ID NO 6
<211> LENGTH: 262
<212> TYPE: PRT
<213> ORGANISM: Neisseria

<400> SEQUENCE: 6

Met Ser Ser Gly Gly Gly Ser Gly Gly Gly Gly Val Ala Ala Asp
1               5                   10                  15
```

Ile Gly Thr Gly Leu Ala Asp Ala Leu Thr Ala Pro Leu Asp His Lys
          20                  25                  30

Asp Lys Gly Leu Lys Ser Leu Thr Leu Glu Asp Ser Ile Pro Gln Asn
          35                  40                  45

Gly Thr Leu Thr Leu Ser Ala Gln Gly Ala Glu Lys Thr Phe Lys Ala
 50                  55                  60

Gly Asp Lys Asp Asn Ser Leu Asn Thr Gly Lys Leu Lys Asn Asp Lys
 65                  70                  75                  80

Ile Ser Arg Phe Asp Phe Val Gln Lys Ile Glu Val Asp Gly Gln Thr
                  85                  90                  95

Ile Thr Leu Ala Ser Gly Glu Phe Gln Ile Tyr Lys Gln Asp His Ser
                 100                 105                 110

Ala Val Val Ala Leu Gln Ile Glu Lys Ile Asn Asn Pro Asp Lys Ile
                 115                 120                 125

Asp Ser Leu Ile Asn Gln Arg Ser Phe Leu Val Ser Gly Leu Gly Gly
         130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                 165                 170                 175

Ile Asp Phe Thr Lys Lys Gln Gly Tyr Gly Arg Ile Glu His Leu Lys
             180                 185                 190

Thr Pro Glu Gln Asn Val Glu Leu Ala Ser Ala Glu Leu Lys Ala Asp
         195                 200                 205

Glu Lys Ser His Ala Val Ile Leu Gly Asp Thr Arg Tyr Gly Ser Glu
 210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                 245                 250                 255

Gly Ile Ala Gly Lys Gln
                 260

<210> SEQ ID NO 7
<211> LENGTH: 792
<212> TYPE: DNA
<213> ORGANISM: Neisseria

<400> SEQUENCE: 7
tgcagcagcg gaggcggcgg aagcggaggc ggcggtgtcg ccgccgacat cggcgcgggg      60
cttgccgatg cactaaccgc accgctcgac cataaagaca aaggtttgaa atccctgaca     120
ttggaagact ccatttccca aaacggaaca ctgaccctgt cggcacaagg tgcggaaaga     180
actttcaaag ccggcgacaa agacaacagt ctcaacacag gcaaactgaa gaacgacaaa     240
atcagccgct tcgactttat ccgtcaaatc gaagtggacg gcagctcat  tccttggag     300 agcggagagt tccaagtgta caaacaaagc cattccgcct taaccgccct tcagaccgag     360
caagtacaag actcggagca ttccgggaag atggttgcga acgccagtt cagaatcggc      420 gacatagtgg cgaacatac atctttgac aagcttccca agacgtcat ggcgacatat       480 cgcgggacgg cgttcggttc agacgatgcc ggcgaaaac tgacctacac catagatttc      540
gccgccaagc agggacacgg caaaatcgaa catttgaaat cgcctgaact caatgttgac     600
ctggccgccg ccgatatcaa gccggatgaa aaacaccatg ccgtcatcag cggttccgtc     660
ctttacaacc aagccgagaa aggcagttac tctctaggca tctttggcgg gcaagcccag     720

```
gaagttgccg gcagcgcgga agtggaaacc gcaaacggca tacgccatat cggtcttgcc    780
gccaagcaat aa                                                        792
```

<210> SEQ ID NO 8
<211> LENGTH: 263
<212> TYPE: PRT
<213> ORGANISM: Neisseria

<400> SEQUENCE: 8

```
Cys Ser Ser Gly Gly Gly Ser Gly Gly Gly Val Ala Ala Asp
1               5                   10                  15

Ile Gly Ala Gly Leu Ala Asp Ala Leu Thr Ala Pro Leu Asp His Lys
                20                  25                  30

Asp Lys Gly Leu Lys Ser Leu Thr Leu Glu Asp Ser Ile Ser Gln Asn
            35                  40                  45

Gly Thr Leu Thr Leu Ser Ala Gln Gly Ala Glu Arg Thr Phe Lys Ala
        50                  55                  60

Gly Asp Lys Asp Asn Ser Leu Asn Thr Gly Lys Leu Lys Asn Asp Lys
65                  70                  75                  80

Ile Ser Arg Phe Asp Phe Ile Arg Gln Ile Glu Val Asp Gly Gln Leu
                85                  90                  95

Ile Thr Leu Glu Ser Gly Glu Phe Gln Val Tyr Lys Gln Ser His Ser
            100                 105                 110

Ala Leu Thr Ala Leu Gln Thr Glu Gln Val Gln Asp Ser Glu His Ser
        115                 120                 125

Gly Lys Met Val Ala Lys Arg Gln Phe Arg Ile Gly Asp Ile Val Gly
    130                 135                 140

Glu His Thr Ser Phe Asp Lys Leu Pro Lys Asp Val Met Ala Thr Tyr
145                 150                 155                 160

Arg Gly Thr Ala Phe Gly Ser Asp Asp Ala Gly Gly Lys Leu Thr Tyr
                165                 170                 175

Thr Ile Asp Phe Ala Ala Lys Gln Gly His Gly Lys Ile Glu His Leu
            180                 185                 190

Lys Ser Pro Glu Leu Asn Val Asp Leu Ala Ala Ala Asp Ile Lys Pro
        195                 200                 205

Asp Glu Lys His His Ala Val Ile Ser Gly Ser Val Leu Tyr Asn Gln
    210                 215                 220

Ala Glu Lys Gly Ser Tyr Ser Leu Gly Ile Phe Gly Gly Gln Ala Gln
225                 230                 235                 240

Glu Val Ala Gly Ser Ala Glu Val Glu Thr Ala Asn Gly Ile Arg His
                245                 250                 255

Ile Gly Leu Ala Ala Lys Gln
            260
```

<210> SEQ ID NO 9
<211> LENGTH: 798
<212> TYPE: DNA
<213> ORGANISM: Neisseria

<400> SEQUENCE: 9

```
tgcggatcca gcagcggagg cggcggaagc ggaggcggcg tgtcgccgc cgacatcggc     60 gcggggcttg ccgatgcact aaccgcaccg ctcgaccata agacaaagg tttgaaatcc    120 ctgacattgg aagactccat ttcccaaaac ggaacactga ccctgtcggc acaaggtgcg    180
gaaagaactt tcaaagccgg cgacaaagac aacagtctca cacacaggcaa actgaagaac    240
```

```
gacaaaatca gccgcttcga ctttatccgt caaatcgaag tggacgggca gctcattacc    300
ttggagagcg gagagttcca agtgtacaaa caaagccatt ccgccttaac cgcccttcag    360
accgagcaag tacaagactc ggagcattcc gggaagatgg ttgcgaaacg ccagttcaga    420
atcggcgaca tagtgggcga acatacatct tttgacaagc ttcccaaaga cgtcatggcg    480
acatatcgcg ggacggcgtt cggttcagac gatgccggcg aaaactgac  ctacaccata    540 gatttcgccg ccaagcaggg cacggcaaa  atcgaacatt tgaaatcgcc tgaactcaat    600
gttgacctgg ccgccgccga tatcaagccg gatgaaaaac accatgccgt catcagcggt    660
tccgtccttt acaaccaagc cgagaaaggc agttactctc taggcatctt tggcgggcaa    720
gcccaggaag ttgccggcag cgcggaagtg gaaaccgcaa acggcatacg ccatatcggt    780
cttgccgcca agcaataa                                                  798

<210> SEQ ID NO 10
<211> LENGTH: 264
<212> TYPE: PRT
<213> ORGANISM: Neisseria

<400> SEQUENCE: 10

Cys Gly Ser Ser Gly Gly Gly Ser Gly Gly Gly Val Ala Ala
1               5                   10                  15

Asp Ile Gly Ala Gly Leu Ala Asp Ala Leu Thr Ala Pro Leu Asp His
            20                  25                  30

Lys Asp Lys Gly Leu Lys Ser Leu Thr Leu Glu Asp Ser Ile Ser Gln
        35                  40                  45

Asn Gly Thr Leu Thr Leu Ser Ala Gln Gly Ala Glu Arg Thr Phe Lys
    50                  55                  60

Ala Gly Asp Lys Asp Asn Ser Leu Asn Thr Gly Lys Leu Lys Asn Asp
65                  70                  75                  80

Lys Ile Ser Arg Phe Asp Phe Ile Arg Gln Ile Glu Val Asp Gly Gln
                85                  90                  95

Leu Ile Thr Leu Glu Ser Gly Glu Phe Gln Val Tyr Lys Gln Ser His
            100                 105                 110

Ser Ala Leu Thr Ala Leu Gln Thr Glu Gln Val Gln Asp Ser Glu His
        115                 120                 125

Ser Gly Lys Met Val Ala Lys Arg Gln Phe Arg Ile Gly Asp Ile Val
    130                 135                 140

Gly Glu His Thr Ser Phe Asp Lys Leu Pro Lys Asp Val Met Ala Thr
145                 150                 155                 160

Tyr Arg Gly Thr Ala Phe Gly Ser Asp Asp Ala Gly Gly Lys Leu Thr
                165                 170                 175

Tyr Thr Ile Asp Phe Ala Ala Lys Gln Gly His Gly Lys Ile Glu His
            180                 185                 190

Leu Lys Ser Pro Glu Leu Asn Val Asp Leu Ala Ala Ala Asp Ile Lys
        195                 200                 205

Pro Asp Glu Lys His His Ala Val Ile Ser Gly Ser Val Leu Tyr Asn
    210                 215                 220

Gln Ala Glu Lys Gly Ser Tyr Ser Leu Gly Ile Phe Gly Gly Gln Ala
225                 230                 235                 240

Gln Glu Val Ala Gly Ser Ala Glu Val Glu Thr Ala Asn Gly Ile Arg
                245                 250                 255

His Ile Gly Leu Ala Ala Lys Gln
            260
```

-continued

```
<210> SEQ ID NO 11
<211> LENGTH: 792
<212> TYPE: DNA
<213> ORGANISM: Neisseria

<400> SEQUENCE: 11
atgagcagcg gaggcggcgg aagcggaggc ggcggtgtcg ccgccgacat cggcgcgggg      60
cttgccgatg cactaaccgc accgctcgac cataaagaca aaggtttgaa atccctgaca     120
ttggaagact ccatttccca aaacggaaca ctgaccctgt cggcacaagg tgcggaaaga     180
actttcaaag ccggcgacaa agacaacagt ctcaacacag gcaaactgaa gaacgacaaa     240
atcagccgct tcgactttat ccgtcaaatc gaagtggacg ggcagctcat taccttggag     300
agcggagagt tccaagtgta caaacaaagc cattccgcct taaccgccct tcagaccgag     360
caagtacaag actcggagca ttccgggaag atggttgcga acgccagtt cagaatcggc      420 gacatagtgg cgaacatac atcttttgac aagcttccca agacgtcat ggcgacatat       480 cgcgggacgg cgttcggttc agacgatgcc ggcggaaaac tgacctacac catagatttc     540
gccgccaagc agggacacgg caaaatcgaa catttgaaat cgcctgaact caatgttgac     600
ctggccgccg ccgatatcaa gccggatgaa aaacaccatg ccgtcatcag cggttccgtc     660
ctttacaacc aagccgagaa aggcagttac tctctaggca tctttggcgg gcaagcccag     720
gaagttgccg gcagcgcgga agtggaaacc gcaaacggca tacgccatat cggtcttgcc     780
gccaagcaat aa                                                          792

<210> SEQ ID NO 12
<211> LENGTH: 263
<212> TYPE: PRT
<213> ORGANISM: Neisseria

<400> SEQUENCE: 12

Met Ser Ser Gly Gly Gly Gly Ser Gly Gly Gly Gly Val Ala Ala Asp
1               5                   10                  15

Ile Gly Ala Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Arg Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Ile Arg Gln Ile Glu Val Asp Gly Gln Leu
                85                  90                  95

Ile Thr Leu Glu Ser Gly Glu Phe Gln Val Tyr Lys Gln Ser His Ser
            100                 105                 110

Ala Leu Thr Ala Leu Gln Thr Glu Gln Val Gln Asp Ser Glu His Ser
        115                 120                 125

Gly Lys Met Val Ala Lys Arg Gln Phe Arg Ile Gly Asp Ile Val Gly
    130                 135                 140

Glu His Thr Ser Phe Asp Lys Leu Pro Lys Asp Val Met Ala Thr Tyr
145                 150                 155                 160

Arg Gly Thr Ala Phe Gly Ser Asp Asp Ala Gly Gly Lys Leu Thr Tyr
                165                 170                 175

Thr Ile Asp Phe Ala Ala Lys Gln Gly His Gly Lys Ile Glu His Leu
            180                 185                 190

Lys Ser Pro Glu Leu Asn Val Asp Leu Ala Ala Ala Asp Ile Lys Pro
```

-continued

```
                    195                 200                 205
Asp Glu Lys His His Ala Val Ile Ser Gly Ser Val Leu Tyr Asn Gln
            210                 215                 220

Ala Glu Lys Gly Ser Tyr Ser Leu Gly Ile Phe Gly Gly Gln Ala Gln
225                 230                 235                 240

Glu Val Ala Gly Ser Ala Glu Val Glu Thr Ala Asn Gly Ile Arg His
                245                 250                 255

Ile Gly Leu Ala Ala Lys Gln
            260

<210> SEQ ID NO 13
<211> LENGTH: 25
<212> TYPE: PRT
<213> ORGANISM: Neisseria

<400> SEQUENCE: 13

Cys Ser Ser Gly Gly Gly Gly Val Ala Ala Asp Ile Gly Ala Gly Leu
1               5                   10                  15

Ala Asp Ala Leu Thr Ala Pro Leu Asp
            20                  25

<210> SEQ ID NO 14
<211> LENGTH: 25
<212> TYPE: PRT
<213> ORGANISM: Neisseria

<400> SEQUENCE: 14

Cys Ser Ser Gly Gly Gly Gly Val Ala Ala Asp Ile Gly Ala Gly Leu
1               5                   10                  15

Ala Asp Ala Leu Thr Ala Pro Leu Asp
            20                  25

<210> SEQ ID NO 15
<211> LENGTH: 30
<212> TYPE: PRT
<213> ORGANISM: Neisseria

<400> SEQUENCE: 15

Cys Ser Ser Gly Gly Gly Gly Ser Gly Gly Gly Val Thr Ala Asp
1               5                   10                  15

Ile Gly Thr Gly Leu Ala Asp Ala Leu Thr Ala Pro Leu Asp
            20                  25                  30
```